US012419850B1

(12) United States Patent
Tadaki et al.

(10) Patent No.: US 12,419,850 B1
(45) Date of Patent: Sep. 23, 2025

(54) BIOACTIVE FLUID COMPOSITIONS

(71) Applicant: GanD, Inc., Miami Beach, FL (US)

(72) Inventors: Douglas Tadaki, Miami Beach, FL (US); David Steed, Pittsburgh, PA (US); Peta J. O'Connell, Mawson (AU)

(73) Assignee: GanD, Inc., Miami Beach, FL (US)

( * ) Notice: Subject to any disclaimer, the term of this patent is extended or adjusted under 35 U.S.C. 154(b) by 0 days.

(21) Appl. No.: 18/612,793

(22) Filed: Mar. 21, 2024

(51) Int. Cl.
| A61K 31/198 | (2006.01) |
| A61K 9/00 | (2006.01) |
| A61K 31/185 | (2006.01) |
| A61K 31/19 | (2006.01) |
| A61K 31/194 | (2006.01) |
| A61K 31/375 | (2006.01) |
| A61K 31/405 | (2006.01) |
| A61K 31/4172 | (2006.01) |
| A61K 31/7004 | (2006.01) |
| A61K 33/00 | (2006.01) |
| A61K 33/06 | (2006.01) |
| A61K 33/30 | (2006.01) |
| A61K 33/34 | (2006.01) |
| A61K 33/42 | (2006.01) |
| A61P 9/14 | (2006.01) |

(52) U.S. Cl.
CPC .......... *A61K 31/198* (2013.01); *A61K 9/0019* (2013.01); *A61K 31/185* (2013.01); *A61K 31/19* (2013.01); *A61K 31/194* (2013.01); *A61K 31/375* (2013.01); *A61K 31/405* (2013.01); *A61K 31/4172* (2013.01); *A61K 31/7004* (2013.01); *A61K 33/00* (2013.01); *A61K 33/06* (2013.01); *A61K 33/30* (2013.01); *A61K 33/34* (2013.01); *A61K 33/42* (2013.01); *A61P 9/14* (2018.01)

(58) Field of Classification Search
None
See application file for complete search history.

(56) References Cited

U.S. PATENT DOCUMENTS

| 5,443,848 | A | 8/1995 | Kramer et al. |
| 5,702,880 | A | 12/1997 | Segall et al. |
| 5,747,071 | A | 5/1998 | Segall et al. |
| 6,110,504 | A | 8/2000 | Segall et al. |
| 7,754,247 | B2 | 7/2010 | Fann et al. |
| 7,871,632 | B2 | 1/2011 | Chen |
| 8,063,020 | B2 | 11/2011 | Simpkins |
| 8,148,356 | B2 | 4/2012 | Pavliv |
| 8,236,863 | B2 | 8/2012 | Schmidt et al. |
| 8,563,233 | B2 | 10/2013 | Thatte |
| 8,569,236 | B2 | 10/2013 | Simpkins |
| 8,906,855 | B2 | 12/2014 | Simpkins |
| 9,387,162 | B2 | 7/2016 | Simpkins |
| 9,622,968 | B2 | 4/2017 | Simpkins |
| 10,039,276 | B2 | 8/2018 | Hassanein et al. |
| 10,172,949 | B2 | 1/2019 | Abuchowski et al. |
| 10,300,029 | B2 | 5/2019 | Mangino |
| 11,013,684 | B2 | 5/2021 | Rees |
| 2002/0144946 | A1 | 10/2002 | Drauz et al. |
| 2005/0031707 | A1 | 2/2005 | Schmidt et al. |
| 2005/0288235 | A1 | 12/2005 | Zhao |
| 2006/0211631 | A1 | 9/2006 | Mitsumoto et al. |
| 2009/0324748 | A1 | 12/2009 | Dobson |
| 2010/0166885 | A1 | 7/2010 | Fann et al. |
| 2010/0196461 | A1 | 8/2010 | Simpkins |
| 2011/0091863 | A1 | 4/2011 | Thatte |
| 2011/0257090 | A1 | 10/2011 | Breiter |
| 2011/0300193 | A1 | 12/2011 | Van Dyke |
| 2012/0172781 | A1 | 7/2012 | Wang |
| 2016/0081328 | A1 | 3/2016 | Thatte |
| 2023/0241184 | A1 | 8/2023 | Light, III |
| 2025/0041302 | A1 | 2/2025 | Ross et al. |

FOREIGN PATENT DOCUMENTS

| CN | 101 912 394 A | 12/2010 | |
| EP | 1 062 879 B1 | 8/2003 | |
| EP | 2135604 A1 * | 12/2009 | ........... A23L 1/3051 |
| EP | 2 567 700 A1 | 3/2013 | |
| JP | H0959150 A | 3/1997 | |
| JP | 2007-56013 A | 3/2007 | |
| JP | S5916817 B2 | 5/2016 | |
| WO | 2016022554 A1 | 2/2016 | |
| WO | 2018/015531 A1 | 1/2018 | |
| WO | 2022/019662 A1 | 1/2022 | |
| WO | 2023091642 A1 | 5/2023 | |
| WO | 2025038671 A2 | 2/2025 | |

OTHER PUBLICATIONS

Parson et al. (W. Drukker et al. (eds.), Replacement of Renal Function by Dialysis © Martinus Nijhoff Publishers bv, The Hague 1979).*
Wills (Biochemical Basis of Medicine, 1985).*
Arora et al., "Paracentesis-Induced Circulatory Dysfunction With Modest-Volume Paracentesis Is Partly Ameliorated by Albumin Insusion in Acute-on-Chronic Liver Failure," Heptology, vol. 72, No. 3, 2020, pp. 1043-1055.
ATSDR—Apr. 2022—Toxicological Profile for Copper (draft), U.S. Department of Health and Human Services, Agency for Toxic Substances and Disease Registry, pp. 1-362.
Boullata et al., "Parenteral nutrition compatibility and stability: A comprehensive review," JPEN J Parenter Enteral Nutr. 2022,46:273-299.
Butorov, "Relationship between plasma l-lysine concentrations and levels of HIV-1 RNA," Virulence 4:7, 646-653; Oct. 1, 2023.
Society of Critical Care Medicine, "Drug Shortage Alert Albumin," Sep. 2023, pp. 1-9.
Simonetti et al., "Plasma expanders for people with cirrhosis and large ascites treated with abdonimal paracentesis (Review)," Cochrane Database of Sytematic Reviews 2019, Issue 6. Art No. CD004039, DPI: 10.1002/14651858. CD004039.pub2.

(Continued)

Primary Examiner — Bong-Sook Baek
(74) Attorney, Agent, or Firm — THE MARBURY LAW GROUP, PLLC

(57) ABSTRACT

This disclosure relates to bioactive fluid compositions and methods of using the compositions. The bioactive fluid compositions can be used for intravenous administration in place of conventional crystalloid fluid compositions.

10 Claims, 11 Drawing Sheets

(56) References Cited

OTHER PUBLICATIONS

Hyzer et al., "Mechanistic Studies of the N-formylation of Edivoxetine, a Secondary Amine-Containing Drug, in a Solid Oral Dosage Form," Journal of Pharmaceutical Sciences 106 (2017), pp. 1218-1238.

Ishida, et al., "Genotoxicity and subchronic oral toxicity of L-ornithine monohydrochloride," Regulatory Toxicology and Pharmacology 67 (2013), pp. 360-371.

Kovalska et al., "Methionine Diet Evoked Hyperhomocysteinemia Causes Hippocampal Alterations, Metabolomics Plasma Changes and Behavioral Pattern in Wild Tupe Rats," Int. J. Mol. Sci. 2021, 22, 4961. https://doi.org/10.3390/ijms22094961.

Kumar et al., "Compensated liver cirrhosis: Natural course and disease-modifying strategies," World J. Methodol Sep. 20, 2023; 13(4):179-193.

Levine, "Methionine residues as endogenous antioxidants in proteins," Proc. Natl. Acad. Sci. USA, vol. 93, pp. 15036-15040, Dec. 1996, Biochemistry, pp. 15036-15040.

Levitt et al., "A model of blood-ammonia homeostasis based on a quantitative analysis of nitrogen metabolism in the multiple organs involved in the production, catabolismand excretion of ammonia in humans," Clinical and Experimental Gastroenterology 2018:11, pp. 193-215.

Levitt et al., "Use of Quantitative Modelling To Elucidate The Roles Of The Liver, Gut, Kidney, and Muscle In Ammonia Homeostasis And How Lactulose And Rifaximin Alter This Homeostasis," International Journal of General Medicien, 2019:12, pp. 367-380.

Fevre et al., "Quantifying methionine sulfoxide in therapeutic protein formulation excipients as sensitive oxidation marker," Journal of Chromatography B, 1189 (2022) 123092.

Li et al., "Association between methionine sulfoxide and risk of moyamoya disease," Frontiers in Neuroscience, Apr. 12, 2023, pp. 1-14.

Lüneburg et al., "Reference Intervals for Plasma L-Arginine and the L-Arginine: Asymmetric Dimethylarginine Ratio in the Framingham Offspring Cohort," J. Nutr. 141:2011, pp. 2186-2190.

Macken, "Randomised clinical trial: palliative long-term abdominal drains vs large-volume paracentesis in refractory ascites due to cirrhosis," University of Plymouth, Jul. 2020, pp. 1-36.

Final Report on the Safety Assessment of Malic Acid and Sodium Malate, International Journal of Toxicology, 20 (Suppl. 1):2001, pp. 47-55.

Mohiuddin et al., "Biochemistry, Ammonia," NCBI Bookshelf. A service of the National Library of Medicine, National Institutes of Health, StatPearls [Internet]. Treasure Island (FL): StatPearls Publishing; Jan. 2024, 4 pages.

Nagamani et al., "Argininosuccinate Lyase Deficiency," National Center for Biotechnology Information, Feb. 3, 2011; Updated Mar. 28, 2019, 21 pages.

Neijenhuis, "Development and Validation of a Disease-Specific Questionnaire to Assess Patient-Reported Symptoms in Polycystic Liver Disease," Hepatology, vol. 64, No. 1, 2016, pp. 151-160.

Neijenhuis et al., Supplement to Development and Validation of a Disease Specific Questionnair to Assess Symptoms in Polycystic Liver Disease, 2015, 16 pages.

Parsons et al., "7 The Composition of Dialysis Fluid," Replacement of Renal Function by Dialysis, 1979, pp. 148-170.

Parsons et al., "9 The Composition of Dialysis Fluid," 22 pages.

Rössle et al., "TIPS for the treatment of refractory ascites, hepatorenal syndrom and hepatic hydrothorax: a critical update," Gut 2010:59, pp. 988-1000. doi10.1136/gut.2009.193227.

Smith et al., "Distributive Shock," NCBI Bookshelf. A service of the National Library of Medicine, National Institutes of Health. StatPearls [Internet]. Treasure Island (FL): StatPearls Publishing, 2023, 6 pages.

Stadtman et al., "Methionine oxidation and aging," Biochimica et Biophysica Acta, 1703 (2005), pp. 135-140.

Ukor et al., "The haemodynamic effects of bolus versus slower infusion of intravenous crystalloid in healthy volunteers," Journal of Critical Care, 41 (2017), pp. 254-259.

Unger et al., "Stability and assessment of amino acids in parenternal nutrition solutions," Journal of Pharmaceutical and Biomedical Analysis, 147 (2018), pp. 125-139.

Van Hove et al., "Nonketotic Hyperglycinemia," U.S. National Library of Medicine, 2002, pp. 1-28.

Wong et al., "Improvement in Quality of Life and Decrease in Large-Volume Paracentesis Requirements With the Automated Low-Flow Ascites Pump," Liver Transplantation 26, pp. 651-661, 2020 AASLD.

Wong et al., Supplementary Table 1: Change in serum albumin during the study period, 2020, 1 page.

Wong et al., Supplementary Table 2: Pre-Implant Paracentesis Volume/Frequency in Subjects With/Without Post-Implant Paracentesis, 2020, 1 page.

New Acetadote Labeling Oct. 25, 2019.

Perel, et al., "Colloid versus crystalloid for fluid resuscitation in crtically ill patients," Cochrane Database of Systematic Review, Issue 2, Article CD000567 (2011).

Phillips, et al., Resuscitation of haemorrhagic shock with normal saline vs. lactated Ringer's: effects of oxygenation, extravascular lung water and haemodynamics, Critical Care 13, Article No. 30 (Mar. 4, 2009).

Schleithoff, et al., "Vitamin D supplementation improves cytokine profiles in patients with congestive heart failure: a double-blind, randomized, placebo-controlled trial," American Journal of Clinical Nutrition, vol. 83, Issue 4, pp. 754-759 (Apr. 2006).

Tahan, et al., "Vitamin E has a dual effect on anti-inflammatory and antioxidant activities in acetic acid-induced ulcerative colitis in rats," Canadian Journal of Survery, vol. 54, No. 5, pp. 333-338 (Oct. 2011).

Trevithick, et al., Reduction of sunburn damage to skin by topical application of vitamin E acetate following exposure to ultraviolet B radiation: effect of delaying application or of reducing concentration of Vitamin E acetate applied, Scanning Microscopy, vol. 7, No. 4, Article 17, pp. 1269-1281 (1993).

Nelson, S. J., et al., "Metabolic Imaging of Patients with Prostate Cancer Using Hyperpolarized [1-13C] Pyruvate," Science Translational Medicine, vol. 5, Issue 198 (Aug. 14, 2013).

Nolan, J., "Fluid replacement," British Medical Bulletin, vol. 55, Issue 4, pp. 821-843 (1999).

Norber, A, M.D., "Population Volume Kinetics Predicts Retention of 0.9% Saline Infused in Awake and Isoflurane-anesthetized Volunteers," Anesthesiology, vol. 107, pp. 24-32 (2007).

Nugent, K., et al., "Hyperglycemia and outcomes in patients with sepsis," Journal of Thoracic Disease, vol. 8, No. 7, pp. E575-E577 (2016).

Oda, S., et al., "Safety studies of L-alanyl-L-glutamine (I-AG)," Regulatory Toxicology and Pharmacology, vol. 50, pp. 226-238 (2008).

Osredkar, et al., "Copper and Zinc, Biological Role and Significance of Copper/Zinc Imbalance," Clinical Toxicology, Heavy Metal Toxicity, vol. S, p. 3 (2011).

Peltz, E.D., D.O., et al., "Pathologic Metabolism: An Exploratory Study of the Plasma Metabolome of Critical Injury," Journal of Trauma and Acute Care Surgery, vol. 78, No. 4, pp. 742-751 (Apr. 2015).

Poon, R.T., et al., "Improving Perioperative Outcome Expands the Role of Hepatectomy in Management of Benign and Malignant Hepatobiliary Diseases," Annals of Surgery, vol. 240, No. 4, pp. 698-710 (Oct. 2004).

Preiser, J.C., et al., "Metabolic response to the stress of critical illness," British Journal of Anesthesia, vol. 113, No. 6, pp. 945-954 (2014).

Rasmussen, K.C., M.D., "Effect of perioperative crystalloid or colloid fluid therapy on hemorrhage, coagulation competence, and outcome, A systematic review and stratified meta-analysis," Medicine (Baltimore), vol. 95, No. 31, p. e4498 (Aug. 2016).

Reddy, S., et al., "Crystalloid fluid therapy," Critical Care, vol. 220, p. 59 (2016).

(56) References Cited

OTHER PUBLICATIONS

Reichter R.P., et al., "Glycocalyx Gone Awry: Pathologic Cell Signaling during Endotheliopathy," American Journal of Biomedical Science and Research, vol. 5, Issue 2, pp. 118-126 (2019).
Reitsma, S., et al., "The endothelial glycocalyx: composition, functions, and visualization," Pflugers Archive—European Journal of Physiology, vol. 454, Issue 3, pp. 345-359 (2007).
Runyon, B. A., "Introduction to the Revised American Association for the Study of Liver Disease Practice Guideline Management of Adult Patients with Ascites Due to Cirrhosis 2012," Hepatology, vol. 57, No. 4, pp. 1651-1653 (Apr. 2013).
Russell, M.D., et al., "Effect of crystalloid infusion on hematocrit and intravascular volume in healthy, nonbleeding subjects," Annals of Emergency Medicine vol. 18, Issue 1, pp. 51-55 (1989).
Samonakis, D. N., et al., "Clinical outcomes of compensated and decompensated cirrhosis: A long term study," World Journal of Hepatology, vol. 6, Issue 7, pp. 504-512 (Jul. 27, 2014).
Schiesel, S., et al., "Quantitative high-performance liquid chromatography-tandem mass spectrometry impurity profiling methods for the analysis of parenteral infusion solutions for amino acid supplementation containing L-alanyl-L-glutamine," Journal of Chromatography A., vol. 1259, pp. 111-120 (2012).
Schott U., et al., "The endothelial glycocalyx and its disruption, protection and regeneration: a narrative review," Scandinavian Journal of Trauma, Resuscitation and Emergency Medicine, vol. 24, Article No. 48 (2016).
Self, W.H., et al., Balanced Crystalloids versus Saline in Noncritically Ill Adults, the New England Journal of Medicine, vol. 378, No. 9, pp. 819-828 (Mar. 1, 2018).
Semler, M.W., M.D., "Balanced Crystalloids versus Saline in Critically Ill Adults," The New England Journal of Medicine, vol. 378, Issue 9, pp. 829-839 (2018).
Shaw, A., et al. "Major Complications, Mortality, and Resource Utilization After Open Abdominal Surgery 0.9% Saline Compared to Plasma-lyte," Annals of Surgery, vol. 255, Issue 5, pp. 821-829 (May 2012).
Sohn, M., et al., "Ammonia Generation during Thermal Degradation of Amino Acids," Journal of Agricultural and Food Chemistry, vol. 43, No. 12, pp. 3001-3003 (Dec. 1995).
Sperry, J.L., M.D., et al., "Early Hyperglycemia Predicts Multiple Organ Failure and Mortality but Not Infection," The Journal Trauma: Injury, Infection and Critical Care, vol. 63, No. 3, pp. 487-494 (Sep. 2007).
Taghavi, S., et al., "Hypovolemic Shock," StatPearls, Treasure Island, FL [online] https://www.ncbi.nlm.nih.gov/ books/ NBK513297/ (Jan. 2022).
Tan, I., PhD, et al., "Plasma and Urine Amino Acid Profiles in a Healthy Adult Population of Singapore," Annals of the Academy of Medicine, Singapore, vol. 35, No. 7, pp. 468-475 (2006).
Taylor, W.M., Journal of Special Operations Medicine, vol. 9, Issue 2, pp. 13-21 (Spring 2009).
Tollofsrud, S., M.D., et al., "The Dynamics of Vascular vol. and Fluid Shifts of Lactated Ringer's Solution and Hypertonic-Saline-Dextran Solutions Infused in Normovolemic Sheep," Anesthesia & Analgesia, vol. 93, Issue 4, pp. 823-831 (2001).
Torres, L.N., et al., "Low-volume resuscitation with normal saline is associated with microvascular endothelial dysfunction after hemorrhage in rats, compared to colloids and balanced crystalloids," Critical Care, vol. 21, No. 1, p. 160 (Jun. 29, 2017).
Torres, L.N., PhD, et al., "Evaluation of resuscitation fluids on endothelial glycocalyx venular blood flow, and coagulation function after hemorrhagic shock in rats," Journal of Trauma Acute Care Surgery, vol. 75, No. 5, pp. 759-766 (Nov. 2013).
Turner, P. V., et al., "Administration of Substances to Laboratory Animals: Routes of Administration and Factors to Consider," Journal of the American Association for Laboratory Animal Science, vol. 50, No. 5, pp. 600-613 (Sep. 2011).

Ueyama, H., et al., "Effects of Crystalloid and Colloid Preload on Blood Volume in the Parturient Undergoing Spinal Anesthesia for Elective Cesarean Section," Anesthesiology, vol. 91, pp. 1571-1576 (1999).
Wallace, H.A., et al., "Fluid Resuscitation," StatPearls, Treasure Island, FL, Last Updated: Jul. 27, 2021, [online [ https://www.ncbi. nlm.nih.gov/books/NBK534791/ (2021).
Wang, P., et al., "Hemorrhage Produces Depression in Microvascular Blood Flow Which Persists Despite Fluid Resuscitation," Circulatory Shock, vol. 32, No. 4, pp. 307-318 (Dec. 1, 1990).
Weissman, C., M.D., "The Metabolic Response to Stress: An Overview and Update," Anesthesiology, vol. 73, No. 2, pp. 308-327 (Aug. 1990).
Wiggans, M.G., et al., "Serum arterial lactate concentration predicts mortality and organ dysfunction following liver resection," Perioperative Medicine 2, Article No. 21 (Oct. 7, 2013).
Wise,, R., et al., "Strategies for Intravenous Fluid Resuscitation in Trauma Patients," World Journal of Surgery, vol. 41, pp. 1170-1183 (Jan. 5, 2017).
Wlodek, L., et al., "Formation of 2-Methyl-2,4-Thiazolidinedicarboxylic Acid From L-Cysteine in Rat Tissues," Acta Biochimica Polonica, vol. 31, No. 3, pp. 279-288 (1984).
Yailian, A., et al., "Production and stability of a hospital parenteral nutrition solution for neonates," Journal of Pharmaceutical Analysis, vol. 9, pp. 83-90 (2019).
Berger, et al., "Influence of early antioxidant supplements on clinical evolution and organ function in critcally ill cardiac surgery, major trauma, and suarachnoid hemorrhage patients," Critical Care, vol. 12, Article No. R101 (Aug. 7, 2008).
Eastridge, et al., "Died of wounds on the battlefield: causation and implications for improving combat casualty care," The Journal of Trauma: Injury, Infection, and Critical Care, vol. 71, Supplement 1, pp. S4-S8 (Jul. 2011).
Felemovicius, et al., "Intestinal radioprotection by vitamin E (alpha-tocopherol)," Annals of Surgery, vol. 222, No. 4, pp. 504-510 (1995).
Griffin, et al., "Vitamin D and its analogs as regulators of immune activation and antigen presentation," Annals Review of Nutrition, vol. 23, pp. 117-145 (Mar. 19, 2003).
Heckbert, et al., "Outcome after Hemorrhagic shock in trauma patents," Journal of Trauma, vol. 45, Issue 3, pp. 545-549.
Horton, J.W., "Free radicals and lipid peroxidation mediated injury in burn trauma; the role of antioxidant therapy," Toxicology, vol. 189, Issues 1-2) pp. 75-88 (Jul. 15, 2003).
Inci, et al., "Time-Level Relationship for Lipid Peroxidation and the Protective Effect of a-Tocopherol in Experimental Mild and Severe Brain Injury," Neurosurgery, vol. 43, Issue 2, pp. 330-335 (Aug. 1998).
Jiang, Q., Natural forms of vitamin E: metabolism, antioxidant, and anti-inflammatory activities and their role in disease prevention and tharapy, Free Radical Biology and Medicine, vol. 72, pp. 76-90 (Jul. 2014).
Kaur, et al., "Transfusion protocol in trauma," Journal of Emergencies, Trauma and Shock, vol. 4, Issue 1, pp. 103-108 (Jan.-Mar. 2011).
Kulklarni, et al., "Gamma-Tocotrienol Protects Hematopoietic Stem and Progenitor Cells in Mice after Total-Body Irradiation," Radiation Research, vol. 173, No. 6, pp. 738-747 (2010).
Letson, et al., "Unexpected 100% Survial Following 60% Blood Loss Using Small-Volume 7.5% NaCl With Adenocain and Mg2+ in the Rat Model of Extreme Hemorrhagic Shock," Shock, vol. 36, No. 6, pp. 586-594 (2011).
Liu, et al., "Toll-Like Receptor Triggering of a Vitamin D-Mediated Human Antimicrobial Response," Science, vol. 311, No. 5768, pp. 1770-1773 (Mar. 26, 2006).
Aldecoa, C., et al., "Role of albumin in the preservation of endothelial glycocalyx integrity and the microcirculation: a review," Annals of Intensive Care, vol. 10, No. 85 (2020).
Barbosa, et al., "Metabolic effects of L-alanyl-glutamine in burned rats," Elsevier, Burns vol. 32, pp. 721-727 (2006).
Bareli, S, et al., Frontiers in Medicine, vol. 5, p. 91 (2018).
Bar-Or, D., et al., Frontiers in Medicine, vol. 6, p. 54 (2019).
Bermejo-Martin, J.F., et al., Journal of Clinical Medicine, vol. 7, pp. 400-414, (2018).

(56) References Cited

OTHER PUBLICATIONS

Bihari, S., et al., "Bolus intravenous 0.9% saline, but not 4% albumin or 5% glucose, causes interstitial pulmonary edema in healthy subjects," Journal of Applied Physiology, vol. 119, pp. 783-792 (2015).

Biggins, et al., "Diagnosis, Evaluation, and Management of Ascites, Spontaneous Bacterial Peritonitis and Hepatorenal Syndrome: 2021 Practice Guidance by the American Association for the Study of Liver Diseases," Hepatology, vol. 74, No. 2 (2021).

Boldt, J., et al., "The impact of fluid therapy on microcirculation and tissue oxygenation in hypovolemic patients: a review," Intensive Care Medicine, vol. 36, Issue 8, pp. 1299-1308 (May 26, 2010).

Bosboom, J. J., et al., "Transfusion-Associated Circulatory Overload: A Clinical Perspective," Transfusion Medicine Reviews, vol. 33, pp. 69-77 (2019).

Cannon, J.W., "Hemorrhagic Shock," The New England Journal of Medicine, vol. 378, Issue 4, pp. 370-379 (2018).

Cartotto, R., et al., Journal of Burn Care and Rehabilitation, vol. 24, Issue 2, pp. 75-84 (2003).

Chiejina, M., et al., "Ascites," StatPearls, Treasure Island, FL, Updated Aug. 8, 2023, [online] https://www.ncbi.nlm.nih.gov/books/NBK470482/.

Correa-Gallego, C., Md, "Goal-Directed Fluid Therapy using Stroke Volume Variation for Resuscitation after Low Central Venous Pressure Assisted Liver Resection. A Randomized Clinical Trial," Journal of American College of Surgeons, vol. 221, Issue 2, pp. 591-601 (Aug. 2015).

Cotton, B.A., et al., "The Cellular, Metabolic, and Systemic Consequences of Aggressive Fluid Resuscitation Strategies," Shock, vol. 26, Issue 2, pp. 115-121 (2006).

D'Alesandro, A., et al., "Plasma first resuscitation reduces lactate acidosis, enhances redox homeostasis, amino acid and purine catabolismin a rat model of profound hemorrhagic shock," Shock, vol. 46, Issue 2, pp. 173-182 (Aug. 2016).

De Boer, M., "Impact of Blood Loss on Outcome after Liver Resection," Digestive Surgery, vol. 24, Issue 4, pp. 259-264 (Jul. 27, 2007).

Dickson, et al., South African Medical Journal, vol. 57, Issue 19, pp. 785-787 (May 10, 1980).

Dobson, G.P., et al., Journal of the Royal Army Medical Corps, vol. 160, Issue 1, pp. 9-15 (2014).

Drummer, C., et al., "Effects of an acute saline infusion on fluid and electrolyte metabolism in humans," American Journal of Physiology—Renal Physiology, vol. 262, Issue 5, pp. F744-F754 (May 1, 1992).

European Association for the Study of the Liver, "EASL clinical practice guidelines on the management of ascites, spontaneous bacterial peritonitis, and hepatorenal syndrome in cirrhosis," Journal of Hepatology, vol. 53, pp. 397-417 (2010).

Finfer, S, et al., Nature Reviews Nephrology, Issue 11, p. 717 (Nov. 2018).

Finfer, s., et al., "Intravenous fluid therapy in critically ill adults," Nature Reviews Nephrology, vol. 14, Issue 9, pp. 541-557 (Sep. 2018).

Funk, W., et al., "Microcirculatory Perfusion during Volume Therapy, A comparative Study Using Crystalloid or Colloid in Awake Animals," Anesthesiology, vol. 82, No. 4, pp. 975-982 (Apr. 1995).

Gardner, D.K., et al., "Amino Acids and Ammonium Regulate Mouse Embryo Development in Culture," Biology of Reproduction, vol. 48, pp. 377-385 (1993).

Gines, P., et al., "Comparison of Paracentesis and Diuretics in the Treatment of Cirrhotics with Tense Ascites, Results of a Randomized Study, Results of a Randomized Study" Gastroenterology, vol. 93, pp. 234-241 (Aug. 1987).

Gutierrez, G., et al., "Clinical review: Hemorrhagic shock," Critical Care, vol. 8, pp. 373-381 (Apr. 2, 2004).

Guven, G., et al., "Microcirculation: Physiology, Pathophysiology and Clinical Application," Blood Purification, vol. 49, pp. 143-150 (2020).

Hahn, R.G., "Adverse effects of crystalloid and colloid fluids," Anesthesiology Intensive Therapy, vol. 49, No. 4, pp. 1-6 (2017).

Hahn, R.G., et al., "The half-life of infusion fluids," European Journal of Anesthesiology, vol. 33, Issue 7, pp. 475-482 (2016).

Hasenboehler, E., et al., "Metabolic changes after polytrauma: an imperative for early nutritional support," World Journal of Emergency Surgery, vol. 1, Issue 29 (Oct. 4, 2006).

He, H., et al., "Colloids and the Microcirculation," Anesthesia and Analgesia, vol. 126, No. 5, pp. 1747-1754 (May 2018).

Heughan, C., et al., "Effect of Excessive Infusion of Saline Solution on Tissue Oxygen Transport," Surgery, Gynecology & Obstetrics, vol. 135, Issue 2, pp. 257-260 (Aug. 1972).

Holte, K., MD, "Physiologic Effects of the Intravenous Fluid Administration in Healthy Volunteers," Anesthesia & Analgesia, vol. 96, pp. 1504-1509 (2003).

Ince, C., et al., Shock, vol. 45, Issue 3, pp. 259-270 (2016).

Ingalls, N., MD, "A Review of the First 10 Years of Critical Care Aeromedical Transport During Operation Iraqi Freedom and Operation Enduring Freedom, The Importance of Evacuation Timing," JAMA Surgery, vol. 149, Issue 8, pp. 807-813 (2014).

Jacob, M., et al., "The intravascular volume effect of Ringer's lactate is below 20%: a prospective study in humans," Critical Care 16, Article R86 (2012).

Jarnagin, W.R., MD, "Improvement in Perioperative Outcome After Hepatic Resection, Analysis of 1,803 Consecutive Cases Over the Past Decade," Annals of Surgery, vol. 236, No. 4, pp. 397-407 (Oct. 2002).

Johansson, P., et al., Critical Care 21, Article No. 25, pp. 25-31 (2017).

Kincaid, E.H., et al., "Elevated Arterial Base Deficit in Trauma Patients: A Marker of Impaired Oxygen Utilization," Journal of American College of Surgeons, vol. 187, Issue 4, pp. 384-392 (Oct. 1998).

Kleijkers, S., "Ammonium accumulation in commercially available embryo culture media and protein supplements during storage at 2-8° C. and during incubation at 37° C.," Human Reproduction, vol. 3, No. 6, pp. 1192-1199 (2016).

Kraut, J.A., et al., "Treatment of acute non-anion gap metabolic acidosis," Clinical Kidney Journal, vol. 8, Issue 1, pp. 93-99 (2014).

Kruger-Genge, et al., "Vascular Endothelial Cell Biology: An Update," International Journal of Molecular Sciences, vol. 20, Issue 18, p. 4411 ( Sep. 7, 2019).

Lozano, R., et al., "Global and regional mortality from 235 causes of death for 20 age-groups in 1990 and 2010: A systematic analysis," Lancet, vol. 380, Issue 9859, pp. 2095-2128 (Dec. 15, 2012).

McNally, S. J., et al., "Factors in perioperative care that determine blood loss in liver surgery," International Hepato-Pancreato-Billary Association, vol. 14, pp. 236-241 (2012).

Milford, E. M., et al., "Resuscitation Fluid Choices to Preserve the Endothelial Glycocalyx," Critical Care 23, Article No. 77 (Mar. 9, 2019).

Miller, T.E., et al., Perioperative Fluid Therapy for Major Surgery, Clinical Focus Review, Anesthesiology, vol. 130, No. 5, pp. 825-832 (May 2019).

Mitra, B, et al., "Long-Term Outcomes of Patients Receiving a Massive Transfusion After Trauma," Shock, vol. 42, No. 4, pp. 307-312 (2014).

Moreau, R., et al., "Clinical characteristics and outcome of patients with cirrhosis and refractory ascites," Liver International, vol. 24, pp. 457-464 (2004).

Mutter, T.C., et al., "Hydroxyethyl starch (HES) versus other fluid therapies: effects on kidney function (Review)," Cochrane Database of Systematic Reviews, Issue 7, Article No. CDO7594 (2013).

Myles, P. S., et al., "Restrictive versus Liberal Fluid Therapy for Major Abdominal Surgery," The New England Journal of Medicine, vol. 378, No. 24, pp. 2263-2274 (Jun. 14, 2018).

International Search Report and the Written Opinion of the International Searching Authority in PCT/US2025/020899 dated May 23, 2025.

International Search Report and the Written Opinion of the International Searching Authority in PCT/US2025/020879 dated Jun. 27, 2025.

(56) References Cited

OTHER PUBLICATIONS

Schwalb, et al., "The Effect of amino acids on the ischemic heart", Journal of Thoracic and Cardiovascular Surgery, pp. 551-556, XP093288265 (Oct. 1, 1989).

* cited by examiner

Sham control (LPS + Surgery + Fluorescent Albumin but no intravenous fluids)

Normal Saline (LPS + Surgery + Fluorescent Albumin + Intravenous NS)

1A: Animal #1 (LPS + Surgery + Fluorescent Albumin + Intravenous GND)

BIOACTIVE FLUID COMPOSITIONS

TECHNICAL FIELD

The disclosure relates to methods and resuscitative and supportive bioactive fluid compositions that promote endothelial cell integrity.

BACKGROUND

Crystalloid fluids such as Normal Saline (NS) and Lactated Ringer's solution (LR) have long been considered the standard of care for intravenous (IV) fluid replacement in the case of blood volume loss, shock, and other serious injuries and illness, or as carriers for the delivery of nutrients, therapeutics, or diagnostics. The goal of IV fluid therapy is to increase blood volume and raise blood pressure to enable effective circulation of blood and oxygen to the organs and tissues. Intravenous infusion of crystalloid fluid produces an increase in blood volume and blood pressure, but these beneficial effects are short-lived. Globally, the most frequently used crystalloid IV fluid is NS (0.9% w/v NaCl), which has been used as the primary resuscitation fluid for over 130 years.

In the case of blood volume loss and/or shock, IV therapy with crystalloid fluids is the first line of treatment. Preclinical and clinical studies using normal subjects report that IV infusion of crystalloid fluids produces a transient increase in blood volume. But studies show that only 20-40% of infused crystalloid fluid remains within the intravascular compartment after 20-60 minutes. As a result, the amount of crystalloid fluid required to restore intravascular volume is calculated to be around 3-4 times that of the actual blood volume lost. However, infusion of large volumes of crystalloid fluid results in excessive hemodilution and the depletion of energy stores and metabolites. The fluid extravasates from the vasculature and accumulates in the surrounding tissues. While this fluid is eventually excreted, this process can take from several days up to three weeks. In addition, the high concentration of chloride in crystalloid fluids such as NS exacerbates vascular leakage and reduces the volume replacement effect of the fluid.

While IV infusion of crystalloid fluids produces a transient increase in blood pressure and blood volume which restores central perfusion to critical major organs including the brain, heart and lungs, there is evidence that microcirculation and peripheral tissue oxygen perfusion remain impaired. Animal models of hypovolemic shock show that infusion of crystalloid fluids is associated with decreased blood flow and a decreased density of functional capillaries. Crystalloid-induced edema also increases the oxygen diffusion distance. Oxygen is poorly soluble in aqueous solutions and the large volume of crystalloid fluid used to treat reduced blood volume leads to excessive dilution of circulating red blood cells which further reduces oxygen availability. The effects of crystalloid fluids combine to reduce oxygen transport and decrease its availability to peripheral tissues. A prolonged reduction or deprivation of oxygen impairs oxidative phosphorylation and can cause delayed wound healing, tissue damage, acute kidney injury, multi-organ failure, and even death.

In addition, NS can worsen hemorrhage-induced metabolic acidosis and, due to its high chloride content, can cause hyperchloremic acidosis. The adverse effects of acidosis include impaired renal and splanchnic function, and hypotension. In liver surgery, NS-induced hyperchloremia is associated with increased complications and morbidity.

To avoid the adverse effects of NS, other crystalloid solutions such as LR have been used. Lactated Ringer's solution has a lower concentration of chloride, contains other electrolytes such as potassium, calcium, and magnesium in concentrations similar to normal plasma, and contains buffers such as lactate that are rapidly metabolized to form bicarbonate which aids the correction of acidosis. This formulation should make LR a more effective IV fluid; however, elevated lactate concentration following liver surgery is associated with decreased liver function (as it is the primary organ for lactate metabolism) and increased complication rates and mortality. Increased lactate concentrations are also associated with hyperglycemia as lactate is involved in gluconeogenesis. Severe hyperglycemia is an indicator of poor outcomes for seriously ill or injured patients (increased morbidity and mortality), including those with hemorrhagic shock, sepsis, systemic inflammatory response syndrome, or traumatic brain injury, and this may be exacerbated by concomitant hyperlactemia. Multi-center clinical studies of non-critical and critically ill patients found that infusion of LR only resulted in a modest, albeit significant, 1% reduction in major adverse kidney events within 30 days of treatment compared to NS.

The negative effects of known standard-of-care crystalloid fluids may ultimately be due to the fact that they result in or exacerbate endothelial injury, for example causing damage to and/or death of vascular endothelial cells, and further increase fluid leak, tissue damage, and organ injury. The role played by vascular endothelial cells in the structure and function of the mammalian circulatory system is well documented. The vascular endothelium is a layer of endothelial cells lining the inner surface of blood vessels. These cells serve as a semi-permeable barrier between the blood and the surrounding tissues of the body, and they actively control the movement of fluid, solutes, macromolecules, and cells via endothelial cell junctions thereby maintaining homeostasis. The vascular endothelium also functions to protect the tissues from circulating microorganisms, regulate vascular tone and blood flow, and control blood coagulation and platelet function. In addition, vascular endothelial cells participate in the regulation of immune responses, inflammation, and angiogenesis.

Injury to the vascular endothelium can arise from many serious conditions including blood loss, ischemia-reperfusion, dehydration, sepsis, burns, hyperglycemia, and shock. Serious injury and/or illness can disrupt the integrity of the vascular endothelium and result in leakage of fluid from the vasculature via a process known as extravasation. Extravasated fluid accumulates in the surrounding tissues causing interstitial edema and, ultimately, secondary injury to kidneys, liver, intestines, and muscles.

Several studies have shown that vascular endothelial injury, including by IV fluids, commences at the cellular level. Injury to the blood vessels starts with the breakdown and shedding of the glycocalyx, a matrix of glycoproteins, proteoglycans, and glycolipids coating the vascular endothelium. The glycocalyx acts a protective barrier and functions to prevent vascular fluid leakage and to control the access of fluid, molecules, and cells to the vascular endothelium during homeostasis, inflammation, and coagulation. Glycocalyx injury is associated with a wide number of serious conditions, including ischemia-reperfusion injury, sepsis, burns, hemorrhage, hyperglycemia, and shock. The degree of endothelial glycocalyx degradation has been strongly associated with markers of clinical prognosis and subject outcomes. In trauma patients with comparable injury severity scores, high plasma concentrations of shed glycocalyx glycoprotein Syndecan-1 are associated with a several-fold increase in mortality.

Accordingly, treatment of conditions such as those described above with standard-of-care crystalloid fluids that result in or further exacerbate such conditions, either as a first line therapy or for supportive care, is of great concern. There is a long-felt and critical need for IV fluids that can replace current standard-of-care fluids that, at best, fail to maintain the integrity of endothelial cells and, at worst, exacerbate endothelial cell damage, resulting in increased vascular leakage and the resultant extravasation of intravascular fluid. However, finding a bioactive fluid composition that meets such need has been challenging.

SUMMARY

It has now been discovered that deficiencies of current crystalloid fluids can be prevented, lessened, or even ameliorated by adding certain components to such fluids. Fluid compositions according to the disclosure can promote the survival of endothelial cells, and, in some cases result in proliferation of such cells. As a result, various negative effects of current crystalloid fluids, such as extravasation, can be reduced or prevented. The fluid compositions according to the disclosure thus demonstrate significant improvement in various effects, compared to current standard-of-care IV fluids.

The fluid compositions, which may be referred to interchangeably as "bioactive fluid compositions," described herein are advantageous in that they support and enhance survival, recovery, and function of cells that have been subjected to various stresses such as hypoxia, starvation, or exposure to inflammatory factors. These bioactive fluid compositions also avoid the use of standard-of-care crystalloid fluids (e.g. NS or LR) that are detrimental to cells and which are required in large volumes that dilute circulating minerals, nutrients, and metabolites needed for cell survival, recovery, and function.

The bioactive fluid compositions according to the disclosure are capable of maintaining integrity of vascular endothelial cells, resulting in increased survival of seriously ill and/or injured subjects, improving physiological outcomes and tissue oxygen perfusion, and reducing extravasation. The compositions have been shown to result in better outcomes following acute blood volume loss, and during the recovery and repair phases of conditions such as those described above.

The bioactive fluid compositions can be used in place of standard-of-care crystalloid fluids, such as NS or LR, that fail to protect endothelial cells from injury and, in some cases, exacerbate endothelial cell injury. In resuscitative care situations in subjects that have experienced severe loss of extracellular fluid volume, including but not limited to, blood loss associated with hemorrhage such as traumatic hemorrhage, surgical blood loss, and postpartum hemorrhage, the bioactive fluid compositions can reverse metabolic acidosis, preserve tissue oxygen perfusion, and increase survival. In addition, the bioactive fluid compositions are useful for supportive care, for example to treat sepsis or dehydration, and their improved properties make them useful as carriers for the delivery of nutrients, therapeutics, and diagnostics.

The bioactive fluid compositions described herein are sterile formulations (also referred to herein as fluids or solutions) suitable for injection that contain nutrients, as well as vitamins and cofactors that have been shown to possess antioxidant and anti-inflammatory properties that result in increased cell viability and, in some instances, result in endothelial cell metabolism and proliferation as compared to standard-of-care solutions. In addition, the bioactive fluid compositions arrest leakage into the interstitial space (extravasation) seen with current standard-of-care fluids, thus leading to better flow and circulation of existing (remaining) red blood cells and their oxygen carrying capacity, thereby preserving microcirculation and functional capillary density and maintaining oxygen perfusion of peripheral tissues.

The bioactive fluid compositions according to the disclosure can be used as a volume replacement or as extenders for blood or blood products. The uses may include fluid replacement following traumatic and non-traumatic blood volume loss. In addition, the bioactive fluid compositions may be used as carriers for delivery of therapeutic, diagnostic, or other active agents, including nutritional products. In some embodiments, the bioactive fluid compositions described herein are free or essentially free of blood components or blood products, proteins, antibodies, immunoreactive substances, colloidal or oncotic substances, and/or oxygen-carriers. In some embodiments, the compositions can be supplied in concentrated or dry form suitable for reconstitution, thus making them easy to prepare, sterilize, and transport.

In various embodiments, the disclosure relates to fluid compositions, e.g. sterile bioactive fluid compositions, comprising (a) at least one amino acid chosen from serine, threonine, and/or derivatives thereof, (b) at least one additional component chosen from chloride, sodium, copper, zinc, magnesium, phosphate, potassium, acetate, pyruvate, malic acid, and/or derivatives thereof, and (c) a physiologically acceptable carrier fluid. Optionally, the compositions may be free or essentially free of blood and/or blood products. In various embodiments, the compositions are crystalloid fluids. The amount(s) of serine, threonine, and/or derivatives thereof may, for example, be within or near physiological levels. For example, the amount of serine may range from about 56-140 µmol/L and/or the amount of threonine may range from about 92-240 µmol/L. In some embodiments, the bioactive fluid compositions comprise (a) at least one amino acid chosen from serine, threonine, and/or derivatives thereof, wherein the amount(s) of serine, threonine, and/or derivatives thereof are within or near physiological levels, for example from about 56-140 µmol/L of serine and/or from about 92-240 µmol/L of threonine, (b) from about 95-115 mmol/L of chloride, from about 115-150 mmol/L of sodium, from about 5-24 µmol/L of copper, from about 15-70 µmol/L of zinc, from about 0.2-1.0 mmol/L of magnesium, from about 0.8-2 mmol/L of phosphate, from about 2-5 mmol/L of potassium, from about 2-45 mmol/L of acetate, from about 0.03-2.5 mmol/L of pyruvate, and/or from about 1-15 mmol/L of malic acid, and (c) a physiologically acceptable carrier fluid, e.g. water.

In some embodiments, the disclosure relates to fluid compositions, e.g. sterile bioactive fluid compositions, comprising (a) at least one amino acid chosen from serine, threonine, and/or derivatives thereof, (b) chloride, sodium, copper, zinc, magnesium, phosphate, potassium, acetate, pyruvate, and malic acid, and (c) a physiologically acceptable carrier fluid. Optionally, the compositions may be free or essentially free of blood and/or blood products. In various embodiments, the compositions are crystalloid fluids. The amount(s) of serine, threonine, and/or derivatives thereof may, for example, be within or near physiological levels. For example, the amount of serine may range from about 56-140

μmol/L and/or the amount of threonine may range from about 92-240 μmol/L. In some embodiments, the bioactive fluid compositions comprise (a) at least one amino acid chosen from serine, threonine, and/or derivatives thereof, wherein the amount(s) of serine, threonine, and/or derivatives thereof are within or near physiological levels, for example from about 56-140 μmol/L of serine and/or from about 92-240 μmol/L of threonine, (b) from about 95-115 mmol/L of chloride, from about 115-150 mmol/L of sodium, from about 5-24 μmol/L of copper, from about 15-70 μmol/L of zinc, from about 0.2-1.0 mmol/L of magnesium, from about 0.8-2 mmol/L of phosphate, from about 2-5 mmol/L of potassium, from about 2-45 mmol/L of acetate, from about 0.03-2.5 mmol/L of pyruvate, and from about 1-15 mmol/L of malic acid, and (c) a physiologically acceptable carrier fluid, e.g. water.

In various embodiments, the disclosure relates to fluid compositions, e.g. sterile bioactive fluid compositions, comprising (a) at least one amino acid chosen from serine, threonine, and/or derivatives thereof, (b) at least one additional component chosen from chloride, sodium, copper, zinc, magnesium, phosphate, potassium, acetate, pyruvate, malic acid, β-alanine, arginine, glutamine, ornithine, taurine, Vitamin C, glucose, and/or derivatives thereof, and (c) a physiologically acceptable carrier fluid. Optionally, the compositions may be free or essentially free of blood and/or blood products. In various embodiments, the compositions are crystalloid fluids. The amount(s) of serine, threonine, and/or derivatives thereof may, for example, be within or near physiological levels. For example, the amount of serine may range from about 56-140 μmol/L and/or the amount of threonine may range from about 92-240 μmol/L. In some embodiments, the bioactive fluid compositions comprise (a) at least one amino acid chosen from serine, threonine, and/or derivatives thereof, wherein the amount(s) of serine, threonine, and/or derivatives thereof are within or near physiological levels, for example from about 56-140 μmol/L of serine and/or from about 92-240 μmol/L of threonine, (b) from about 95-115 mmol/L of chloride, from about 115-150 mmol/L of sodium, from about 5-24 μmol/L of copper, from about 15-70 μmol/L of zinc, from about 0.2-1.0 mmol/L of magnesium, from about 0.8-2 mmol/L of phosphate, from about 2-5 mmol/L of potassium, from about 2-45 mmol/L of acetate, from about 0.03-2.5 mmol/L of pyruvate, from about 1-15 mmol/L of malic acid, from about 200-600 μmol/L of β-alanine, from about 10-70 μmol/L of arginine, from about 390-650 μmol/L of glutamine, from about 27-80 μmol/L of ornithine, from about 45-440 μmol/L of taurine, from about 11-120 μmol/L of Vitamin C, and/or from about 3-25 mmol/L of glucose, and (c) a physiologically acceptable carrier fluid, e.g. water.

In some embodiments, the disclosure relates to fluid compositions, e.g. sterile bioactive fluid compositions, comprising (a) at least one amino acid chosen from serine, threonine, and/or derivatives thereof, (b) chloride, sodium, copper, zinc, magnesium, phosphate, potassium, acetate, pyruvate, malic acid, β-alanine, arginine, glutamine, ornithine, taurine, Vitamin C, and glucose, and (c) a physiologically acceptable carrier fluid. Optionally, the compositions may be free or essentially free of blood and/or blood products. In various embodiments, the compositions are crystalloid fluids. The amount(s) of serine, threonine, and/or derivatives thereof may, for example, be within or near physiological levels. For example, the amount of serine may range from about 56-140 μmol/L and/or the amount of threonine may range from about 92-240 μmol/L. In some embodiments, the bioactive fluid compositions comprise (a) at least one amino acid chosen from serine, threonine, and/or derivatives thereof, wherein the amount(s) of serine, threonine, and/or derivatives thereof are within or near physiological levels, for example from about 56-140 mol/L of serine and/or from about 92-240 μmol/L of threonine, (b) from about 95-115 mmol/L of chloride, from about 115-150 mmol/L of sodium, from about 5-24 μmol/L of copper, from about 15-70 μmol/L of zinc, from about 0.2-1.0 mmol/L of magnesium, from about 0.8-2 mmol/L of phosphate, from about 2-5 mmol/L of potassium, from about 2-45 mmol/L of acetate, from about 0.03-2.5 mmol/L of pyruvate, from about 1-15 mmol/L of malic acid, from about 200-600 μmol/L of β-alanine, from about 10-70 μmol/L of arginine, from about 390-650 μmol/L of glutamine, from about 27-80 μmol/L of ornithine, from about 45-440 μmol/L of taurine, from about 11-120 μmol/L of Vitamin C, and from about 3-25 mmol/L of glucose, and (c) a physiologically acceptable carrier fluid, e.g. water.

In various embodiments, the disclosure relates to fluid compositions, e.g. sterile bioactive fluid compositions, comprising (a) means for preventing or reducing extravasation in a subject receiving or in need of receiving intravenous fluids, and (b) a physiologically acceptable carrier fluid. In other embodiments, the disclosure relates to fluid compositions, e.g. sterile bioactive fluid compositions, comprising (a) means for enabling survival and/or proliferation of stressed or damaged endothelial cells in a subject receiving or in need of receiving intravenous fluids, and (b) a physiologically acceptable carrier fluid. In other embodiments, the disclosure relates to fluid compositions, e.g. sterile bioactive fluid compositions, comprising (a) means for protecting and/or preserving vascular integrity in a subject receiving or in need of receiving intravenous fluids, and (b) a physiologically acceptable carrier fluid. In other embodiments, the disclosure relates to fluid compositions, e.g. sterile bioactive fluid compositions, comprising (a) means for administering a therapeutic, diagnostic, or active agent and/or reducing the effective dose or amount of a therapeutic, diagnostic, or active agent administered to a subject in need of such therapeutic, diagnostic, or active agent, and (b) a physiologically acceptable carrier fluid. In other embodiments, the disclosure relates to fluid compositions, e.g. sterile bioactive fluid compositions, comprising (a) means for preserving tissue oxygen perfusion in a subject receiving or in need of receiving intravenous fluids, and (b) a physiologically acceptable carrier fluid. In other embodiments, the disclosure relates to fluid compositions, e.g. sterile bioactive fluid compositions, comprising (a) means for improving and/or normalizing physiological and/or metabolic markers of clinical outcome, improving survival time, and/or reducing morbidity in a subject with serious injury and/or illness, for example traumatic injury, hemorrhage, and/or hemorrhagic shock, and (b) a physiologically acceptable carrier fluid.

In still further embodiments, the disclosure relates to improved crystalloid fluids, for example compared to NS. Thus, in some embodiments the disclosure relates to crystalloid fluids comprising sodium and chloride in water, the improvement comprising physiological levels of serine, threonine, and/or derivatives thereof. The composition may further comprise one or more additional components chosen from copper, zinc, magnesium, phosphate, potassium, acetate, pyruvate, malic acid, β-alanine, arginine, glutamine, ornithine, taurine, Vitamin C, glucose, and/or derivatives thereof. In exemplary embodiments, the disclosure relates to crystalloid fluids comprising sodium and chloride in water, the improvement comprising from about 56-140 μmol/L of serine and/or from about 92-240 μmol/L of threonine, and/or derivatives thereof, and optionally one or more additional components chosen from copper, zinc, magnesium, phosphate, potassium, acetate, pyruvate, malic acid, and/or derivatives thereof. In other exemplary embodiments, the disclosure relates to crystalloid fluids comprising sodium and chloride in water, the improvement comprising from about 56-140 µmol/L of serine and/or from about 92-240 µmol/L of threonine, and/or derivatives thereof, and optionally one or more additional components chosen from copper, zinc, magnesium, phosphate, potassium, acetate, pyruvate, malic acid, β-alanine, arginine, glutamine, ornithine, taurine, Vitamin C, glucose, and/or derivatives thereof.

In further embodiments, the disclosure relates to improved crystalloid fluids, for example compared to LR. Thus, in some embodiments the disclosure relates to crystalloid fluids comprising sodium, chloride, potassium, and calcium in water, the improvement comprising physiological levels of serine, threonine, and/or derivatives thereof. The composition may further comprise one or more additional components chosen from copper, zinc, magnesium, phosphate, acetate, pyruvate, malic acid, β-alanine, arginine, glutamine, ornithine, taurine, Vitamin C, glucose, and/or derivatives thereof. In exemplary embodiments, the disclosure relates to crystalloid fluids comprising sodium, chloride, potassium, and calcium in water, the improvement comprising from about 56-140 µmol/L of serine and/or from about 92-240 µmol/L of threonine, and/or derivatives thereof, and optionally one or more additional components chosen from copper, zinc, magnesium, phosphate, acetate, pyruvate, malic acid, and/or derivatives thereof. In other exemplary embodiments, the disclosure relates to crystalloid fluids comprising sodium, chloride, potassium, and calcium in water, the improvement comprising from about 56-140 µmol/L of serine and/or from about 92-240 µmol/L of threonine, and/or derivatives thereof, and optionally one or more additional components chosen from copper, zinc, magnesium, phosphate, acetate, pyruvate, malic acid, β-alanine, arginine, glutamine, ornithine, taurine, Vitamin C, glucose, and/or derivatives thereof.

In still further embodiments, the disclosure relates to methods of using the fluid compositions, e.g. sterile bioactive fluid compositions. The methods may, in various embodiments, be for resuscitative care, supportive care, treatment, and/or delivery of therapeutics, active agents, and/or diagnostics. The methods may include using any of the aforementioned fluid compositions, for example sterile bioactive fluid compositions, in methods of enabling survival and/or proliferation of stressed or damaged endothelial cells; methods of promoting the survival and/or proliferation of endothelial cells in a subject receiving or in need of receiving IV fluid therapy; methods of protecting and/or preserving vascular integrity in a subject receiving or in need of receiving IV fluid therapy; methods of preventing or reducing extravasation in a subject receiving or in need of receiving IV fluid therapy; methods of administering a therapeutic, diagnostic, or active agent and/or reducing the effective dose or amount of a therapeutic, diagnostic, or active agent administered to a subject in need of such therapeutic, diagnostic, or active agent; methods of preserving tissue oxygen perfusion in a subject receiving or in need of receiving IV fluid therapy; and/or methods of improving and/or normalizing physiological and/or metabolic markers of clinical outcome, improving survival time, and/or reducing morbidity in a subject with serious injury and/or illness, for example traumatic injury, hemorrhage, and/or hemorrhagic shock.

For example, in various embodiments the disclosure relates to methods of preventing or reducing extravasation in a subject receiving or in need of receiving intravenous fluids, the method comprising administering to the subject a sterile bioactive fluid composition comprising: (a) at least one amino acid chosen from serine, threonine, and/or derivatives thereof, (b) at least one additional component chosen from chloride, sodium, copper, zinc, magnesium, phosphate, potassium, acetate, pyruvate, malic acid, and/or derivatives thereof, and (c) a physiologically acceptable carrier fluid, where the compositions are optionally free or essentially free of blood and/or blood products. In various embodiments, the compositions that can be used in such methods of preventing or reducing extravasation are crystalloid fluids. The amount(s) of serine, threonine, and/or derivatives thereof present in the compositions used to prevent or reduce extravasation may, for example, be within or near physiological levels. For example, the amount of serine may range from about 56-140 µmol/L and/or the amount of threonine may range from about 92-240 µmol/L. In some embodiments, the bioactive fluid compositions used in the methods of preventing or reducing extravasation comprise (a) at least one amino acid chosen from serine, threonine, and/or derivatives thereof, wherein the amount(s) of serine, threonine, and/or derivatives thereof are within or near physiological levels, for example from about 56-140 µmol/L of serine and/or from about 92-240 µmol/L of threonine, (b) from about 95-115 mmol/L of chloride, from about 115-150 mmol/L of sodium, from about 5-24 µmol/L of copper, from about 15-70 µmol/L of zinc, from about 0.2-1.0 mmol/L of magnesium, from about 0.8-2 mmol/L of phosphate, from about 2-5 mmol/L of potassium, from about 2-45 mmol/L of acetate, from about 0.03-2.5 mmol/L of pyruvate, and/or from about 1-15 mmol/L of malic acid, and (c) a physiologically acceptable carrier fluid, e.g. water.

In further exemplary embodiments, the disclosure relates to methods of preventing or reducing extravasation in a subject receiving or in need of receiving intravenous fluids, the method comprising administering to the subject a sterile bioactive fluid composition comprising: (a) at least one amino acid chosen from serine, threonine, and/or derivatives thereof, (b) chloride, sodium, copper, zinc, magnesium, phosphate, potassium, acetate, pyruvate, and malic acid, and (c) a physiologically acceptable carrier fluid, where the compositions are optionally free or essentially free of blood and/or blood products. In various embodiments, the compositions that can be used in such methods of preventing or reducing extravasation are crystalloid fluids. The amount(s) of serine, threonine, and/or derivatives thereof present in the compositions used to prevent or reduce extravasation may, for example, be within or near physiological levels. For example, the amount of serine may range from about 56-140 µmol/L and/or the amount of threonine may range from about 92-240 µmol/L. In some embodiments, the bioactive fluid compositions used in the methods of preventing or reducing extravasation comprise (a) at least one amino acid chosen from serine, threonine, and/or derivatives thereof, wherein the amount(s) of serine, threonine, and/or derivatives thereof are within or near physiological levels, for example from about 56-140 µmol/L of serine and/or from about 92-240 µmol/L of threonine, (b) from about 95-115 mmol/L of chloride, from about 115-150 mmol/L of sodium, from about 5-24 µmol/L of copper, from about 15-70 µmol/L of zinc, from about 0.2-1.0 mmol/L of magnesium, from about 0.8-2 mmol/L of phosphate, from about 2-5 mmol/L of potassium, from about 2-45 mmol/L of acetate, from about 0.03-2.5 mmol/L of pyruvate, and from about 1-15 mmol/L of malic acid, and (c) a physiologically acceptable carrier fluid, e.g. water.

In additional exemplary embodiments, the disclosure relates to methods of preventing or reducing extravasation in a subject receiving or in need of receiving intravenous fluids, the method comprising administering to the subject a sterile bioactive fluid composition comprising: (a) at least one amino acid chosen from serine, threonine, and/or derivatives thereof, (b) at least one additional component chosen from chloride, sodium, copper, zinc, magnesium, phosphate, potassium, acetate, pyruvate, malic acid, β-alanine, arginine, glutamine, ornithine, taurine, Vitamin C, glucose, and/or derivatives thereof, and (c) a physiologically acceptable carrier fluid, where the compositions are optionally free or essentially free of blood and/or blood products. In various embodiments, the compositions that can be used in such methods of preventing or reducing extravasation are crystalloid fluids. The amount(s) of serine, threonine, and/or derivatives thereof present in the compositions used to prevent or reduce extravasation may, for example, be within or near physiological levels. For example, the amount of serine may range from about 56-140 µmol/L and/or the amount of threonine may range from about 92-240 µmol/L. In some embodiments, the bioactive fluid compositions used in the methods of preventing or reducing extravasation comprise (a) at least one amino acid chosen from serine, threonine, and/or derivatives thereof, wherein the amount(s) of serine, threonine, and/or derivatives thereof are within or near physiological levels, for example from about 56-140 µmol/L of serine and/or from about 92-240 µmol/L of threonine, (b) from about 95-115 mmol/L of chloride, from about 115-150 mmol/L of sodium, from about 5-24 µmol/L of copper, from about 15-70 µmol/L of zinc, from about 0.2-1.0 mmol/L of magnesium, from about 0.8-2 mmol/L of phosphate, from about 2-5 mmol/L of potassium, from about 2-45 mmol/L of acetate, from about 0.03-2.5 mmol/L of pyruvate, from about 1-15 mmol/L of malic acid, from about 200-600 mol/L of β-alanine, from about 10-70 µmol/L of arginine, from about 390-650 µmol/L of glutamine, from about 27-80 µmol/L of ornithine, from about 45-440 µmol/L of taurine, from about 11-120 µmol/L of Vitamin C, and/or from about 3-25 mmol/L of glucose, and (c) a physiologically acceptable carrier fluid, e.g. water.

In yet further exemplary embodiments, the disclosure relates to methods of preventing or reducing extravasation in a subject receiving or in need of receiving intravenous fluids, the method comprising administering to the subject a sterile bioactive fluid composition comprising: (a) at least one amino acid chosen from serine, threonine, and/or derivatives thereof, (b) chloride, sodium, copper, zinc, magnesium, phosphate, potassium, acetate, pyruvate, malic acid, β-alanine, arginine, glutamine, ornithine, taurine, Vitamin C, and glucose, and (c) a physiologically acceptable carrier fluid, where the compositions are optionally free or essentially free of blood and/or blood products. In various embodiments, the compositions that can be used in such methods of preventing or reducing extravasation are crystalloid fluids. The amount(s) of serine, threonine, and/or derivatives thereof present in the compositions used to prevent or reduce extravasation may, for example, be within or near physiological levels. For example, the amount of serine may range from about 56-140 µmol/L and/or the amount of threonine may range from about 92-240 µmol/L. In some embodiments, the bioactive fluid compositions used in the methods of preventing or reducing extravasation comprise (a) at least one amino acid chosen from serine, threonine, and/or derivatives thereof, wherein the amount(s) of serine, threonine, and/or derivatives thereof are within or near physiological levels, for example from about 56-140 µmol/L of serine and/or from about 92-240 µmol/L of threonine, (b) from about 95-115 mmol/L of chloride, from about 115-150 mmol/L of sodium, from about 5-24 µmol/L of copper, from about 15-70 µmol/L of zinc, from about 0.2-1.0 mmol/L of magnesium, from about 0.8-2 mmol/L of phosphate, from about 2-5 mmol/L of potassium, from about 2-45 mmol/L of acetate, from about 0.03-2.5 mmol/L of pyruvate, from about 1-15 mmol/L of malic acid, from about 200-600 µmol/L of β-alanine, from about 10-70 µmol/L of arginine, from about 390-650 µmol/L of glutamine, from about 27-80 µmol/L of ornithine, from about 45-440 µmol/L of taurine, from about 11-120 µmol/L of Vitamin C, and from about 3-25 mmol/L of glucose, and (c) a physiologically acceptable carrier fluid, e.g. water.

In various embodiments, the disclosure relates to methods of using the fluid compositions, e.g. sterile bioactive fluid compositions, comprising (a) means for achieving any of the aforementioned methods, and (b) a physiologically acceptable carrier fluid. Optionally, the compositions may be free or essentially free of blood and/or blood products. In some embodiments, the compositions are crystalloid fluids.

For example, in various embodiments the disclosure relates to methods of using the fluid compositions, e.g. sterile bioactive fluid compositions, comprising (a) means for preventing or reducing extravasation in a subject receiving or in need of receiving intravenous fluids, and (b) a physiologically acceptable carrier fluid. In other embodiments, the disclosure relates to methods of using the fluid compositions, e.g. sterile bioactive fluid compositions, comprising (a) means for enabling survival and/or proliferation of stressed or damaged endothelial cells in a subject receiving or in need of receiving intravenous fluids, and (b) a physiologically acceptable carrier fluid. In other embodiments, the disclosure relates to methods of using the fluid compositions, e.g. sterile bioactive fluid compositions, comprising (a) means for protecting and/or preserving vascular integrity in a subject receiving or in need of receiving intravenous fluids, and (b) a physiologically acceptable carrier fluid. In other embodiments, the disclosure relates to methods of using the fluid compositions, e.g. sterile bioactive fluid compositions, comprising (a) means for administering a therapeutic, diagnostic, or active agent and/or reducing the effective dose or amount of a therapeutic, diagnostic, or active agent administered to a subject in need of such therapeutic, diagnostic, or active agent, and (b) a physiologically acceptable carrier fluid. In other embodiments, the disclosure relates to methods of using the fluid compositions, e.g. sterile bioactive fluid compositions, comprising (a) means for preserving tissue oxygen perfusion in a subject receiving or in need of receiving intravenous fluids, and (b) a physiologically acceptable carrier fluid. In other embodiments, the disclosure relates to methods of using the fluid compositions, e.g. sterile bioactive fluid compositions, comprising (a) means for improving and/or normalizing physiological and/or metabolic markers of clinical outcome, improving survival time, and/or reducing morbidity in a subject with serious injury and/or illness, for example traumatic injury, hemorrhage, and/or hemorrhagic shock, and (b) a physiologically acceptable carrier fluid.

DEFINITIONS

As used herein, "crystalloid fluids" refer to aqueous solutions of physiologically relevant ions and water. Current crystalloid solutions freely pass through semi-permeable biological barriers including membranes (e.g., NS and LR). Crystalloid fluids are distinguishable from colloid fluids, which contain naturally-occurring or synthetic large molecular weight globular proteins or polymers (e.g., albumin, hetastarch [hydroxyethyl starch], gelatin, and dextran) suspended in a crystalloid solution. There are two basic classes of "isotonic" crystalloid solution: normal saline (0.9% sodium chloride w/v) and balanced crystalloids (e.g., Lactated Ringer's solution, Hartmann's solution, Plasma-Lyte, Normosol, Isolyte). Normal saline contains 154 mmol/L of sodium and chloride—a chloride concentration approximately 50% greater than that of human extracellular fluid. In contrast, balanced crystalloids contain sodium, potassium, chloride, and acid-base compositions more similar to that of extracellular fluid.

Herein, the term "bioactive fluid composition" means any of the various compositions according to the disclosure, which have been found to exert advantageous biological effects when administered intravenously, for example survival and/or proliferation of stressed or damaged endothelial cells. However, it should be understood that the compositions described may be used in various methods that do not include intravenous administration, and such compositions are nevertheless included within the term "bioactive fluid compositions."

As used herein, "standard-of-care" fluids are normal saline (NS), Lactated Ringer's solution (LR), and other known balanced crystalloids such as Hartmann's solution, Plasma-Lyte, Normosol, and Isolyte.

As used herein, "physiological levels" are levels found in the blood of a normal functioning mammal.

The terms "subject," "individual," "patient," or the like, are used interchangeably herein and refer to a vertebrate, preferably a mammal. Mammals include, but are not limited to, humans.

As used herein, "IV therapy," "IV fluid therapy," "IV administration," or variations thereof are used interchangeably herein to refer to techniques that administer fluids, which may in some cases contain components such as therapeutic agents, diagnostic agents, active agents, nutritional components, etc., directly into the vasculature, e.g. a vein. Intravenous therapies may include, for example, single or multiple doses by injection, delivery as a bolus or one-time dose, sequential doses, intermittent doses, and administration as an infusion or extended infusion or drip.

As used herein, "extravasation" refers to the leakage of fluid and other components (carried by or in or with the fluid) from blood vessels into surrounding areas, such as, for example, surrounding tissue.

As used herein, "resuscitative care" means management of life- or limb-threatening injuries, including, for example, emergency medical treatment, advanced trauma management, and lifesaving surgery to enable the subject to tolerate evacuation to the next level of care.

As used herein, "supportive care" means care given to improve the quality of life of a subject, including, for example, treatment to prevent or treat as early as possible the symptoms of an illness or injury, side effects caused by treatment of an illness or injury, nutritional care, and symptom management.

As used herein, "cofactor" means a non-protein chemical compound or metallic ion that assists with a biological chemical reaction. Cofactors can be either inorganic ions or complex organic molecules known as coenzymes.

As used herein, "electrolyte" means a substance that has a positive or negative charge when dissolved in water.

As used herein, "therapeutic" refers to chemicals or compounds, including small molecule drugs and large molecule drugs (also known as biologics), used for preventing or treating a condition, disorder, or disease.

As used herein, "diagnostic" refers to chemicals or compounds injected or infused for the purpose diagnosing a condition, disorder, or disease.

As used herein, "preventing" means stopping, ameliorating, or keeping from occurring, to any degree.

Herein, the term "reducing" means slowing the progression of, lessening, or minimizing to any degree.

As used herein, a "derivative" of a compound, agent, or drug is different in chemical structure than such compound, agent, or drug, but the active component of the derivative produces the same pharmacological effect as such compound, agent, or drug. A non-limiting example of a derivative of a compound includes a salt of said compound, and a non-limiting example of a derivative of an amino acid includes effective multimers of two or more amino acids directly conjugated to each other, for example dipeptides such as glycine-glutamine dipeptide or alanyl-glutamine. In various embodiments, derivatives comprise, consist essentially of, or consist of components that allow the composition to be in crystalloid form.

As used herein, "sterile" means that a composition is free from components that would be incompatible with administration directly into the vascular system of a mammal, such as germs or microorganisms.

As used herein, "physiologically acceptable carriers" include those that are considered clinically suitable for IV administration and can include, for example, water or crystalloid fluids such as normal saline, Lactated Ringer's, Hartmann's solution, Plasma-Lyte, Normosol, Isolyte, or variations thereof.

As used herein, "within or close to physiological levels" and variations thereof means no more than a one to three (1-3) fold difference from levels that are considered clinically normal physiological levels of the component specified.

As used herein, a composition that is "free" of a specified component means that the component is not present in the composition within detectable limits, and a composition that is "essentially free" of a specified component means that the component is not present in the composition in an amount greater than 0.1% w/w in the fluid composition. However, it is understood that the terms "free" and "essentially free" refer to the amount of a component added to the composition per se. As such, this would not include an amount of the component present in the composition as a result of being present as a minor component in a raw material.

Herein, the term "essential amino acids" is used according to its ordinary meaning to refer to those amino acids that are not synthesized by mammals, and are therefore considered to be dietarily essential or indispensable nutrients. Essential amino acids are histidine, isoleucine, leucine, lysine, methionine, phenylalanine, threonine, tryptophan, and valine, and are referred to collectively herein as "AAE." As used herein, all references to amino acids and essential amino acids include derivatives thereof, unless expressly stated otherwise.

The terms "promote the survival of vascular endothelial cells," "promote the function of vascular endothelial cells," "increase the survival of vascular endothelial cells," "increase the function of vascular endothelial cells," or variations thereof are used interchangeably to mean that the number of cells that survive or duration of survival of cells is greater in comparison to treatment with NS or LR under the same conditions, for example in a HUVECs model as shown below.

As used herein, "reducing extravasation" with bioactive fluid compositions according to the disclosure means that the amount of fluid that leaks from the vasculature during and/or after administration of the bioactive fluid composition is less than the amount of fluid that leaks from the vasculature during and/or after administration of NS or LR under the same conditions.

As used herein, the term "preserving tissue oxygen perfusion" means that the oxygen level in the tissue is greater in comparison to treatment with NS or LR under the same conditions, for example in an in-vivo exchange transfusion model as shown below.

As used herein, the term "reducing the effective dose or amount of a therapeutic, diagnostic, or active agent" that is administered to a subject in a bioactive fluid composition according to the disclosure means that the amount of such therapeutic, diagnostic, or active agent administered to a subject is less than the amount required to achieve the same level of efficacy when administered in NS or LR under the same conditions.

As used herein, "improving and/or normalizing physiological and/or metabolic markers of clinical outcome" refers to a determination that one or more of base deficit, pH, glucose levels, lactate levels, blood pressure, and heart rate of a subject to whom a bioactive fluid composition according to the disclosure has been administered is clinically considered to be better than the same marker when NS or LR is administered under the same conditions.

Herein, "low molecular weight" means a component having a molecular weight not greater than about 20,000 g/mol. For example, a low molecular weight component may have a molecular weight no greater than 18,000 g/mol, no greater than 15,000 g/mol, no greater than 12,000 g/mol, no greater than 10,000 g/mol, no greater than 7,500 g/mol, no greater than 5,000 g/mol, no greater than 4,000 g/mol, no greater than 3,000 g/mol, no greater than 2,000 g/mol, no greater than 1,000 g/mol, no greater than 750 g/mol, or no greater than 500 g/mol. Unless otherwise specified, "low molecular weight" means not greater than about 20,000 g/mol.

As used herein, "an amount of" or "level of" a component refers to the amount or level of the active component present in the composition. For example, a specified amount of chloride in a composition is determined by calculating the total chloride content contributed from all components contributing chloride to the composition. It is to be understood that in every instance in which exemplary ranges are provided for various components, all disclosed ranges and subranges for such component are intended to also be useful.

Herein, the use of the singular includes the plural unless specifically stated otherwise. The singular forms "a," "an," "the," and "at least one" are understood to encompass the plural as well as the singular unless the context clearly dictates otherwise. The expression "one or more" means "at least one" and thus includes individual components as well as mixtures/combinations. Likewise, the term "a derivative thereof" also encompasses "derivatives thereof," "a physiologically acceptable carrier fluid" also encompasses "physiologically acceptable carrier fluids," and so on.

The term "and/or" should be understood to include both the conjunctive and the disjunctive. For example, "amino acids and/or derivatives thereof" means "amino acids and derivatives thereof" as well as "amino acids or derivatives thereof," and expressly covers instances of either. Thus, where the disclosure refers to an element "chosen from A, B, C, D, E, F, and/or a derivative thereof," it indicates that that one of A, B, C, D, F, a derivative of A, a derivative of B, a derivative of C, a derivative of D, a derivative of E, or a derivative of F may be included, or a mixture of any two or more of A, B, C, D, E, F, a derivative of A, a derivative of B, a derivative of C, a derivative of D, a derivative of E, and a derivative of F may be included.

As used herein, the term "salts" may include salts of a component having any suitable counterion for use in the context indicated, such as an alkali metal or alkaline earth metal. This list of counterions, however, is non-limiting. Salts also include a dissociated form of a compound, e.g. in an aqueous solution.

All ranges and amounts given herein are intended to include sub-ranges and amounts using any disclosed point as an end point, and all endpoints are intended to be included unless expressly stated otherwise. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not expressly stated, unless expressly stated otherwise. Similarly, a range given of "about 1% to 10%" is intended to have the term "about" modifying both the 1% and the 10% endpoints. The term "about" is used herein to indicate a difference of up to +10% from the stated number, such as ±9%, ±8%, ±7%, ±6%, ±5%, ±4%, ±3%, ±2%, ±1%, or ±0.5%. Unless stated otherwise, "about" means ±10%. Likewise, all endpoints of ranges are understood to be individually disclosed, such that, for example, a range of 1% to 10% is understood to disclose both 1% and 10%.

Various components disclosed herein exist in enantiomeric form. Although a particular enantiomeric form may be recited herein, it is intended that either form may be used unless expressly stated otherwise.

DETAILED DESCRIPTION

Figure 1:
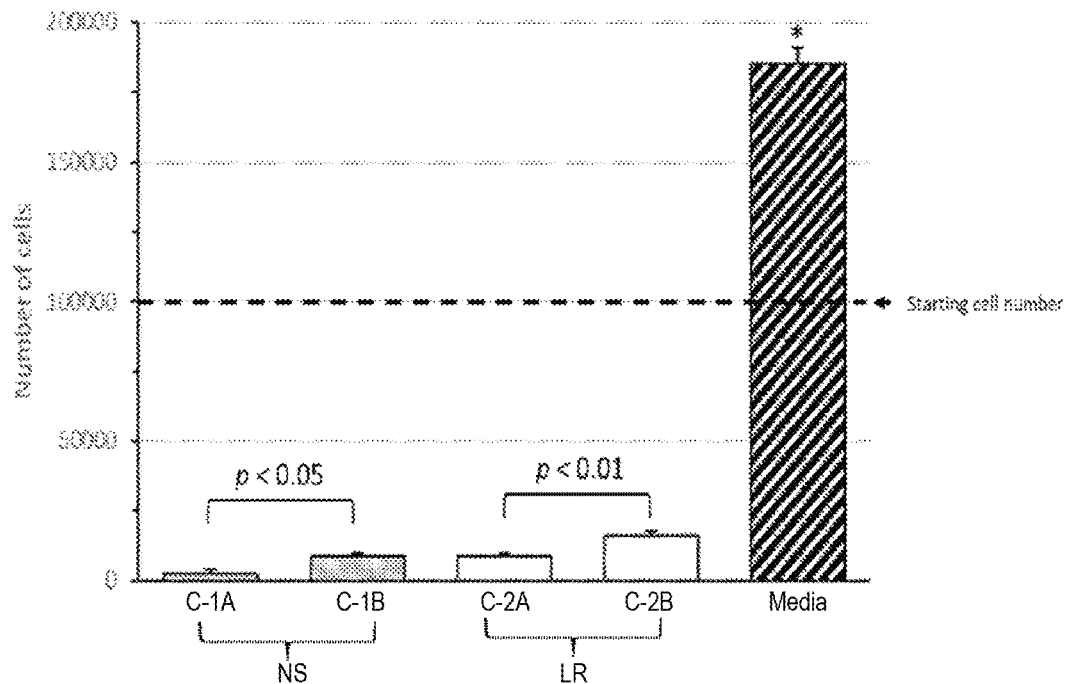
FIG. 1 depicts cell mortality in primary human vascular endothelial cell (HUVEC) cultures following exposure to standard-of-care IV fluids (NS and LR) and the effect of essential amino acids (AAE). Addition of AAE significantly reduced mortality of HUVEC.

The disclosure relates to bioactive fluid compositions and methods of using the bioactive fluid compositions. It has been discovered that the bioactive fluid compositions described herein preserve the integrity of and promote the survival and/or function of vascular endothelial cells when used in IV fluid therapy. Thus, the bioactive fluid compositions provide various advantages when used in place of traditional crystalloid fluids such as NS or LR for replacement of lost fluid volume, resuscitative care, supportive care, treatment, or delivery of therapeutics, active agents, and/or diagnostics.

Bioactive fluid compositions according to the disclosure have been shown to improve the recovery of stressed endothelial cells and tissues from both traumatic as well as non-traumatic causes. For example, loss of blood volume leads to cellular stress and dysfunction as a result of insufficient circulatory capacity to move oxygen-carrying red blood cells and other components carried by or within the blood. The bioactive fluid compositions described herein have been found to reduce cellular stress, thereby aiding in the recovery of cells and tissues.

I. Compositions

Bioactive fluid compositions according to the disclosure are sterile, and thus are suitable for IV administration to a subject receiving or in need of receiving IV fluid therapy. In various embodiments, all components included in the bioactive fluid compositions are water soluble and low molecular weight components that permit the compositions to remain in the form of crystalloid fluids rather than colloidal fluids. However, in at least some embodiments, one or more components that is/are not water soluble and/or not low molecular weight can be included. In some embodiments, the compositions are free or substantially free of any component that would cause the composition to be in a form other than a crystalloid fluid.

It has been discovered that addition of amino acids to standard-of-care crystalloid fluids such as NS or LR results in increased survival and/or function of endothelial cells, thereby enhancing the efficacy and decreasing the deleterious effect of such fluids. Accordingly, some embodiments relate to bioactive fluid compositions comprising amino acids and/or derivatives thereof, and a physiologically acceptable carrier fluid. Useful amino acids include, for example, amino carboxylic acids such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, and/or derivatives thereof, and amino sulfonic acids such as taurine and/or derivatives thereof. In various embodiments, the amino acid(s) present in the compositions comprise, consist essentially of, or consist of serine, threonine, and/or derivatives thereof. In other embodiments the compositions are free or substantially free of cysteine. In some embodiments, it may be advantageous to use the L-form of amino acids in compositions according to the disclosure. In some embodiments, it may be advantageous to use amounts of amino acids or derivatives thereof that are within or close to physiological levels. These levels are quite different from levels contained in fluids used, for example, for intravenous feeding, wherein high levels of amino acids are used. In various embodiments, bioactive fluid compositions according to the disclosure can be obtained by adding such physiological levels of one or more amino acids and/or derivatives thereof to any standard-of-care crystalloid fluid known in the art, such as NS or LR.

Addition of amino acids, including essential amino acids, to standard-of care crystalloid fluids in amounts within or close to physiological levels has been found to increase the ability of such fluids to promote survival of vascular endothelial cells, thus improving the therapeutic utility of such as IV fluids, as shown in Example 1 below. Accordingly, in one embodiment a bioactive fluid composition according to the disclosure comprises one or more essential amino acid and/or derivatives thereof, and a physiologically acceptable carrier, where said essential amino acid levels are chosen to be within or close to physiological levels. For example, the levels of these amino acids, may be, for example, within or close to the following ranges: L-Histidine (e.g. ranging from about 26-120 µmol/L, such as from about 45-100 µmol/L, or from about 60-85 µmol/L), L-Isoleucine (e.g. ranging from about 42-100 µmol/L, such as from about 50-90 µmol/L, or from about 60-80 µmol/L), L-Leucine (e.g. ranging from about 66-170 µmol/L, such as from about 85-150 µmol/L, or from about 100-130 µmol/L), L-Lysine (e.g. ranging from about 150-220 µmol/L, such as from about 160-200 µmol/L, or from about 170-195 µmol/L), L-Methionine (e.g. ranging from about 16-30 µmol/L, such as from about 18-28 µmol/L, or from about 20-26 µmol/L), L-Phenylalanine (e.g. ranging from about 41-68 µmol/L, such as from about 45-65 µmol/L, or from about 50-60 µmol/L), L-Threonine (e.g. ranging from about 92-240 µmol/L, such as from about 110-220 µmol/L, or from about 125-200 µmol/L), L-Tryptophan (e.g. ranging from about 25-150 µmol/L, such as from about 45-125 µmol/L, or from about 60-110 µmol/L), and/or L-Valine (e.g. ranging from about 150-310 µmol/L, such as from about 175-285 µmol/L, or from about 200-260 µmol/L). In other embodiments, physiological levels of one or more essential amino acids and/or derivatives thereof can be added to any crystalloid fluid, including for example those described herein. In another embodiment, at least one amino acid chosen from serine and threonine may be added to any crystalloid fluid, including for example those described herein. For example, from 92-240 µmol/L of L-Threonine and/or from 56-140 µmol/L of L-Serine may be used in any bioactive fluid composition according to the disclosure. Such compositions may be advantageous for subjects with serious illness or injury who are receiving or in need of receiving IV therapy for resuscitative care, in subjects who are receiving or in need of receiving IV therapy for supportive care, and/or for delivery of therapeutics and/or diagnostics. As described above, such fluids promote the survival of endothelial cells not seen with standard-of-care crystalloid fluids including NS or LR.

It has also been discovered that an electrolyte and buffering system in bioactive fluid compositions described herein has a positive impact on the survival and function of endothelial cells and the resultant efficacy of the fluid, for example as a resuscitative therapy. As shown in Example 2 herein, the use of electrolytes is protective of endothelial cells, thus contributing to the efficacy of the bioactive fluid compositions. Therefore, in some embodiments the bioactive fluid compositions include a combination of one or more of the following electrolytes: chloride, sodium, copper, zinc, magnesium, phosphate, potassium, acetate, pyruvate, malic acid, and/or derivatives thereof. These compounds are referred to collectively herein as "GND electrolytes" or "GE." In various embodiments the bioactive fluid composition comprises one or more of the following compounds and/or derivatives thereof, which may be, for example, within or close to the following ranges: chloride (e.g. ranging from about 95-115 mmol/L, such as, for example, from about 100-110 mmol/L), sodium (e.g. ranging from about 115-150 mmol/L, such as, for example, from about 120-145 mmol/L, or from about 125-140 mmol/L), copper (e.g. ranging from about 5-24 µmol/L, such as, for example, from about 8-20 µmol/L, or from about 10-18 µmol/L), zinc (e.g. ranging from about 15-70 µmol/L, such as, for example, from about 25-60 µmol/L, or from about 35-50 µmol/L), magnesium (e.g. ranging from about 0.2-1.0 mmol/L, such as, for example, from about 0.35-0.75 mmol/L), phosphate (e.g. ranging from about 0.8-2 mmol/L, such as, for example, from about 1-1.75 mmol/L, or from about 1.2-1.6 mmol/L), potassium (e.g. ranging from about 2-5 mmol/L, such as, for example, from about 2.5-4.5 mmol/L, or from about 3-4 mmol/L), acetate (e.g. ranging from about 2-45 mmol/L, such as, for example, from about 8-35 mmol/L, or from about 15-30 mmol/L), pyruvate (e.g. ranging from about 0.03-2.5 mmol/L, such as, for example, from about 0.1-2.25 mmol/L, or from about 0.7-2 mmol/L), and malic acid (e.g. ranging from about 1-15 mmol/L, such as, for example, from about 3-12 mmol/L, or from about 5-10 mmol/L).

Further, as also shown in Example 2, various combinations of AAE and GND electrolytes in bioactive fluid compositions promote survival of vascular endothelial cells and, in some cases, results in endothelial cell proliferation. Accordingly, some embodiments relate to bioactive fluid compositions comprising GND electrolytes, AAE, and a physiologically acceptable carrier fluid, wherein said AAE are within or close to physiological levels. In some embodiments, the bioactive fluid compositions comprise some or all of the following AAE and GND electrolytes, which may be, for example, within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), and L-Valine (150-310 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof.

In other embodiments, the bioactive fluid compositions comprise GND electrolytes and at least one amino acid chosen from serine and threonine. For example, the bioactive fluid composition may comprise some or all of the following components, which may be, for example, within or close to the stated ranges: chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Threonine (92-240 µmol/L), L-Serine (56-140

μmol/L), and/or derivatives thereof, in a physiologically acceptable carrier fluid. In another embodiment, the bioactive fluid compositions may comprise some or all of the following components, which may be, for example, within or close to the stated ranges: chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Serine (56-140 μmol/L), and/or derivatives thereof, in a physiologically acceptable carrier fluid. In further embodiments still, the bioactive fluid compositions may comprise some or all of the following components, which may be, for example, within or close to the stated ranges: chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Threonine (92-240 μmol/L), and/or derivatives thereof, in a physiologically acceptable carrier fluid.

Further embodiments relate to bioactive fluid compositions comprising one or more of the following: β-Alanine, L-Arginine, L-Glutamine, L-Ornithine, L-Serine, L-Taurine, Vitamin B6 (also referred to as pyridoxine), folic acid, Vitamin C, glucose (e.g. D-glucose), and/or derivatives thereof. These components are also referred to collectively herein as "GND minimal" or "Min." For example, bioactive fluid compositions may include some or all of the following components, which may be, for example, within or close to the stated ranges: β-Alanine (e.g. ranging from about 200-600 μmol/L, such as from about 275-525 μmol/L, or from about 325-475 μmol/L), L-Arginine (e.g. ranging from about 10-70 μmol/L, such as from about 20-60 μmol/L, or from about 30-50 μmol/L), L-Glutamine (e.g. ranging from about 390-650 μmol/L, such as from about 425-610 μmol/L, or from about 475-575 μmol/L), L-Ornithine (e.g. ranging from about 27-80 μmol/L, such as from about 35-75 μmol/L, or from about 40-65 μmol/L), L-Serine (e.g. ranging from about 56-140 μmol/L, such as from about 65-130 μmol/L, or from about 80-120 μmol/L), L-Taurine (e.g. ranging from about 45-440 μmol/L, such as from about 75-400 μmol/L, or from about 150-350 μmol/L), Vitamin B6 (e.g. ranging from about 30-144 nmol/L, such as from about 45-125 nmol/L, or from about 60-110 nmol/L), folic acid (e.g. ranging from about 5-250 nmol/L, such as from about 55-200 nmol/L, or from about 95-155 nmol/L), Vitamin C (e.g. ranging from about 11-120 μmol/L, such as from about 20-105 μmol/L, or from about 40-90 μmol/L), glucose (e.g. ranging from about 3-25 mmol/L, such as from about 5-20 mmol/L, or from about 7-18 mmol/L), and/or derivatives thereof, in a physiologically acceptable carrier fluid. In some embodiments, however, the compositions are free or substantially free of Vitamin B6 and/or folic acid.

Thus, in further embodiments the bioactive fluid compositions comprise GND minimal and a physiologically acceptable carrier fluid, with GND electrolytes and/or AAE. For example, bioactive fluid compositions may comprise some or all the following components, which may be, for example, within or close to the stated ranges: β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. In some embodiments, the compositions are free or substantially free of Vitamin B6 and/or folic acid.

Another exemplary bioactive fluid composition comprises some or all of the following components, which may be, for example, within or close to the stated ranges: β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), L-Histidine (26-120 μmol/L), L-Isoleucine (42-100 μmol/L), L-Leucine (66-170 μmol/L), L-Lysine (150-220 μmol/L), L-Methionine (16-30 μmol/L), L-Phenylalanine (41-68 μmol/L), L-Threonine (92-240 μmol/L), L-Tryptophan (25-150 μmol/L), L-Valine (150-310 mol/L), and/or derivatives thereof, in a physiologically acceptable carrier fluid. Yet another exemplary bioactive fluid composition comprises some or all of the following components, which may be, for example, within or close to the stated ranges: β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 μmol/L), L-Isoleucine (42-100 mol/L), L-Leucine (66-170 μmol/L), L-Lysine (150-220 μmol/L), L-Methionine (16-30 μmol/L), L-Phenylalanine (41-68 μmol/L), L-Threonine (92-240 μmol/L), L-Tryptophan (25-150 μmol/L), L-Valine (150-310 μmol/L), and/or derivatives thereof, in a physiologically acceptable carrier fluid. In some embodiments, however, the compositions are free or substantially free of Vitamin B6 and/or folic acid.

In yet further embodiments, the bioactive fluid compositions comprise L-Asparagine, L-Aspartic acid, L-Citrulline, L-Cysteine, L-Glutamic acid, Glycine, L-Proline, L-Tyrosine, derivatives thereof, or combinations of two or more thereof. For example, the bioactive fluid composition may comprise some or all of the following components, which may be, for example, within or close to the stated ranges: L-Asparagine (40-150 μmol/L), L-Aspartic acid (0.1-10 μmol/L), L-Citrulline (16-55 μmol/L), L-Cysteine (30-65 μmol/L), L-Glutamic acid (18-98 μmol/L), Glycine (170-330 μmol/L), L-Proline (110-360 μmol/L), L-Tyrosine (45-74 μmol/L), and/or derivatives thereof, in a physiologically acceptable carrier fluid. In some embodiments, however, the compositions are free or substantially free of L-Cysteine. The compositions may also comprise GND minimal, GND electrolytes, and/or AAE. Thus, an exemplary bioactive fluid composition comprises some or all of the following components, which may be, for example, within or close to the stated ranges: L-Asparagine (40-150 μmol/L), L-Aspartic acid (0.1-10 μmol/L), L-Citrulline (16-55 μmol/L), L-Cysteine (30-65 μmol/L), L-Glutamic acid (18-98 μmol/L), Glycine (170-330 μmol/L), L-Proline (110-360 μmol/L), L-Tyrosine (45-74 μmol/L), β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. In some embodiments, the compositions are free or substantially free of L-Cysteine, Vitamin B6, and/or folic acid.

Another exemplary bioactive fluid composition comprises some or all of the following components, which may be, for example, within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. In some embodiments, the compositions are free or substantially free of L-Cysteine, Vitamin B6, and/or folic acid.

Yet another exemplary bioactive fluid composition, referred to as "GND," "GND complete," or "Comp," comprises some or all of the following components, which may be, for example, within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. In some embodiments, however, the compositions are free or substantially free of L-Cysteine, Vitamin B6, and/or folic acid.

In an embodiment, the bioactive fluid composition comprises L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), and L-Valine (150-310 µmol/L), in a physiologically acceptable carrier fluid. In some embodiments, however, the compositions are free or substantially free of L-Cysteine, Vitamin B6, and/or folic acid.

In another embodiment, the bioactive fluid composition comprises chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and L-Threonine (92-240 µmol/L) in a physiologically acceptable carrier fluid.

In a further embodiment, the bioactive fluid composition comprises chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and L-Serine (56-140 µmol/L) in a physiologically acceptable carrier fluid.

In various embodiments, the compositions according to the disclosure comprise (a) a means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock, and (b) a physiologically acceptable carrier fluid. Suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include any of the aforementioned combinations of components.

For example, in some embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include the components identified herein as AAE. In other embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include the components identified herein as GE. In other embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include the components identified herein as GE+AAE. In other embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include the components identified herein as GND Min. In other embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include the components identified herein as GND Comp.

In still further embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include some or all of the following, within or close to the stated ranges: chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Threonine (92-240 µmol/L), and/or derivatives thereof.

In further embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include some or all of the following, within or close to the stated ranges: chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Serine (56-140 µmol/L), and/or derivatives thereof.

In further embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include some or all of the following, within or close to the stated ranges: chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Threonine (92-240 µmol/L), and/or derivatives thereof In still further embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include some or all of the following, within or close to the stated ranges: chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Serine (56-140 µmol/L), and/or derivatives thereof.

In still further embodiments, suitable means for enabling survival and/or proliferation of stressed or damaged endothelial cells; promoting the survival and/or proliferation of endothelial cells in a subject receiving or in need of receiving IV fluid therapy; protecting and/or preserving vascular integrity in a subject receiving or in need of receiving IV fluid therapy; preventing or reducing extravasation in a subject receiving or in need of receiving IV fluid therapy; administering a therapeutic, diagnostic, or active agent and/or reducing the effective dose or amount of a therapeutic, diagnostic, or active agent administered to a subject in need of such therapeutic, diagnostic, or active agent; preserving tissue oxygen perfusion in a subject receiving or in need of receiving IV fluid therapy; improving and/or normalizing physiological and/or metabolic markers of clinical outcome, improving survival time, and/or reducing morbidity in a subject with serious injury and/or illness, for example traumatic injury, hemorrhage, and/or hemorrhagic shock include some or all of the following, within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof.

In at least some embodiments, other than therapeutics, diagnostics, and/or active agents added when the compositions used as carriers, bioactive fluid compositions according to the disclosure are free or substantially free of blood components or blood products, proteins, antibodies, immunoreactive substances, colloids or oncotic substances, or oxygen-carriers. In such embodiments, it may be simple to prepare and sterilize the compositions for intravenous use in humans and other animals. In some embodiments the bioactive fluid compositions are free or substantially free of calcium, although calcium may be added or used in conjunction with the compositions where warranted.

To be suitable for IV administration, bioactive fluid compositions according to the disclosure comprise a physiologically acceptable carrier fluid. However, in various embodiments, the compositions can be provided in a form suitable to be prepared for administration at or near the time of use, such as, for example, in dried or concentrated forms. For example, the composition may be in dried form, e.g. by lyophilizing the composition or by mixing and milling the components in dry form. The dried form can be reconstituted or mixed with a physiologically acceptable carrier fluid to produce the bioactive fluid compositions described herein. Such a dry formulation may be useful in cases where transportation of fluid preparations is not feasible. The dry formulation can be prepared such that its reconstitution or preparation will result in fluid compositions with concentrations of components described herein. The dry product can, for example, be reconstituted using sterile water infused into a sterile container containing the dry product, and optionally mixing by repeated inversion and manipulation of the bag. In other embodiments, the bioactive fluid compositions can be provided as a concentrated solution, for example ranging from 1× to 5× concentrated form. In such embodiments, the concentrated product can be diluted, e.g. using sterile water, to provide intravenous preparations with concentrations of components described herein.

II. Methods of Treatment

Methods of treatment using any of the described fluid compositions may be implemented for any subject receiving or in need of receiving IV fluids. It is contemplated that fluid compositions according to the disclosure can be used as intra-vascular fluids or as IV fluids for replacement of extracellular fluids. For example, such methods may be implemented in subjects with serious illness or injury receiving IV fluid therapy for resuscitative care, subjects receiving IV fluid therapy for supportive care, subjects receiving IV fluid therapy for treating various conditions, and/or for delivery of therapeutics, active agents, and/or diagnostics to a subject.

As described above, bioactive fluid compositions according to the disclosure enable survival and/or proliferation of stressed or damaged endothelial cells in a manner not seen with standard-of-care crystalloid fluids, including NS or LR. While not wishing to be bound by theory, it is believed that this provides improvements in clinical parameters in subjects receiving crystalloid fluids, for example reduced or arrested fluid extravasation, enhanced or preserved tissue oxygen perfusion, etc.

In various embodiments, the compositions have been shown to prevent the breakdown of endothelial cells and to promote their metabolism in both in vitro and in animal studies. Injury to vascular endothelium is associated with a number of serious illnesses and injury and the degree of injury is associated with markers of clinical prognosis and subject outcomes. Such injury is indicated by the shedding of glycocalyx proteins, including Syndecan-1. In rodent models of serious blood volume loss and shock, infusion of IV fluids such as fresh-frozen plasma that protect or restore the vascular endothelium is associated with improved clinical parameters. As shown in the Examples herein, bioactive fluid compositions according to the disclosure prevent stressed or damaged endothelial cells from shedding Syndecan-1 and support endothelial cell metabolism, thereby enabling the repair of stressed or damaged endothelial cells. As predicted by these data and shown in the Examples below, fluids capable of promoting the viability and proliferation of endothelial cells, protecting endothelial cells from damage, and enabling repair of damaged endothelial cells, are able to prevent injury and promote the primary function of vascular endothelial cells in vivo in a manner not seen with standard-of-care crystalloid fluids, including NS and LR.

Accordingly, one aspect of the disclosure relates to methods of promoting the survival and/or proliferation of endothelial cells in a subject receiving or in need of receiving IV fluid therapy, the method comprising administering to said subject a bioactive fluid composition according to the disclosure. For example, an exemplary embodiment comprises a method of promoting the survival and/or proliferation of endothelial cells in a subject receiving or in need of receiving IV fluid therapy, the method comprising administering to said subject a bioactive fluid composition comprising one or more amino acids, such as AAE, within or close to physiological levels. In an exemplary embodiment, the bioactive fluid composition administered comprises some or all of the following amino acids, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof. The bioactive fluid composition further comprises a physiologically acceptable carrier fluid, which may, for example, be water, or may be a crystalloid fluid such as those described herein, e.g. NS or LR. In some embodiments, the bioactive fluid composition comprises at least one amino acid chosen from serine, threonine, and/or derivatives thereof. For example, from 92-240 µmol/L of L-Threonine and/or from 56-140 µmol/L of L-Serine may be used. In various embodiments, the amino acid(s) present in the compositions comprise, consist essentially of, or consist of serine, threonine, and/or derivatives thereof.

Another exemplary embodiment comprises a method of promoting the survival and/or proliferation of endothelial cells in a subject receiving or in need of receiving IV fluid therapy, the method comprising administering to said subject a bioactive fluid composition comprising a physiologically acceptable carrier fluid, GND electrolytes, and AAE. By way of example only, the bioactive fluid composition administered may comprise some or all of the of the following AAE and GND electrolytes, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof.

Another exemplary embodiment comprises a method of promoting the survival and/or proliferation of endothelial cells in a subject receiving or in need of receiving IV fluid therapy, the method comprising administering to said subject a bioactive fluid composition comprising GND minimal and a physiologically acceptable carrier fluid, with GND electrolytes and/or AAE. By way of example only, the bioactive fluid composition administered may comprise some or all of the of the following components, for example within or close to the following levels: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. Another exemplary bioactive fluid composition that may be administered to promote the survival and/or proliferation of endothelial cells comprises some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered to promote the survival and/or proliferation of endothelial cells comprises some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered to promote the survival and/or proliferation of endothelial cells comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. A yet further exemplary bioactive fluid composition that may be administered to promote the survival and/or proliferation of endothelial cells comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

A further exemplary embodiment comprises a method of promoting the survival and/or proliferation of endothelial cells in a subject receiving or in need of receiving IV fluid therapy, the method comprising administering to said subject a bioactive fluid composition comprising GND Comp. Thus, an exemplary bioactive fluid composition may comprise some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered to promote the survival and/or proliferation of endothelial cells comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered to promote the survival and/or proliferation of endothelial cells comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), and/or derivatives thereof, in a physiologically acceptable carrier fluid. A yet further exemplary bioactive fluid composition that may be administered to promote the survival and/or proliferation of endothelial cells comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid.

For example, in some embodiments, bioactive fluid compositions that may be administered to promote the survival and/or proliferation of endothelial cells comprise some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

Additionally, bioactive fluid compositions according to the disclosure protect vascular integrity in vivo. The health of the endothelium is central to the function of the vasculature in the circulation of oxygen-carrying red blood cells, fluids, solutes, macromolecules, and cells to the organs and tissue of a subject. Vascular dysfunction and injury result in decreased blood flow to tissue and organs, decreased density of functional capillaries, impaired tissue oxygen perfusion, and extravasation and fluid accumulation in the interstitial tissues. As shown in Example 5, the bioactive fluid compositions described herein preserve the architecture and patency (openness) of the peripheral vasculature, whereas a standard-of-care crystalloid fluid (LR) resulted in peripheral vascular collapse, also known as vascular shock or shutdown, which is associated with poor clinical outcomes and increased risk of death.

Accordingly, another aspect of the disclosure relates to methods of protecting and/or preserving vascular integrity in a subject receiving or in need of receiving IV fluid therapy, the method comprising administering to said subject a bioactive fluid composition according to the disclosure. For example, an exemplary embodiment comprises a method of protecting and/or preserving vascular integrity in a subject receiving or in need of receiving IV fluid therapy, the method comprising administering to said subject a bioactive fluid composition comprising one or more amino acids, such as AAE, within or close to physiological levels. In an exemplary embodiment, the bioactive fluid composition administered comprises some or all of the following amino acids, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof. The bioactive fluid composition further comprises a physiologically acceptable carrier fluid, which may, for example, be water, or may be a crystalloid fluid such as those described herein, e.g. NS or LR. In some embodiments, the bioactive fluid composition comprises at least one amino acid chosen from serine, threonine, and/or derivatives thereof. For example, from 92-240 µmol/L of L-Threonine and/or from 56-140 µmol/L of L-Serine may be used. In various embodiments, the amino acid(s) present in the compositions comprise, consist essentially of, or consist of serine, threonine, and/or derivatives thereof.

Another exemplary embodiment comprises a method of protecting and/or preserving vascular integrity in a subject receiving or in need of receiving IV fluid therapy, the method comprising administering to said subject a bioactive fluid composition comprising a physiologically acceptable carrier fluid, GND electrolytes, and AAE. By way of example only, the bioactive fluid composition administered may comprise some or all of the of the following AAE and GND electrolytes, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof.

Another exemplary embodiment comprises a method of protecting and/or preserving vascular integrity in a subject receiving or in need of receiving IV fluid therapy, the method comprising administering to said subject a bioactive fluid composition comprising GND minimal and a physiologically acceptable carrier fluid, with GND electrolytes and/or AAE. By way of example only, the bioactive fluid composition administered may comprise some or all of the of the following components, for example within or close to the following levels: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. Another exemplary bioactive fluid composition that may be administered to protect and/or preserve vascular integrity comprises some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered to protect and/or preserve vascular integrity comprises some or all of the following components, for example within or close to the stated ranges: β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 μmol/L), L-Isoleucine (42-100 μmol/L), L-Leucine (66-170 μmol/L), L-Lysine (150-220 μmol/L), L-Methionine (16-30 μmol/L), L-Phenylalanine (41-68 μmol/L), L-Threonine (92-240 μmol/L), L-Tryptophan (25-150 μmol/L), L-Valine (150-310 μmol/L), and/or derivatives thereof, in a physiologically acceptable carrier fluid. A still further exemplary bioactive fluid composition that may be administered to protect and/or preserve vascular integrity comprises some or all of the following components, for example within or close to the stated ranges: L-Asparagine (40-150 μmol/L), L-Aspartic acid (0.1-10 μmol/L), L-Citrulline (16-55 μmol/L), L-Cysteine (30-65 μmol/L), L-Glutamic acid (18-98 μmol/L), Glycine (170-330 μmol/L), L-Proline (110-360 μmol/L), L-Tyrosine (45-74 μmol/L), β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. A yet further exemplary bioactive fluid composition that may be administered to protect and/or preserve vascular integrity comprises some or all of the following components, for example within or close to the stated ranges: L-Asparagine (40-150 μmol/L), L-Aspartic acid (0.1-10 μmol/L), L-Citrulline (16-55 μmol/L), L-Cysteine (30-65 μmol/L), L-Glutamic acid (18-98 μmol/L), Glycine (170-330 μmol/L), L-Proline (110-360 μmol/L), L-Tyrosine (45-74 μmol/L), β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), L-Histidine (26-120 μmol/L), L-Isoleucine (42-100 μmol/L), L-Leucine (66-170 μmol/L), L-Lysine (150-220 μmol/L), L-Methionine (16-30 μmol/L), L-Phenylalanine (41-68 μmol/L), L-Threonine (92-240 μmol/L), L-Tryptophan (25-150 μmol/L), L-Valine (150-310 μmol/L), and/or derivatives thereof, in a physiologically acceptable carrier fluid.

A further exemplary embodiment comprises a method of protecting and/or preserving vascular integrity in a subject receiving or in need of receiving IV fluid therapy, the method comprising administering to said subject a bioactive fluid composition comprising GND Comp. Thus, an exemplary bioactive fluid composition may comprise some or all of the following components, for example within or close to the stated ranges: L-Asparagine (40-150 μmol/L), L-Aspartic acid (0.1-10 μmol/L), L-Citrulline (16-55 μmol/L), L-Cysteine (30-65 μmol/L), L-Glutamic acid (18-98 μmol/L), Glycine (170-330 μmol/L), L-Proline (110-360 μmol/L), L-Tyrosine (45-74 μmol/L), L-Histidine (26-120 μmol/L), L-Isoleucine (42-100 μmol/L), L-Leucine (66-170 μmol/L), L-Lysine (150-220 μmol/L), L-Methionine (16-30 μmol/L), L-Phenylalanine (41-68 μmol/L), L-Threonine (92-240 μmol/L), L-Tryptophan (25-150 μmol/L), L-Valine (150-310 μmol/L), and/or derivatives thereof, in a physiologically acceptable carrier fluid. Yet another exemplary bioactive fluid composition that may be administered to protect and/or preserve vascular integrity comprises some or all of the following components, for example within or close to the stated ranges: L-Asparagine (40-150 μmol/L), L-Aspartic acid (0.1-10 μmol/L), L-Citrulline (16-55 μmol/L), L-Cysteine (30-65 μmol/L), L-Glutamic acid (18-98 μmol/L), Glycine (170-330 μmol/L), L-Proline (110-360 μmol/L), L-Tyrosine (45-74 μmol/L), chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 μmol/L), L-Isoleucine (42-100 μmol/L), L-Leucine (66-170 μmol/L), L-Lysine (150-220 μmol/L), L-Methionine (16-30 μmol/L), L-Phenylalanine (41-68 μmol/L), L-Threonine (92-240 μmol/L), L-Tryptophan (25-150 μmol/L), L-Valine (150-310 μmol/L), and/or derivatives thereof, in a physiologically acceptable carrier fluid. A still further exemplary bioactive fluid composition that may be administered to protect and/or preserve vascular integrity comprises some or all of the following components, for example within or close to the stated ranges: L-Asparagine (40-150 μmol/L), L-Aspartic acid (0.1-10 μmol/L), L-Citrulline (16-55 μmol/L), L-Cysteine (30-65 μmol/L), L-Glutamic acid (18-98 μmol/L), Glycine (170-330 μmol/L), L-Proline (110-360 μmol/L), L-Tyrosine (45-74 μmol/L), β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), and/or derivatives thereof, in a physiologically acceptable carrier fluid. A yet further exemplary bioactive fluid composition that may be administered to protect and/or preserve vascular integrity comprises some or all of the following components, for example within or close to the stated ranges: L-Asparagine (40-150 μmol/L), L-Aspartic acid (0.1-10 μmol/L), L-Citrulline (16-55 μmol/L), L-Cysteine (30-65 μmol/L), L-Glutamic acid (18-98 μmol/L), Glycine (170-330 μmol/L), L-Proline (110-360 μmol/L), L-Tyrosine (45-74 μmol/L), chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid.

For example, in some embodiments, bioactive fluid compositions that may be administered to protect and/or preserve vascular integrity comprise some or all of the following components, for example within or close to the stated ranges: L-Asparagine (40-150 μmol/L), L-Aspartic acid (0.1-10 μmol/L), L-Citrulline (16-55 μmol/L), L-Cysteine (30-65 μmol/L), L-Glutamic acid (18-98 μmol/L), Glycine (170-330 μmol/L), L-Proline (110-360 μmol/L), L-Tyrosine (45-74 μmol/L), β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

Bioactive fluid compositions according to the disclosure have also been shown to prevent or reduce extravasation in a subject receiving or in need of receiving IV fluid therapy. Intravenous fluids are known to leak during infusion, presumably due to increased vascular pressure from the infusion procedure and the need to maintain homeostasis following addition of fluid volume in a closed system. Fluid extravasation may also be triggered and/or exacerbated by the infusion of large volumes of standard-of-care crystalloid fluids, including NS and LR, that are frequently used in subjects requiring IV fluids for the purpose of resuscitative care, supportive care, and/or delivery of therapeutic, diagnostic, or other active agents. There is also evidence that injury to the vasculature results in extravasation. Common symptoms and signs of extravasation include pain, stinging or burning sensations, redness, and edema around the IV injection site. As a result of such extravasation, fluid accumulates in the surrounding tissues, causing edema. Interstitial edema is associated with increased risk of secondary injury to organs and tissues. Besides edema, fluid leakage IV therapy can result in damage to surrounding tissues, referred to as extravasation injuries. Extravasation injuries can range from small, superficial and reversible skin lesions to large full-thickness skin ulceration and damage to adjacent structures such as tendons, muscles, joints, and peripheral nerves.

As described above, it has been discovered that bioactive fluid compositions according to the disclosure protect the vasculature, prevent injury to the vasculature, and/or support repair of injured vasculature, which aids in avoiding or minimizing extravasation. As shown in Example 6, after infusion was completed, GND immediately arrested the leakage of albumin, whereas LR-treatment resulted in significant continuing leakage. These data demonstrate the capability of the bioactive fluid compositions described herein to protect vascular integrity, thus resulting in reduced fluid leakage from blood vessels in a manner not seen with standard-of-care crystalloid fluids, including NS and LR.

Accordingly, another aspect of the disclosure relates to methods of preventing or reducing extravasation in a subject receiving or in need of receiving IV fluid therapy, the method comprising administering to said subject a bioactive fluid composition according to the disclosure. For example, an exemplary embodiment comprises a method of preventing or reducing extravasation in a subject receiving or in need of receiving IV fluid therapy, the method comprising administering to said subject a bioactive fluid composition comprising one or more amino acids, such as AAE, within or close to physiological levels. In an exemplary embodiment, the bioactive fluid composition administered comprises some or all of the following amino acids, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof. The bioactive fluid composition further comprises a physiologically acceptable carrier fluid, which may, for example, be water, or may be a crystalloid fluid such as those described herein, e.g. NS or LR. In some embodiments, the bioactive fluid composition comprises at least one amino acid chosen from serine, threonine, and/or derivatives thereof. For example, from 92-240 µmol/L of L-Threonine and/or from 56-140 µmol/L of L-Serine may be used. In various embodiments, the amino acid(s) present in the compositions comprise, consist essentially of, or consist of serine, threonine, and/or derivatives thereof.

Another exemplary embodiment comprises a method of preventing or reducing extravasation in a subject receiving or in need of receiving IV fluid therapy, the method comprising administering to said subject a bioactive fluid composition comprising a physiologically acceptable carrier fluid, GND electrolytes, and AAE. By way of example only, the bioactive fluid composition administered may comprise some or all of the of the following AAE and GND electrolytes, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof.

Another exemplary embodiment comprises a method of preventing or reducing extravasation in a subject receiving or in need of receiving IV fluid therapy, the method comprising administering to said subject a bioactive fluid composition comprising GND minimal and a physiologically acceptable carrier fluid, with GND electrolytes and/or AAE. By way of example only, the bioactive fluid composition administered may comprise some or all of the of the following components, for example within or close to the following levels: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. Another exemplary bioactive fluid composition that may be administered to prevent or reduce extravasation comprises some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered to prevent or reduce extravasation comprises some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered to prevent or reduce extravasation comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. A yet further exemplary bioactive fluid composition that may be administered comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

A further exemplary embodiment comprises a method of preventing or reducing extravasation in a subject receiving or in need of receiving IV fluid therapy, the method comprising administering to said subject a bioactive fluid composition comprising GND Comp. Thus, an exemplary bioactive fluid composition may comprise some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered to prevent or reduce extravasation comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered to prevent or reduce extravasation comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), and/or derivatives thereof, in a physiologically acceptable carrier fluid. A yet further exemplary bioactive fluid composition that may be administered to prevent or reduce extravasation comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid.

For example, in some embodiments, bioactive fluid compositions that may be administered to prevent or reduce extravasation comprise some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120

μmol/L), L-Isoleucine (42-100 μmol/L), L-Leucine (66-170 μmol/L), L-Lysine (150-220 μmol/L), L-Methionine (16-30 μmol/L), L-Phenylalanine (41-68 μmol/L), L-Threonine (92-240 μmol/L), L-Tryptophan (25-150 μmol/L), L-Valine (150-310 μmol/L), and/or derivatives thereof, in a physiologically acceptable carrier fluid.

A further aspect relates to methods of administering a therapeutic, diagnostic, or active agent and/or reducing the effective dose or amount of a therapeutic, diagnostic, or active agent administered to a subject in need of such therapeutic, diagnostic, or active agent. In addition to edema and extravasation injuries, extravasation can decrease efficacy of IV therapies. For example, when standard-of-care crystalloid fluids are used as carriers for administering therapeutics, diagnostics, or other active agents, the extravasation of such fluids may also result in the extravasation of the therapeutics, diagnostics, or active agents which they carry. As a result, either a lower-than-needed dose is delivered, or a greater-than-needed dose is required to offset the amount lost to extravasation. Further, in some cases, leakage of injected drugs from blood vessels into surrounding tissue causes damage to the tissues exposed to the drug. However, because the bioactive fluid compositions according to the disclosure avoid or minimize extravasation, they are useful as diluents or carriers for the administration of active agents such as antibiotics, therapeutics such as chemotherapy agents or radioligands, diagnostics such as contrast agents or radioligands, or IV administered nutritional supplementation such as glucose supplementation. In particular, and because they result in less extravasation compared to NS or LR, the use of bioactive fluid compositions according to the disclosure enables the use of lower concentrations of the therapeutics, diagnostics, or active agents. In other words, the effective dose can be lowered, as the loss due to extravasation will be lowered. Use of bioactive fluid compositions according to the disclosure as the carrier for such therapeutics, diagnostics, or active agents permits the effective dose of said agents to be reduced with corresponding reduction in adverse or off-target effects. Similarly, reduction or prevention of extravasation can increase the efficacy of said agents by increasing the targeting of their distribution.

Thus, the disclosure further relates to methods of administering a therapeutic, diagnostic, or active agent and/or reducing the effective dose or amount of a therapeutic, diagnostic, or active agent administered to a subject, the method comprising administering to said subject a bioactive fluid composition according to the disclosure, wherein the bioactive fluid composition further comprises at least one therapeutic, diagnostic, and/or active agent. For example, an exemplary embodiment comprises a method of administering a therapeutic, diagnostic, or active agent and/or reducing the effective dose or amount of a therapeutic, diagnostic, or active agent administered to a subject, the method comprising administering to said subject a bioactive fluid composition comprising at least one therapeutic, diagnostic, and/or active agent, and one or more amino acids, such as AAE, within or close to physiological levels. In an exemplary embodiment, the bioactive fluid composition administered comprises at least one therapeutic, diagnostic, and/or active agent and some or all of the following amino acids, for example within or close to the following levels: L-Histidine (26-120 μmol/L), L-Isoleucine (42-100 μmol/L), L-Leucine (66-170 μmol/L), L-Lysine (150-220 μmol/L), L-Methionine (16-30 μmol/L), L-Phenylalanine (41-68 μmol/L), L-Threonine (92-240 μmol/L), L-Tryptophan (25-150 μmol/L), L-Valine (150-310 μmol/L), and/or derivatives thereof. The bioactive fluid composition further comprises a physiologically acceptable carrier fluid, which may, for example, be water, or may be a crystalloid fluid such as those described herein, e.g. NS or LR, to which at least one therapeutic, diagnostic, and/or active agent has been added. In some embodiments, the bioactive fluid composition comprises at least one therapeutic, diagnostic, and/or active agent, and at least one amino acid chosen from serine, threonine, and/or derivatives thereof. For example, from 92-240 μmol/L of L-Threonine and/or from 56-140 μmol/L of L-Serine may be used. In various embodiments, the amino acid(s) present in the compositions comprise, consist essentially of, or consist of serine, threonine, and/or derivatives thereof.

Another exemplary embodiment comprises a method of administering a therapeutic, diagnostic, or active agent and/or reducing the effective dose or amount of a therapeutic, diagnostic, or active agent administered to a subject, the method comprising administering to said subject a bioactive fluid composition comprising a physiologically acceptable carrier fluid, at least one therapeutic, diagnostic, and/or active agent, GND electrolytes, and AAE. By way of example only, the bioactive fluid composition administered may comprise at least one therapeutic, diagnostic, and/or active agent and some or all of the of the following AAE and GND electrolytes, for example within or close to the following levels: L-Histidine (26-120 μmol/L), L-Isoleucine (42-100 μmol/L), L-Leucine (66-170 μmol/L), L-Lysine (150-220 μmol/L), L-Methionine (16-30 μmol/L), L-Phenylalanine (41-68 μmol/L), L-Threonine (92-240 μmol/L), L-Tryptophan (25-150 μmol/L), L-Valine (150-310 μmol/L), chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof.

Another exemplary embodiment comprises a method of administering a therapeutic, diagnostic, or active agent and/or reducing the effective dose or amount of a therapeutic, diagnostic, or active agent administered to a subject, the method comprising administering to said subject a bioactive fluid composition comprising at least one therapeutic, diagnostic, and/or active agent, GND minimal, and a physiologically acceptable carrier fluid, further comprising GND electrolytes and/or AAE. By way of example only, the bioactive fluid composition may comprise at least one therapeutic, diagnostic, and/or active agent and some or all of the of the following components, for example within or close to the following levels: β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), chloride (95-115 mmol/L), sodium (115-150 mmol/L), copper (5-24 μmol/L), zinc (15-70 μmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. Another exemplary bioactive fluid composition for use in such methods comprises at least one therapeutic, diagnostic, and/or active agent and some or all of the following components, for example within or close to the stated ranges: β-Alanine (200-600 μmol/L), L-Arginine (10-70 μmol/L), L-Glutamine (390-650 μmol/L), L-Ornithine (27-80 μmol/L), L-Serine (56-140 μmol/L), L-Taurine (45-440 μmol/L), Vitamin B6 (30-144 nmol/L), folic acid (5-250 nmol/L), Vitamin C (11-120 μmol/L), glucose (3-25 mmol/L), L-Histidine (26-

120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition for use in such methods comprises at least one therapeutic, diagnostic, and/or active agent and some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered to of deliver a therapeutic, diagnostic, or active agent and/or reduce the effective dose or amount of a therapeutic, diagnostic, or active agent comprises at least one therapeutic, diagnostic, and/or active agent and some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. A yet further exemplary bioactive fluid composition that may be administered in such methods comprises at least one therapeutic, diagnostic, and/or active agent and some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

A further exemplary embodiment comprises methods of administering a therapeutic, diagnostic, or active agent and/or reducing the effective dose or amount of a therapeutic, diagnostic, or active agent administered to a subject, the methods comprising administering to said subject a bioactive fluid composition comprising at least one therapeutic, diagnostic, and/or active agent, and GND Comp. Thus, an exemplary bioactive fluid composition for use in such methods may comprise at least one therapeutic, diagnostic, and/or active agent and some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered for use in such methods comprises at least one therapeutic, diagnostic, and/or active agent and some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered for use in such methods comprises at least one therapeutic, diagnostic, and/or active agent and some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), and/or derivatives thereof, in a physiologically acceptable carrier fluid. A yet further exemplary bioactive fluid composition that may be administered to deliver a therapeutic, diagnostic, or active agent and/or reduce the effective dose or amount of a therapeutic, diagnostic, or active agent comprises at least one therapeutic, diagnostic, and/or active agent and some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid.

For example, in some embodiments, bioactive fluid compositions that may be administered to deliver a therapeutic, diagnostic, or active agent and/or to reduce the effective dose or amount of a therapeutic, diagnostic, or active agent comprise at least one therapeutic, diagnostic, and/or active agent and some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 mol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

A further aspect relates to methods of preserving tissue oxygen perfusion in a subject receiving or in need of receiving IV fluid therapy. There is evidence that injury to the vasculature and/or the leakage of fluid into the surrounding tissues, including leakage of IV crystalloid fluid used to treat serious illness or injury, significantly reduces peripheral tissue oxygen perfusion. Accordingly, bioactive fluid compositions described herein that prevent injury to the vasculature, protect or support the repair of injured vasculature, and prevent or reduce extravasation, are also useful in preservation of tissue oxygen perfusion. As is shown in Example 7 herein, withdrawal of 50% of the oxygen-carrying blood from rats reduced baseline tissue oxygen perfusion by an equivalent fraction (50%). Transfusion with GND maintained tissue oxygen perfusion within this baseline range (40-60%), whereas tissue oxygen perfusion continued to decline in LR-treated animals to a nadir of approximately 20%. These data demonstrate the capability of bioactive fluid compositions according to the disclosure to protect vascular integrity and function through the continued effective circulation of life-sustaining oxygen-carrying blood in a manner not seen with standard-of-care crystalloid fluids including NS and LR.

Accordingly, another aspect of the disclosure relates to methods of preserving tissue oxygen perfusion in a subject receiving or in need of receiving IV fluid therapy, the method comprising administering to said subject a bioactive fluid composition according to the disclosure. For example, an exemplary embodiment comprises a method of preserving tissue oxygen perfusion in a subject receiving or in need of receiving IV fluid therapy, the method comprising administering to said subject a bioactive fluid composition comprising one or more amino acids, such as AAE, within or close to physiological levels. In an exemplary embodiment, the bioactive fluid composition administered comprises some or all of the following amino acids, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof. The bioactive fluid composition further comprises a physiologically acceptable carrier fluid, which may, for example, be water, or may be a crystalloid fluid such as those described herein, e.g. NS or LR. In some embodiments, the bioactive fluid composition comprises at least one amino acid chosen from serine, threonine, and/or derivatives thereof. For example, from 92-240 µmol/L of L-Threonine and/or from 56-140 µmol/L of L-Serine may be used. In various embodiments, the amino acid(s) present in the compositions comprise, consist essentially of, or consist of serine, threonine, and/or derivatives thereof.

Another exemplary embodiment comprises a method of preserving tissue oxygen perfusion in a subject receiving or in need of receiving IV fluid therapy, the method comprising administering to said subject a bioactive fluid composition comprising a physiologically acceptable carrier fluid, GND electrolytes, and AAE. By way of example only, the bioactive fluid composition administered may comprise some or all of the of the following AAE and GND electrolytes, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof.

Another exemplary embodiment comprises a method of preserving tissue oxygen perfusion in a subject receiving or in need of receiving IV fluid therapy, the method comprising administering to said subject a bioactive fluid composition comprising GND minimal and a physiologically acceptable carrier fluid, with GND electrolytes and/or AAE. By way of example only, the bioactive fluid composition administered may comprise some or all of the of the following components, for example within or close to the following levels: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. Another exemplary bioactive fluid composition that may be administered to preserve tissue oxygen perfusion comprises some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220

µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered to preserve tissue oxygen perfusion comprises some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered to preserve tissue oxygen perfusion comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. A yet further exemplary bioactive fluid composition that may be administered to preserve tissue oxygen perfusion comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

A further exemplary embodiment comprises a method of preserving tissue oxygen perfusion in a subject receiving or in need of receiving IV fluid therapy, the method comprising administering to said subject a bioactive fluid composition comprising GND Comp. Thus, an exemplary bioactive fluid composition may comprise some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered to preserve tissue oxygen perfusion comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered to preserve tissue oxygen perfusion comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), and/or derivatives thereof, in a physiologically acceptable carrier fluid. A yet further exemplary bioactive fluid composition that may be administered to preserve tissue oxygen perfusion comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid.

For example, in some embodiments, bioactive fluid compositions that may be administered to preserve tissue oxygen perfusion comprise some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-

70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

Still further aspects relate to improving and/or normalizing physiological and/or metabolic markers of clinical outcome, improving survival time, and/or reducing morbidity in a subject with serious injury and/or illness, e.g. traumatic injury, hemorrhage, and/or hemorrhagic shock. Such conditions are associated with vascular dysregulation and damage, extravasation and edema, impaired tissue oxygen perfusion, and significant changes in key physiological (heart rate and blood pressure) and metabolic (pH, base deficit, glucose, and lactate) parameters. However, as described herein, bioactive fluid compositions according to the disclosure protect vascular integrity and function in vivo, and reduce or prevent the adverse consequences that arise from infusion of standard-of-care crystalloid fluids such as NS or LR, in particular fluid extravasation, edema, reduced tissue oxygen perfusion. As a result, administration of bioactive fluid compositions according to the disclosure improves clinical outcomes in seriously ill or injured subjects, for example subjects with traumatic injury, hemorrhage, and/or hemorrhagic shock, as measured by physiological and metabolic parameters.

Additionally, serious illness and/or injury, particularly involving blood volume loss, are associated with markedly increased heart rate (tachycardia). Prolonged tachycardia can disrupt normal cardiac function and lead to life-threatening complications including cardiac arrest and/or failure, stroke, or death. To compensate for blood volume loss, heart rate is elevated in an attempt to maintain blood pressure and adequate perfusion of central organs and tissues (e.g. brain, heart, lungs). As described in Example 8 below, administration of bioactive fluid compositions according to the disclosure rapidly normalized heart rate in standard animal models experiencing serious hemorrhage and shock, whereas as the standard-of-care crystalloid (NS and LR) resulted in tachycardia.

In addition, bioactive fluid compositions according to the disclosure achieve the primary goals of IV fluid therapy, specifically increased blood volume and blood pressure. Mean arterial pressure (MAP) is the average arterial blood pressure and is used to guide the use of fluids for resuscitation. Current guidelines advocate the use of fluids to achieve a MAP of 90 mmHg in order to maintain central perfusion to critical organs. A higher MAP during resuscitation means that less fluid is needed to achieve the target MAP and improve clinical outcomes. As described in Example 8, administration of bioactive fluid compositions according to the disclosure provided a significant increase in MAP over standard-of-care crystalloid fluids, including NS and LR, when used for resuscitation following hemorrhage and shock. These studies also indicate that resuscitation with bioactive fluid compositions according to the disclosure produced the same MAP as standard-of-care crystalloid fluid, but with 50% of the volume. Accordingly, a smaller volume of bioactive fluid compositions such as GND may be used for resuscitation which, in turn, may reduce the potential for dilutional and other adverse side-effects of crystalloid resuscitation, including extravasation.

Further, and as also described in Example 8, bioactive fluid compositions according to the disclosure have been shown, in in-vivo models, to result in significant improvements in metabolic markers of hemorrhagic shock (pH, base deficit, glucose, and lactate). Base deficit or base excess is a calculation of how much base is in the blood. Typically, the amount of base is neutral with values near zero (neither too much or too little). This measure can be used to determine if any acid/base imbalance exists due to different factors such as respiratory problems, hemorrhage, etc. Base deficit has been shown to be associated with poor trauma outcomes and increased risk of multi-organ failure and death. Correction of base deficit by bioactive fluid compositions according to the disclosure is therefore expected to lead to improved patient outcomes. As Example 8 shows, a single infusion of a bioactive fluid composition immediately improved critical metabolic markers of clinical outcome, and continued to provide beneficial effects for at least two hours following infusion. The bioactive fluid compositions can therefore stabilize subjects presenting with serious illness or injury more quickly and effectively than standard-of-care fluids, including NS and LR. More rapid and effective stabilization of such patients will result in less time and treatment costs in emergency services and hospitals, and reduced risk of morbidity and mortality.

Additionally, at the cellular level, serious injury and/or illness are associated with hypermetabolism and altered carbohydrate, protein, and lipid metabolism, and infusion of large volumes of crystalloid fluids results in hemodilution and further reduces already depleted energy stores, nutrients, and metabolites that support cell survival, metabolism, and repair. Tissues and organs subject to stress and injury, including from moderate to severe blood loss, are better able to survive, recover, and function with bioactive fluid compositions according to the disclosure which replace depleted nutrients, microminerals, and metabolites, and which also provide energy sources to support metabolism. As shown in Example 8, the bioactive fluid compositions described herein result in significantly improved cellular, metabolic, and physiological function, particularly in response to cellular stress, blood volume loss, and shock, and also avoid or prevent the dysfunction and/or adverse effects induced by standard-of-care fluids, thus resulting in improved outcomes and survival. The data demonstrate that administration of a bioactive fluid composition according to the disclosure resulted in significantly increased overall survival in a standard animal model of serious hemorrhage and shock, compared to the standard-of-care crystalloid fluid NS.

Figure 9:
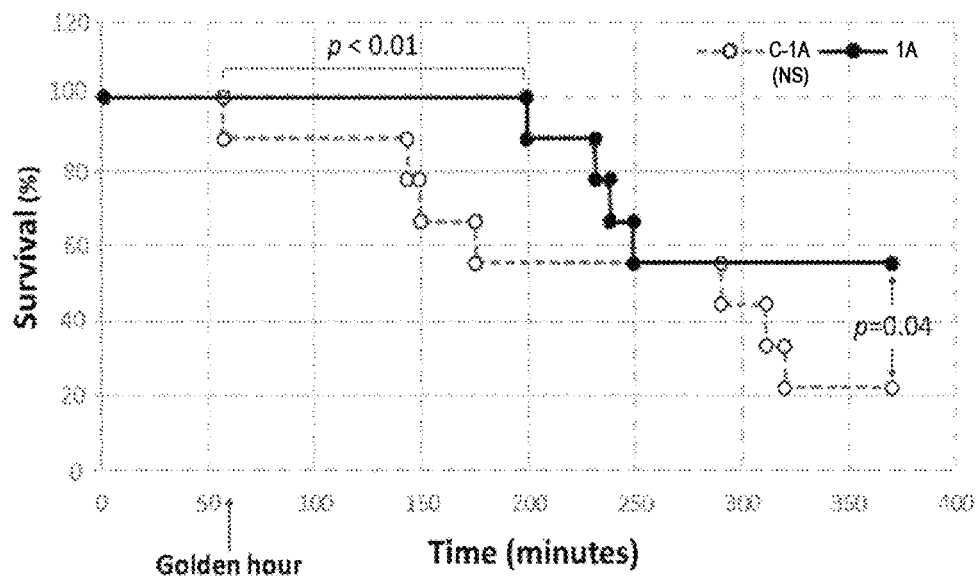
FIG. 9 depicts the effect of bioactive fluid compositions according to the disclosure on survival of Sprague-Dawley rats using a well-defined model of blood volume loss (hemorrhage) and shock, demonstrating that the bioactive fluid compositions significantly increased the time to first death by 3-fold (i.e., the effective window for evacuation and provision of definitive medical care, p<0.01) and overall survival (p<0.01) compared to the standard-of-care crystalloid fluid (NS).

Further, bioactive fluid compositions according to the disclosure increase minimum survival time. In cases of life-threatening traumatic injury, it is known that the first hour after injury, known as the "Golden Hour," is a critical period for receiving appropriate medical and surgical intervention. However, it is not always possible for a trauma patient to receive the treatment needed during this critical first hour. Thus, methods that extend the window in which needed medical and/or surgical intervention can be provided has the ability to prevent serious morbidity or mortality following traumatic injury. As Example 8 and FIG. 9 show, bioactive fluid compositions of the disclosure prolong the "Golden Hour" window by more than three-fold, thus improving survival and reducing morbidity following traumatic injury, hemorrhage, and/or shock.

Accordingly, another aspect of the disclosure relates to methods of improving and/or normalizing physiological and/or metabolic markers of clinical outcome, improving survival time, and/or reducing morbidity in a subject with serious injury and/or illness, the method comprising administering to said subject a bioactive fluid composition according to the disclosure. For example, an exemplary embodiment comprises a method of improving and/or normalizing physiological and/or metabolic markers of clinical outcome, improving survival time, and/or reducing morbidity in a subject with serious injury and/or illness, the method comprising administering to said subject a bioactive fluid composition comprising one or more amino acids, such as AAE, within or close to physiological levels. In an exemplary embodiment, the bioactive fluid composition administered comprises some or all of the following amino acids, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof. The bioactive fluid composition further comprises a physiologically acceptable carrier fluid, which may, for example, be water, or may be a crystalloid fluid such as those described herein, e.g. NS or LR. In some embodiments, the bioactive fluid composition comprises at least one amino acid chosen from serine, threonine, and/or derivatives thereof. For example, from 92-240 µmol/L of L-Threonine and/or from 56-140 µmol/L of L-Serine may be used. In various embodiments, the amino acid(s) present in the compositions comprise, consist essentially of, or consist of serine, threonine, and/or derivatives thereof.

Another exemplary embodiment comprises a method of improving and/or normalizing physiological and/or metabolic markers of clinical outcome, improving survival time, and/or reducing morbidity in a subject with serious injury and/or illness, the method comprising administering to said subject a bioactive fluid composition comprising a physiologically acceptable carrier fluid, GND electrolytes, and AAE. By way of example only, the bioactive fluid composition administered may comprise some or all of the of the following AAE and GND electrolytes, for example within or close to the following levels: L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof.

Another exemplary embodiment comprises a method of improving and/or normalizing physiological and/or metabolic markers of clinical outcome, improving survival time, and/or reducing morbidity in a subject with serious injury and/or illness, the method comprising administering to said subject a bioactive fluid composition comprising GND minimal and a physiologically acceptable carrier fluid, with GND electrolytes and/or AAE. By way of example only, the bioactive fluid composition administered may comprise some or all of the of the following components, for example within or close to the following levels: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. Another exemplary bioactive fluid composition that may be administered to improve and/or normalize physiological and/or metabolic markers of clinical outcome, improve survival time, and/or reduce morbidity in a subject with serious injury and/or illness comprises some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered to improve and/or normalize physiological and/or metabolic markers of clinical outcome, improve survival time, and/or reduce morbidity in a subject with serious injury and/or illness comprises some or all of the following components, for example within or close to the stated ranges: β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered to improve and/or normalize physiological and/or metabolic markers of clinical outcome, improve survival time, and/or reduce morbidity in a subject with serious injury and/or illness comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid. A yet further exemplary bioactive fluid composition that may be administered to improve and/or normalize physiological and/or metabolic markers of clinical outcome, improve survival time, and/or reduce morbidity in a subject with serious injury and/or illness comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

A further exemplary embodiment comprises a method of improving and/or normalizing physiological and/or metabolic markers of clinical outcome, improving survival time, and/or reducing morbidity in a subject with serious injury and/or illness, the method comprising administering to said subject a bioactive fluid composition comprising GND Comp. Thus, an exemplary bioactive fluid composition may comprise some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. Yet another exemplary bioactive fluid composition that may be administered to improve and/or normalize physiological and/or metabolic markers of clinical outcome, improve survival time, and/or reduce morbidity in a subject with serious injury and/or illness comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid. A still further exemplary bioactive fluid composition that may be administered to improve and/or normalize physiological and/or metabolic markers of clinical outcome, improve survival time, and/or reduce morbidity in a subject with serious injury and/or illness comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 µmol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), and/or derivatives thereof, in a physiologically acceptable carrier fluid. A yet further exemplary bioactive fluid composition that may be administered to improve and/or normalize physiological and/or metabolic markers of clinical outcome, improve survival time, and/or reduce morbidity in a subject with serious injury and/or illness comprises some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), and/or derivatives thereof, in a physiologically acceptable carrier fluid.

For example, in some embodiments, bioactive fluid compositions that may be administered to improve and/or normalize physiological and/or metabolic markers of clinical outcome, improve survival time, and/or reduce morbidity in a subject with serious injury and/or illness comprise some or all of the following components, for example within or close to the stated ranges: L-Asparagine (40-150 µmol/L), L-Aspartic acid (0.1-10 µmol/L), L-Citrulline (16-55 µmol/L), L-Cysteine (30-65 µmol/L), L-Glutamic acid (18-98 µmol/L), Glycine (170-330 µmol/L), L-Proline (110-360 µmol/L), L-Tyrosine (45-74 µmol/L), β-Alanine (200-600 µmol/L), L-Arginine (10-70 µmol/L), L-Glutamine (390-650 mol/L), L-Ornithine (27-80 µmol/L), L-Serine (56-140 µmol/L), L-Taurine (45-440 µmol/L), Vitamin B6 (30-144 nmol/L), folic acid (5-250 nmol/L), Vitamin C (11-120 µmol/L), glucose (3-25 mmol/L), chloride (95-115 mmol/L), sodium (115-150 mmol/L), copper (5-24 µmol/L), zinc (15-70 µmol/L), magnesium (0.2-1.0 mmol/L), phosphate (0.8-2 mmol/L), potassium (2-5 mmol/L), acetate (2-45 mmol/L), pyruvate (0.03-2.5 mmol/L), malic acid (1-15 mmol/L), L-Histidine (26-120 µmol/L), L-Isoleucine (42-100 µmol/L), L-Leucine (66-170 µmol/L), L-Lysine (150-220 µmol/L), L-Methionine (16-30 µmol/L), L-Phenylalanine (41-68 µmol/L), L-Threonine (92-240 µmol/L), L-Tryptophan (25-150 µmol/L), L-Valine (150-310 µmol/L), and/or derivatives thereof, in a physiologically acceptable carrier fluid.

An exemplary and non-limiting method according to the disclosure is a method for improving at least one outcome in a subject receiving or in need of receiving IV fluid therapy for resuscitative or supportive therapy, or for delivery of therapeutic agents, diagnostic agents, and/or active agents, the method comprising administering to said subject a bioactive fluid composition according to the disclosure, where the outcome improved is survival, reduced extravasation, and/or enhanced tissue perfusion compared to administration of NS or LR. Optionally, the bioactive fluid composition comprises at least one amino acid chosen from serine, threonine, and/or derivatives thereof, and at least one additional component chosen from electrolytes, buffering agents, antioxidants, energy sources, cofactors, blood pressure stabilizers, and/or amino acids other than serine, threonine, and/or derivatives thereof.

A further exemplary and non-limiting method according to the disclosure is a method for improving at least one outcome in a subject that has experienced fluid loss, the method comprising administering to said subject a bioactive fluid composition according to the disclosure, where the outcome improved is survival, reduced extravasation, and/or enhanced tissue perfusion compared to administration of NS or LR. Optionally, the bioactive fluid composition comprises at least one amino acid chosen from serine, threonine, and/or derivatives thereof, and at least one additional component chosen from electrolytes, buffering agents, antioxidants, energy sources, cofactors, blood pressure stabilizers, and/or amino acids other than serine, threonine, and/or derivatives thereof.

A yet further exemplary and non-limiting method according to the disclosure is a method for treating a subject in need of IV fluid therapy, the method comprising administering to said subject a bioactive fluid composition according to the disclosure. Optionally, the bioactive fluid composition comprises at least one amino acid chosen from serine, threonine, and/or derivatives thereof, and at least one additional component chosen from electrolytes, buffering agents, antioxidants, energy sources, cofactors, blood pressure stabilizers, and/or amino acids other than serine, threonine, and/or derivatives thereof.

A still further exemplary and non-limiting method according to the disclosure is a method for replacing fluids in a subject in need of fluid replacement, the method comprising administering to said subject a bioactive fluid composition according to the disclosure. Optionally, the bioactive fluid composition comprises at least one amino acid chosen from serine, threonine, and/or derivatives thereof, and at least one additional component chosen from electrolytes, buffering agents, antioxidants, energy sources, cofactors, blood pressure stabilizers, and/or amino acids other than serine, threonine, and/or derivatives thereof. The need for fluid replacement may, for example, be due to blood loss, paracentesis, and/or dehydration.

An even further exemplary and non-limiting method according to the disclosure is a method for improving at least one outcome in a subject receiving or in need of receiving IV fluid therapy for resuscitative or supportive therapy, or for delivery of therapeutic agents, diagnostic agents, and/or active agents, where the outcome improved is survival, reduced extravasation, and/or enhanced tissue perfusion compared to administration of NS or LR, the method comprising administering to said subject a means for improving said outcome. Any of the bioactive fluid compositions described herein are suitable means for achieving such outcome.

A still further exemplary and non-limiting method according to the disclosure is a method for improving at least one outcome in a subject that has experienced fluid loss, where the outcome improved is survival, reduced extravasation, and/or enhanced tissue perfusion compared to administration of NS or LR, the method comprising administering to said subject a means for improving said outcome. Any of the bioactive fluid compositions described herein are suitable means for achieving such outcome.

A further exemplary and non-limiting method according to the disclosure is a method for treating a subject in need of IV fluid therapy and/or a method for replacing fluids in a subject in need of fluid replacement, the method comprising administering to said subject a means for improving said outcome. Any of the bioactive fluid compositions described herein are suitable means for treating said patient and/or replacing said fluids. The need for fluid replacement may, for example, be due to blood loss, paracentesis, and/or dehydration.

Any of the aforementioned methods may be employed in resuscitative and/or supportive care situations where crystalloid fluids are warranted, or in delivery of therapeutics, diagnostics, or other active agents. Without wishing to be bound by theory, the bioactive fluid compositions according to the disclosure are believed to mix freely with blood without creating precipitates of inorganic, organic, and/or cellular nature, which aggregates could occlude small vessels directly or indirectly by inducing larger aggregates to form. Nevertheless, in various embodiments, the bioactive fluid compositions are not administered concurrently with compositions comprising blood components or blood products, proteins, antibodies, immunoreactive substances, colloids or oncotic substances, or oxygen-carriers.

The bioactive fluid compositions may be used in accordance with standard practice for IV fluids. They may be used as a fixed volume bolus, for example one liter, or as an initial bolus to achieve a target blood pressure and then as a drip to maintain that blood pressure. The maximum dose will be based on age, weight, clinical condition, and if possible, laboratory tests, such as arterial blood gas. The bioactive fluid compositions can be used as IV fluids in any situation where an IV administration is employed.

By way of non-limiting example, the bioactive fluid compositions may find use in the prehospital setting (e.g. on-site to stabilize a patient before transport or enroute to the hospital) and in-hospital settings to address loss of blood volume. As further examples, he bioactive fluid compositions can also be used in a variety of surgical settings and procedures, and in instances where blood or blood products are not indicated for use, are unavailable, or cannot be used due to prior sensitization or transfusion reactions, infectious disease risk, or religious and/or cultural reasons. As further examples still, the bioactive fluid compositions may find use as a resuscitation fluid for serious illness or injury, including burn injuries, dehydration, and sepsis, or in treatment of traumatic brain injuries or resuscitation following trauma.

The bioactive fluid compositions may also be used in the field for replacement of blood volume loss due to hemorrhage. Advantageously, because bioactive fluid compositions according to the disclosure result in less extravasation than standard-of-care fluids, the compositions will be used at lower levels, e.g. a level of only one-half to three times the amount of blood lost. During the first 24 hours after a traumatic event involving blood loss, the body is in a hypometabolic state as the body attempts to conserve oxygen and energy stores. As the body recovers from such events, it switches to a hypermetabolic state, breaking down fat and muscle stores for energy. Thus, in some embodiments the bioactive fluid compositions are used to provide metabolites, i.e., nutrient and energy supplies for the body during the hypometabolic phase to hasten recovery, and also when it switches into a hypermetabolic state to avoid auto-digestion. As described in the Examples below, the bioactive fluid compositions according to the disclosure have been shown to be effective physiological stabilizers, increasing blood pressure, normalizing heart rate, and reducing base deficit, thereby resulting in improved survival in a standard animal model of hemorrhage and shock.

As further examples, the bioactive fluid compositions may be used as a fluid replacement in a subject that has experienced severe trauma, bleeding, and the like. In another example, the bioactive fluid compositions can be used as a fluid replacement in dehydrated subjects. In another example, the bioactive fluid compositions can be used on the battlefield as a resuscitation fluid or for trauma application. Additionally, the bioactive fluid compositions can be used as an irrigation/flush solution for organs and tissues prior to transplantation, or as a tissue and organ preservation solution.

In still further examples, the bioactive fluid compositions can be used in mammals in veterinary settings, including treatment of serious illness or injury in assistance and working animals, including military dogs, thoroughbred horses, or other settings where fluid or blood loss may occur, in supportive care situations such as a fluid replacement for treating dehydration, or to deliver therapeutics, diagnostics, and/or active agents intravenously.

EXAMPLES

The following Examples are intended to be non-limiting and explanatory of various embodiments of the disclosure only.

The compositions used in the Examples were prepared with the following components, present in the amounts reported in Tables 1A-1B and 2A-2B (mean values, ±10%), unless otherwise specified. Compositions identified as "C-" indicate standard-of-care compositions, or variations thereof with additional components and amounts as specified.

TABLE 1A

CRYSTALLOID FLUID COMPOSITIONS-NORMAL SALINE

| Component | Amount (mg/L) | | | |
|---|---|---|---|---|
| | C-1A | C-1B | C-1C | C-1D |
| Sodium chloride | 9,000 | 9,000 | 9,000 | 9,000 |
| L-Alanyl-L-Glutamine | | | 109.40 | 109.40 |
| L-Arginine | | | 8.00 | 8.00 |
| L-Asparagine monohydrate | | | | 14.60 |
| L-Aspartic acid | | | | 0.40 |
| L-Citrulline | | | | 7.00 |
| L-Cysteine hydrochloride monohydrate | | | | 7.80 |
| L-Glutamic acid | | | | 9.00 |
| Glycine | | | | 19.00 |
| L-Histidine | | 12.50 | | 12.50 |
| L-Isoleucine | | 8.00 | | 8.00 |
| L-Leucine | | 13.00 | 13.00 | 13.00 |
| L-Lysine hydrochloride | | 32.48 | | 32.48 |
| L-Methionine | | 3.00 | | 3.00 |
| L-Ornithine monohydrochloride | | | 10.21 | 10.21 |
| L-Phenylalanine | | 6.00 | | 6.00 |
| L-Proline | | | | 23.00 |
| L-Serine | | | 10.00 | 10.00 |
| Taurine | | | 44.00 | 44.00 |
| L-Threonine | | 19.00 | | 19.00 |
| L-Tyrosine | | | | 9.00 |
| L-Tryptophan | | 14.28 | | 14.28 |
| L-Valine | | 23.00 | | 23.00 |
| Pyridoxine hydrochloride | | | 0.02 | 0.02 |
| Folic Acid | | | 0.10 | 0.10 |
| L-Ascorbic acid | | | 15.00 | 15.00 |
| D-Glucose | | 2,000.00 | 2,000.00 | 2,000.00 |
| Water | QS | QS | QS | QS |

TABLE 1B

CRYSTALLOID FLUID COMPOSITIONS-LACTATED RINGER'S

| Component | Amount (mg/L) | | | |
|---|---|---|---|---|
| | C-2A | C-2B | C-2C | C-2D |
| Sodium chloride | 6,000 | 6,000 | 6,000 | 6,000 |
| Sodium lactate | 3,100 | 3,100 | 3,100 | 3,100 |
| Potassium chloride | 300 | 300 | 300 | 300 |
| Calcium chloride | 200 | 200 | 200 | 200 |
| L-Alanyl-L-Glutamine | | | 109.40 | 109.40 |
| L-Arginine | | | 8.00 | 8.00 |
| L-Asparagine | | | | 14.60 |
| L-Aspartic acid | | | | 0.40 |
| L-Citrulline | | | | 7.00 |
| L-Cysteine hydrochloride monohydrate | | | | 7.80 |
| L-Glutamic acid | | | | 9.00 |
| Glycine | | | | 19.00 |
| L-Histidine | | 12.50 | | 12.50 |
| L-Isoleucine | | 8.00 | | 8.00 |
| L-Leucine | | 13.00 | 13.00 | 13.00 |
| L-Lysine hydrochloride | | 32.48 | | 32.48 |
| L-Methionine | | 3.00 | | 3.00 |
| L-Ornithine monohydrochloride | | | 10.21 | 10.21 |
| L-Phenylalanine | | 6.00 | | 6.00 |
| L-Proline | | | | 23.00 |
| L-Serine | | | 10.00 | 10.00 |
| Taurine | | | 44.00 | 44.00 |
| L-Threonine | | 19.00 | | 19.00 |
| L-Tyrosine | | | | 9.00 |
| L-Tryptophan | | 14.28 | | 14.28 |
| L-Valine | | 23.00 | | 23.00 |
| Pyridoxine hydrochloride | | | 0.02 | 0.02 |
| Folic Acid | | | 0.10 | 0.10 |
| L-Ascorbic acid | | | 15.00 | 15.00 |
| D-Glucose | | 2,000.00 | 2,000.00 | 2,000.00 |
| Water | QS | QS | QS | QS |

TABLE 2A

BIOACTIVE FLUID COMPOSITIONS

| Component | Amount (mg/L) | | | |
|---|---|---|---|---|
| | 1A | 1B | 1C | 1D |
| Sodium chloride | 5,804.00 | 5,804.00 | 5,804.00 | 5,804.00 |
| Copper chloride dihydrate | 1.55 | 1.55 | 1.55 | 1.55 |
| Zinc chloride | 3.42 | 3.42 | 3.42 | 3.42 |
| Magnesium chloride | 40.00 | 40.00 | 40.00 | 40.00 |
| Sodium phosphate monobasic monohydrate | 41.40 | 41.40 | 41.40 | 41.40 |
| Sodium phosphate dibasic | 170.30 | 170.30 | 170.30 | 170.30 |
| Potassium chloride | 223.00 | 223.00 | 223.00 | 223.00 |
| Sodium acetate | 2,500.00 | 2,500.00 | 2,500.00 | 2,500.00 |
| Sodium pyruvate | 110.00 | 110.00 | 110.00 | 110.00 |
| L-Malic acid | 67.10 | 67.10 | 67.10 | 67.10 |
| β-Alanine | | 35.00 | | |
| L-Alanyl-L-Glutamine | 109.40 | | | |
| L-Arginine | 8.00 | 8.00 | | |
| L-Asparagine monohydrate | 14.60 | 14.60 | | |
| L-Aspartic acid | 0.40 | 0.40 | | |
| L-Citrulline | 7.00 | 7.00 | | |
| L-Cysteine hydrochloride monohydrate | 7.80 | 7.80 | | |
| L-Glutamic acid | 9.00 | 9.00 | | |
| L-Glutamine | | 73.00 | | |
| Glycine | 19.00 | 19.00 | | |
| L-Histidine | 12.50 | 12.50 | | 12.50 |
| L-Isoleucine | 8.00 | 8.00 | | 8.00 |
| L-Leucine | 13.00 | 13.00 | | 13.00 |
| L-Lysine | | 26.00 | | |

TABLE 2A-continued

BIOACTIVE FLUID COMPOSITIONS

| Component | Amount (mg/L) | | | |
|---|---|---|---|---|
| | 1A | 1B | 1C | 1D |
| L-Lysine hydrochloride | 32.50 | | | 32.50 |
| L-Methionine | 3.00 | 3.00 | | 3.00 |
| L-Ornithine monohydrochloride | 10.20 | 10.20 | | |
| L-Phenylalanine | 6.00 | 6.00 | | 6.00 |
| L-Proline | 23.00 | 23.00 | | |
| L-Serine | 10.00 | 10.00 | | |
| Taurine | 44.00 | 44.00 | | |
| L-Threonine | 19.00 | 19.00 | | 19.00 |
| L-Tyrosine | 9.00 | 9.00 | | |
| L-Tryptophan | 14.30 | 14.30 | | 14.28 |
| L-Valine | 23.00 | 23.00 | | 23.00 |
| Vitamin B6 (Pyridoxine hydrochloride) | 0.017 | 0.017 | | |
| Folic Acid | 0.099 | 0.099 | | |
| L-Ascorbic acid | 15.00 | 15.00 | | |
| D-Glucose | 2,000.00 | 2,000.00 | 2,000.00 | 2,000.00 |
| Water | QS | QS | QS | QS |

TABLE 2B

BIOACTIVE FLUID COMPOSITIONS (CONT.)

| Component | Amount (mg/L) | | | |
|---|---|---|---|---|
| | 1E | 1F | 1G | 1H |
| Sodium chloride | 5,804.00 | 5,804.00 | 5,804.00 | 5,804.00 |
| Copper chloride dihydrate | 1.55 | 1.55 | 1.55 | 1.55 |
| Zinc chloride | 3.42 | 3.42 | 3.42 | 3.42 |
| Magnesium chloride | 40.00 | 40.00 | 40.00 | 40.00 |
| Sodium phosphate monobasic monohydrate | 41.40 | 41.40 | 41.40 | 41.40 |
| Sodium phosphate dibasic | 170.30 | 170.30 | 170.30 | 170.30 |
| Potassium chloride | 223.00 | 223.00 | 223.00 | 223.00 |
| Sodium acetate | 2,500.00 | 2,500.00 | 2,500.00 | 2,500.00 |
| Sodium pyruvate | 110.00 | 110.00 | 110.00 | 110.00 |
| L-Malic acid | 67.10 | 67.10 | 67.10 | 67.10 |
| L-Alanyl-L-Glutamine | 109.40 | 109.40 | 109.40 | 109.40 |
| L-Arginine | 8.00 | 8.00 | 8.00 | 8.00 |
| L-Asparagine monohydrate | | 14.60 | | |
| L-Aspartic acid | | 0.40 | | |
| L-Citrulline | | 7.00 | | 7.00 |
| L-Cysteine hydrochloride monohydrate | | 7.80 | | |
| L-Glutamic acid | | 9.00 | | |
| Glycine | | 19.00 | | |
| L-Histidine | | 12.50 | 12.50 | |
| L-Isoleucine | | 8.00 | 8.00 | |
| L-Leucine | 13.00 | 13.00 | 13.00 | |
| L-Lysine hydrochloride | | 32.48 | 32.48 | |
| L-Methionine | | 3.00 | 3.00 | |
| L-Ornithine monohydrochloride | 10.21 | 10.21 | 10.21 | 10.21 |
| L-Phenylalanine | | 6.00 | 6.00 | |
| L-Proline | | 23.00 | | |
| L-Serine | 10.00 | 10.00 | 10.00 | |
| Taurine | 44.00 | 44.00 | 44.00 | 44.00 |
| L-Threonine | | 19.00 | 19.00 | |
| L-Tyrosine | | 9.00 | | |
| L-Tryptophan | | 14.28 | 14.28 | |
| L-Valine | | 23.00 | 23.00 | |
| Pyridoxine hydrochloride | 0.02 | 0.02 | 0.02 | |
| Folic Acid | 0.10 | 0.10 | 0.10 | |
| L-Ascorbic acid | 15.00 | 15.00 | 15.00 | 15.00 |
| D-Glucose | 2,000.00 | 2,000.00 | 2,000.00 | 2,000.00 |
| Water | QS | QS | QS | QS |

Example 1: Effect of NS and LR on Endothelial Cell Viability

Method. The effect of NS and LR variants on the survival of primary vascular endothelial cells was evaluated in-vitro. Human umbilical vein endothelial cells (HUVECs) were removed from culture medium and growth factors, washed and then incubated in a) NS or b) LR, both with and without essential amino acids. Culture medium was used as the positive control c). HUVEC were incubated for 12 hours at 37° C. in a humidified atmosphere of 5% $CO_2$ in air. Viable cell numbers were determined by direct cell counting and trypan blue exclusion.

Results. HUVEC survival. As seen in FIG. 1, culture with NS (composition C-1A) or LR (composition C-2A) resulted in a loss (>10-fold) of viable HUVEC that was significant compared the starting number of cells (100,000 per well) and the media control (*, p<0.001). In contrast, culture media supported both viability and proliferation of HUVEC.

Results. Effect of Essential Amino Acids. Addition of essential amino acids (AAE) significantly improved the survival of HUVEC in NS (composition C-1B) or LR (composition C-2B) by 2-3-fold (p<0.05 and p<0.01, respectively), although overall cell numbers remained less than the starting number of cells (100,000 per well) and the media control (*p<0.001).

Example 2: Effect of Fluid Compositions on Endothelial Cell Viability

Method. The effect of bioactive fluid compositions according to the disclosure on endothelial cell viability was evaluated using the method described above and compared to the standard-of-care fluids (NS and LR).

Figure 2:
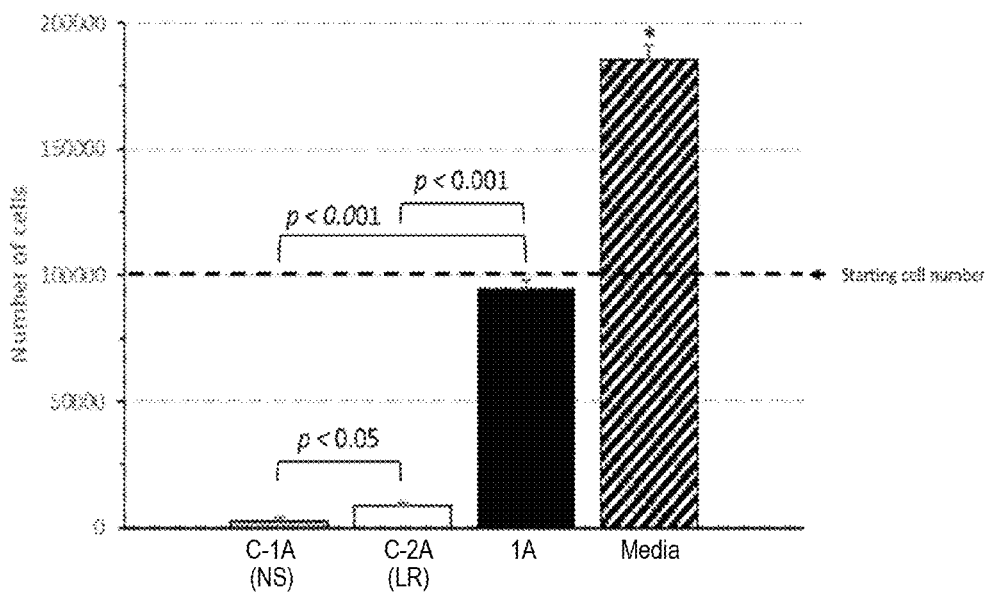
FIG. 2 depicts the evaluation of bioactive fluid compositions according to the disclosure on HUVEC mortality in vitro, demonstrating that the bioactive fluid compositions significantly improved HUVEC survival compared to standard-of-care crystalloid fluids (NS and LR).

Results. As seen in FIG. 2, composition 1C, with GND electrolytes, supported survival of approximately 95% of HUVECs, which was a significant improvement compared to NS (composition C-1A) or LR (composition C-2A) (p<0.001).

Figure 3:
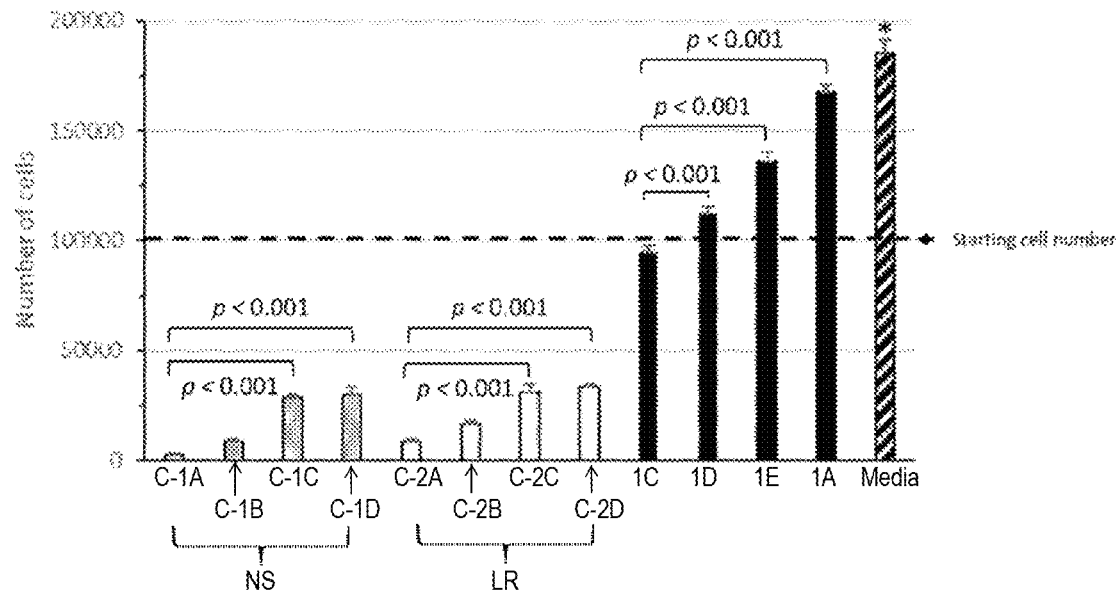
FIG. 3 depicts the effect of metabolites cofactors and energy sources in bioactive fluid compositions according to the disclosure on the viability of HUVEC compared to standard-of-care crystalloids (NS and LR).

As seen in FIG. 3 the addition of essential amino acids (composition 1D) significantly improved the survival of HUVEC relative to composition 1C (p<0.01) and allowed for a small increase in HUVEC number (i.e., proliferation). Composition 1D supported 100% HUVEC survival, and proliferation increased the starting cell number by 12.5%. These results demonstrate that composition 1D with GND electrolytes and amino acids is a superior fluid compared to NS and LR with addition of the same amino acids (compositions C-1B and C-2B, respectively) (p<0.001).

As seen in FIG. 3, composition 1E with GND minimal further improved survival of HUVEC relative to composition 1C (p<0.001). This improvement is even greater compared to NS and LR, even with addition of the same components (compositions C-1C and C-2C, respectively). FIG. 3 also shows that composition 1E supported 100% HUVEC survival and proliferation increased the starting cell number by 36%. These results demonstrate that composition 1E is a superior fluid compared to NS and LR with addition of the same components (compositions C-1C and C-2C, respectively) (p<0.001).

As seen in FIG. 3, composition 1A with GND complete further improved survival of HUVEC relative to composition 1C (p<0.001). This improvement is even greater compared to NS and LR, even with addition of the same components (compositions C-1D and C-2D, respectively). FIG. 3 also shows that composition 1A supported 100% HUVEC survival, and proliferation increased the starting cell number by 68%. These results demonstrate that composition 1A is a superior fluid compared to NS and LR with addition of the same components (compositions C-1D and C-2D, respectively) (p<0.001).

Combined, these data show that bioactive fluid compositions according to the disclosure supported the survival, viability, and proliferation of vascular endothelial cells. In contrast, the standard-of-care fluids, NS and LR, showed little to no capacity to support, protect, or promote endothelial cell survival, viability, and proliferation.

Example 3: Effect on Endothelial Glycocalyx Shedding

This example examined the effect of bioactive fluid compositions according to the disclosure on the endothelial glycocalyx, a layer of glycoproteins and proteoglycans lining the vascular endothelium which serves as a regulator of vascular permeability. Serious illness and/or injury damages the vascular endothelium and this is characterized by shedding of the glycocalyx glycoprotein, Syndecan-1. The concentration of Syndecan-1 was measured in culture supernatants following exposure to composition 1A, or the standard-of-care fluid, NS (composition C-1A). HUVEC were cultured in endothelial growth media (EGM-2, Lonza) at 37° C. in a humidified atmosphere of 5% $CO_2$ in air until approximately 70% confluent. The culture medium and growth factors were then removed and replaced with equivalent volumes of composition C-1A, composition 1A, or fresh culture medium, and the cells were returned to the incubator. After 4 hours, culture supernatants were collected and assayed by ELISA for the presence of Syndecan-1 (LS Bio).

Figure 4:
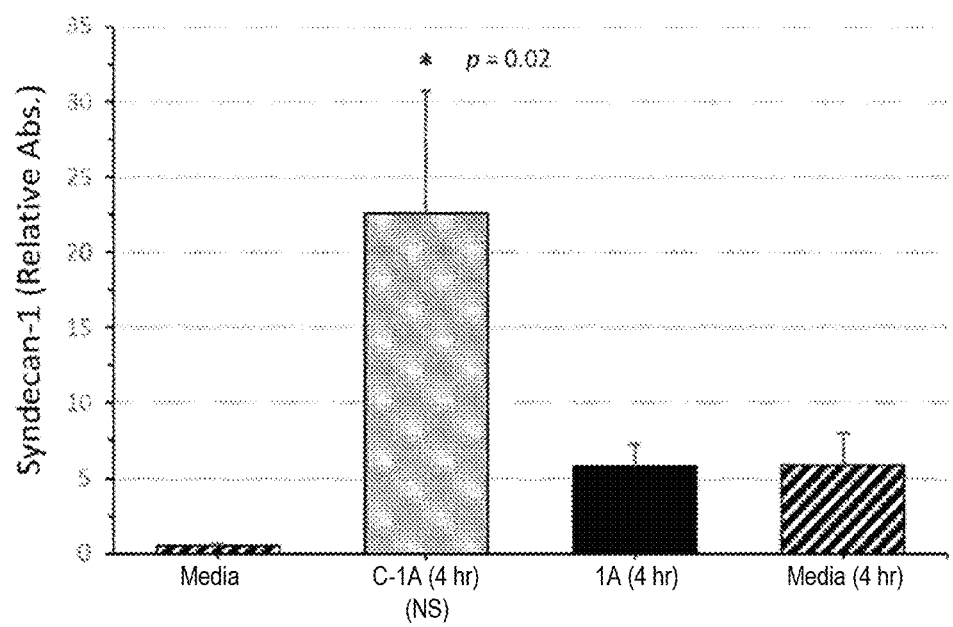
FIG. 4 depicts the effect of bioactive fluid compositions according to the disclosure on endothelial breakdown in vitro (shedding of Syndecan-1) HUVEC compared to standard-of-care crystalloid fluid (NS), demonstrating that the bioactive fluid compositions and media preserved HUVEC integrity compared to NS which significantly increased Syndecan-1 shedding.

Results. As shown in FIG. 4, culture with composition C-1A lead to glycocalyx breakdown indicated by a significant increase in shed Syndecan-1 (p=0.02). In contrast, the concentration of shed Syndecan-1 detected in cultures of HUVECs and composition 1A was similar to culture medium (media after 4-hours co-culture with HUVEC). These data show that the bioactive fluid composition according to the disclosure protected vascular endothelial cells from injury, whereas NS induced vascular endothelial cell breakdown.

Example 4: Effect on Endothelial Cell Metabolism

Method. HUVECs were prepared as described above. After conclusion of the 12-hour incubation in composition C-1A, composition C-2A, or composition 1A, HUVEC metabolism was determined using the CyQuant XTT assay (a tetrazolium-based compound that is converted to an orange-colored formazan product by actively respiring cells).

Figure 5:
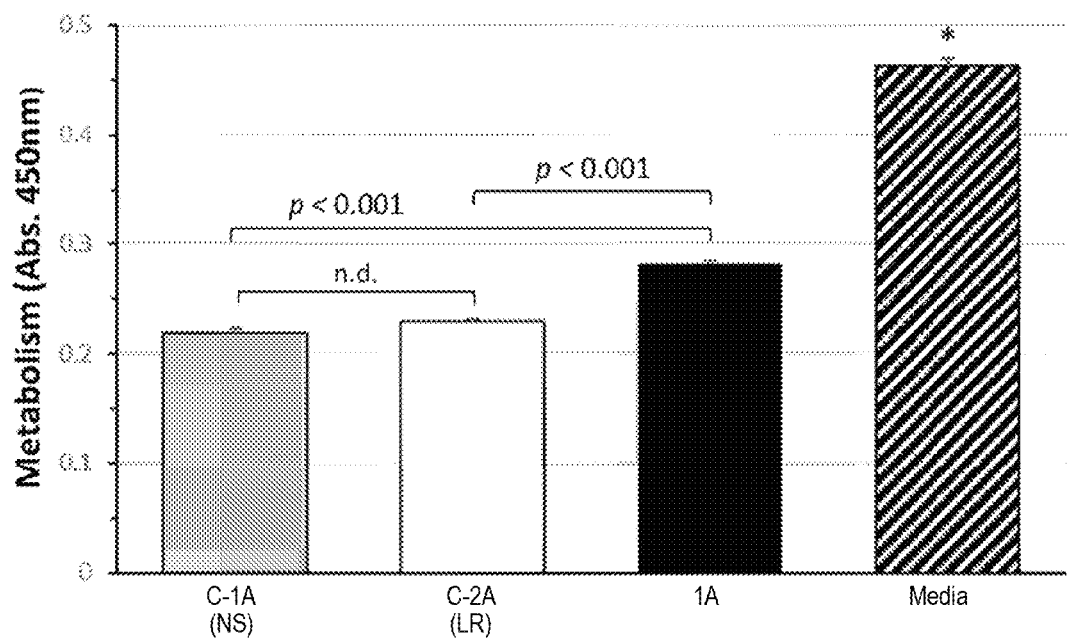
FIG. 5 depicts the effect of bioactive fluid compositions according to the disclosure on HUVEC metabolism in vitro, demonstrating that the bioactive fluid compositions significantly increased HUVEC metabolism versus standard-of-care crystalloid IV fluids (NS and LR).

Results. The data in FIG. 5 show that incubation of HUVECs in composition 1A resulted in significantly increased cell metabolism compared to NS or LR treated cells (p=0.001). These data show that the bioactive fluid composition according to the disclosure is able to support HUVEC metabolism in-vitro, whereas the standard-of-care NS or LR display metabolism consistent with senescent cells. When combined with the cell viability and growth data of Examples 1 and 2, these studies show that bioactive fluid compositions according to the disclosure prevent vascular cell stress and supports growth and, potentially, support the repair or restore the function of damaged blood vessels.

Example 5: Effect on Microvascular Networks

Method. A rodent exchange transfusion model was used to simulate the effect of the hemorrhage and resuscitation with bioactive fluid compositions according to the disclosure on the architecture and function of microvascular networks. Animals were anesthetized and cannulated to allow for the withdrawal of blood and/or infusion of IV fluids. The spinotrapezius muscle was then isolated and externalized onto a heated microscope stage.

Next, animals received a 50% v/v exchange transfusion of either composition C-2A or composition 1A. Microvascular networks were observed using intra-vital microscopy and digital images were captured in real time using a color CMOS camera (Axiocam 305 color, Zeiss, Germany).

Figure 6:
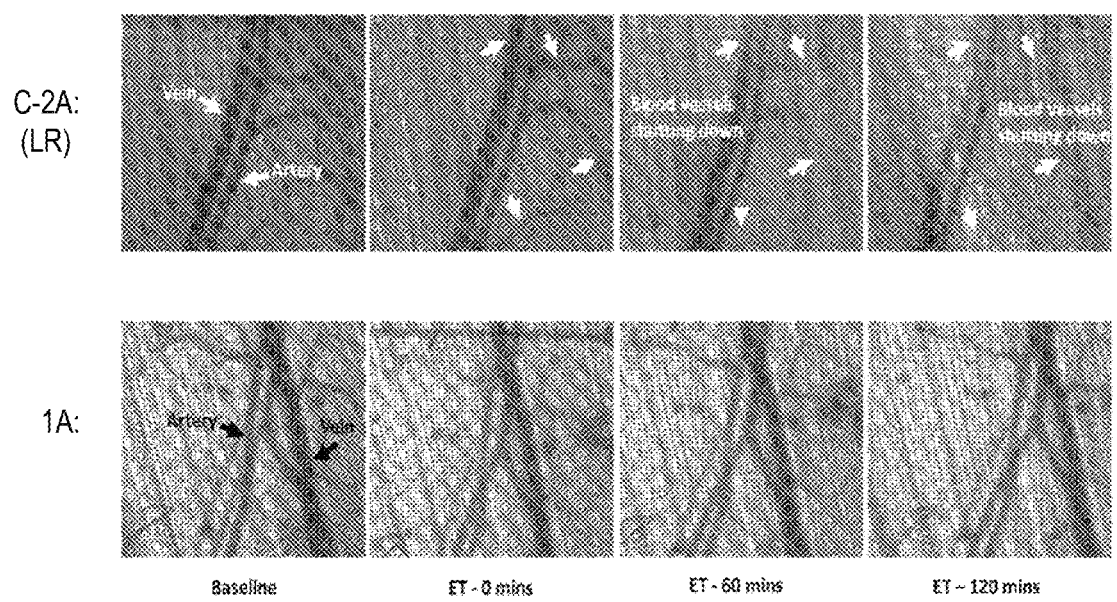
FIG. 6 depicts the effect of bioactive fluid compositions according to the disclosure on vascular patency in vivo compared to standard-of-care crystalloid fluid (LR), demonstrating that the bioactive fluid compositions preserved openness of functional blood vessels whereas LR caused vascular collapse.

Results. The data in FIG. 6 show that composition 1A preserved the architecture and "openness" (patency) of blood vessels following exchange transfusion. Animals transfused with composition C-2A showed a narrowing and eventual collapse of peripheral tissue blood vessels (white arrow heads). These data demonstrate that transfusion with bioactive fluid compositions according to the disclosure preserves microvascular networks, whereas LR transfusion is associated with vascular "shutdown" (i.e., vascular shock).

Example 6: Effect on Fluid Extravasation Compared to LR

Method: Animals were prepared as described above. A small fluorescent protein (rhodamine labeled albumin) was injected intravenously to enable visualization of leakage from the blood vessels using fluorescent microscopy and animals were allowed to acclimate for 15 minutes. To simulate the effect of intravenous fluid therapy, rats were then infused with the equivalent of 15% of their blood volume of either composition C-2A or composition 1A over 12 minutes. This procedure was performed as a "top-load" (i.e., no blood was withdrawn). Vascular leakage measured by capturing and quantitating fluorescence of the labelled protein at 568 nM with a Zeiss Axiovert fluorescence microscope.

Figure 7:
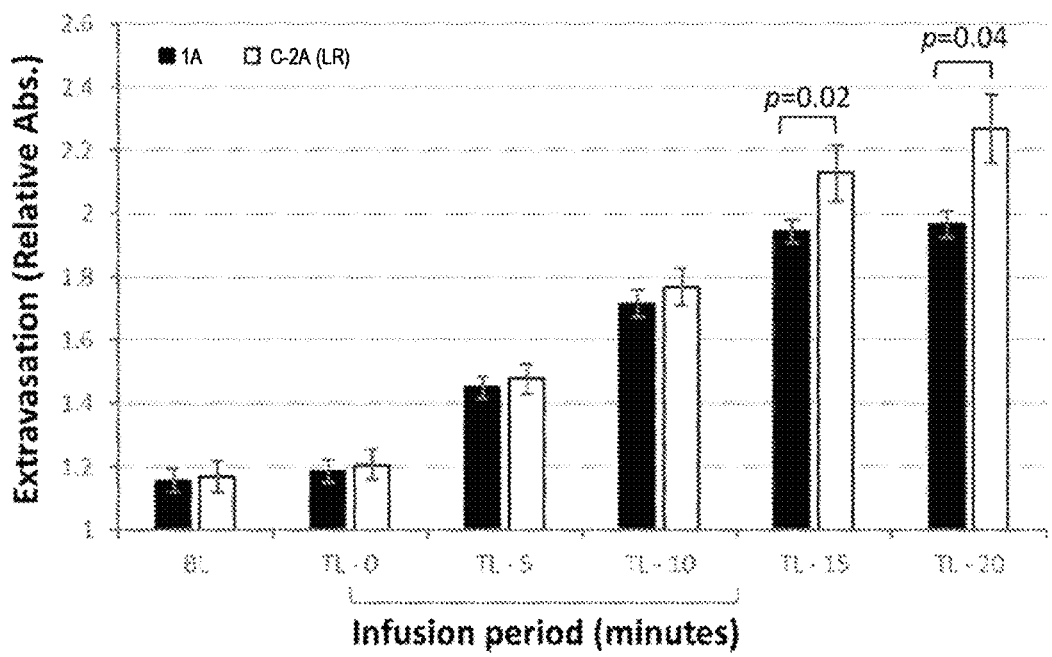
FIG. 7 depicts the effect of bioactive fluid compositions according to the disclosure on extravasation in vivo, demonstrating that the bioactive fluid compositions arrested extravasation compared to the standard-of-care crystalloid fluid (LR) which resulted in significant continuing extravasation.

Results. The data in FIG. 7 show that during the infusion period, leakage of fluorescent albumin was approximately equivalent in both the composition C-2A and composition 1A treatment groups. All intravenous fluids leak during infusion, presumably due to increased vascular pressure from the infusion procedure and the additional fluid volume (i.e., 15% of the estimated blood volume). After infusion was completed, however, composition 1A immediately arrested the leakage of albumin, whereas treatment with composition C-2A was associated with significant continuing leakage (p<0.05). These data show that bioactive fluid compositions according to the disclosure protect vascular integrity and reduce fluid leakage from blood vessels.

Example 7: Effect on Peripheral Tissue Oxygen Perfusion

Method. Animals were prepared as described in Example 5 and underwent 50% v/v exchange transfusion. A porphyrin dye was painted on the spinotrapezius muscle and excited using a 488 nm light source. Tissue oxygen perfusion was measured by capturing and quantitating fluorescence at 518 nm with a Zeiss Axiovert fluorescence microscope.

Figure 8:
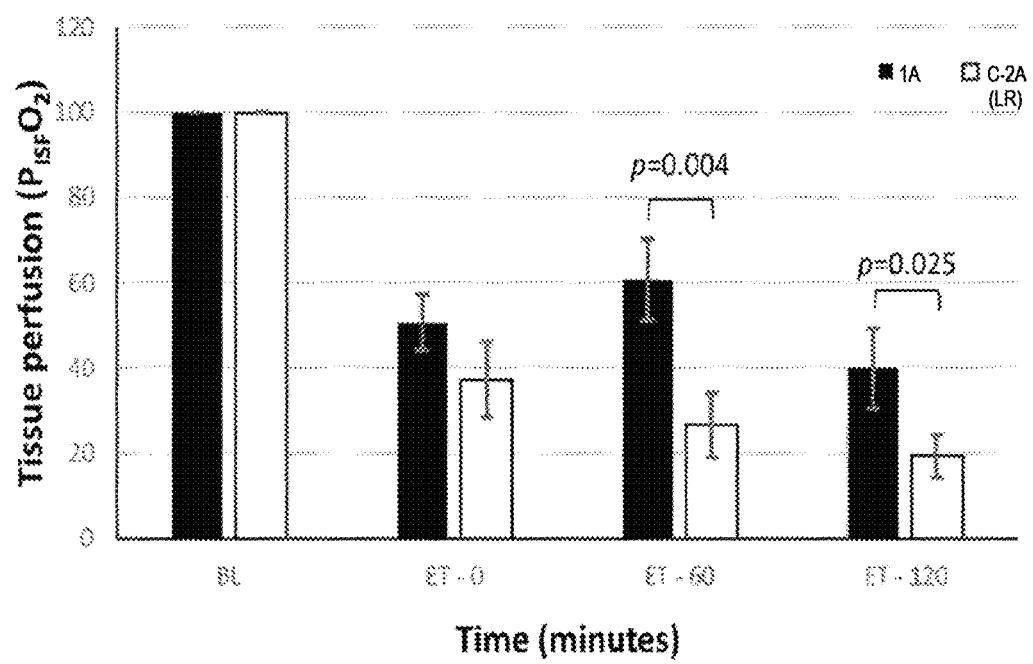
FIG. 8 depicts the effect of bioactive fluid compositions according to the disclosure on tissue oxygen perfusion in vivo, demonstrating that the bioactive fluid compositions preserved tissue oxygen perfusion compared to the standard-of-care crystalloid fluid (LR) which led to a significant reduction in oxygen perfusion.

Results. The data in FIG. 8 show that exchange transfusion immediately reduced tissue oxygen perfusion by 50% in animals that received either composition C-2A or composition 1A (ET-0), consistent with the withdrawal of 50% of the oxygen-carrying blood. Over the next two hours, animals transfused with composition 1A were able to maintain tissue oxygen perfusion in the range of 40-60% of baseline. In contrast, animals treated with composition C-2A showed a significant, continuing decline in tissue oxygen perfusion to a nadir of approximately 20%. These data show that transfusion with bioactive fluid compositions according to the disclosure is able to keep the remaining blood (50%) circulating to peripheral tissues, whereas the standard-of-care fluid leads to impaired tissue oxygen perfusion.

Example 8: Effect Following Hemorrhage and Shock

Method. A well-defined, pressure-controlled model of severe (Grade 3) hemorrhagic shock in Sprague Dawley rats was used to confirm the effect of bioactive fluid compositions according to the disclosure on clinical measures of outcome and survival, as predicted by the earlier in vitro and in vivo studies. Animals were anesthetized and blood was withdrawn to reach a mean arterial pressure of 40 mmHg, and maintained at that pressure for the next 60 minutes by withdrawal and/or reinfusion of blood (i.e., a 60-minute shock period). Animals were resuscitated using fluid volumes based on the DoD's Tactical Combat Casualty Care Guidelines and received 1.5× their blood loss volume of composition C-1A or composition 1A by intravenous bolus over 10 minutes. To test the effect of fluid volume, in some animals the IV fluid bolus was delivered as either a) single bolus or b) two equal boluses separated by a 5-minute interval (0.75× the blood loss volume per bolus). After infusion of IV fluid was completed, animals were monitored for 2 hours post-resuscitation under anesthesia and then disconnected from the monitor and observed for an additional 4 hours (total of 6 hours post-resuscitation).

Clinical parameters, including MAP and heart rate (HR) were monitored for the first two hours following hemorrhage and resuscitation using a Biopac MP160 system. Serum chemistry and arterial blood gas (ABG) data were measured using an ABL90 Flex (Radiometer) at fixed time points: pre-hemorrhage (baseline), post-hemorrhage (end-of-shock), end-of-resuscitation, two hours post-resuscitation (T=200 mins) and at the study end (T=440 mins).

Results: Heart rate (HR). All animals had similar HRs in the hemorrhage/shock phase and during resuscitation. The group treated with composition C-1A became tachycardic in the post-resuscitation phase, whereas the HR for the animals treated with composition 1A returned to normal. These data show that animals treated with composition 1A did not need to compensate through tachycardia to offset the physiological effects of hemorrhage and shock.

Results: Mean arterial pressure (MAP). All animals had a similar MAP in the hemorrhage/shock phase. Both groups of animals had increases in MAP immediately following resuscitation, however, this was significantly greater (by 20 mmHg) in the animals treated with composition 1A. These data show that infusion of bioactive fluid compositions according to the disclosure can increase blood pressure more effectively than the standard-of-care, NS.

Results: Infusion volume. Additional studies testing the effect of fluid volume on MAP (i.e., 0.75× versus 1.5× the estimated blood loss volume) show that resuscitation with composition 1A was able to produce the same MAP as NS, but with 50% of the volume. These data show that a smaller volume of bioactive fluid compositions according to the disclosure may be used for resuscitation which, in turn, will reduce the potential for dilutional and other adverse side-effects of crystalloid resuscitation.

Results: Arterial Blood Chemistry. Statistically significant deficits were observed in critical metabolic markers of hemorrhagic shock (pH, base deficit, glucose, and lactate) at end-of-shock relative to baseline. These findings confirmed the induction of shock in all animals. Two hours after resuscitation, animals with composition 1A showed significant improvement in pH, base deficit, lactate and glucose, whereas these markers remained at detrimental levels in animals treated with composition C-1A. Improvement and/or normalization of these metabolite levels is associated with improved outcomes. Additionally, chloride levels remained within the normal range in animals treated with composition 1A in contrast to animals treated with composition C-1A, which developed significant hyperchloremia by 2-hours post-resuscitation. This data shows that bioactive fluid compositions according to the disclosure effectively prevent the induction of hyperchloremia and improves metabolic markers of shock, which is expected to lead to improved clinical outcomes compared to subjects receiving NS.

Results: Survival. The data in FIG. 9 show that animals treated with composition 1A had a significantly increased survival rate (approximately 50%) at the end of the experiment, compared to animals treated with composition C-1A (approximately 20% survival rate). Overall, 60% of the animals treated with composition 1A awoke and recovered their "righting" reflex and 20% were mobile. None of the animals treated with composition C-1A recovered their "righting" reflex, and one animal treated with composition C-1A developed hematuria. These data show that bioactive fluid compositions according to the disclosure can improve survival compared to NS, and are extremely promising given that survival was a secondary end-point due to the severity of this rat hemorrhage model and that animals were resuscitated with a single bolus of IV fluid and no other treatment over the 6-hour study period. In addition, the data also show that resuscitation with composition 1A results in a significant 3-fold increase in the minimum survival time compared with NS ($p<0.001$). These data show that resuscitation with bioactive fluid compositions according to the disclosure can extend the time for patients to be evacuated to a medical treatment facility and receive definitive care, thereby increasing their chance of survival.

Example 9. Effect on Fluid Extravasation Compared to NS

Method. The same method as described in Example 6 above was used to study how bioactive fluid compositions according to the disclosure would impact extravasation as compared to NS.

Figure 10:
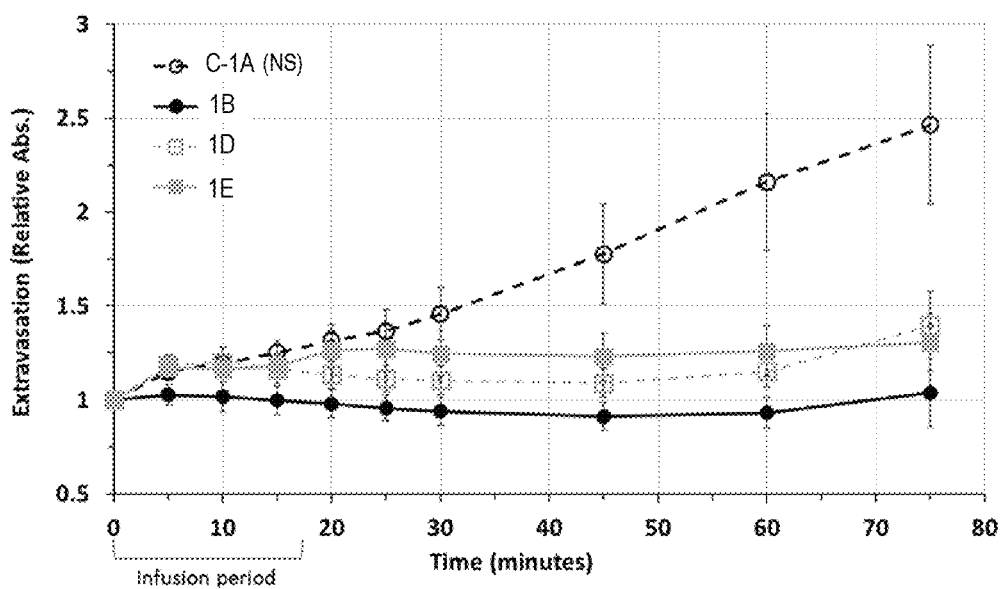
FIG. 10 depicts the effect of bioactive fluid compositions according to the disclosure on extravasation in vivo, demonstrating that the bioactive fluid compositions arrested extravasation compared to the standard-of-care crystalloid fluid (NS) which resulted in significant continuing extravasation.
Figure 11:
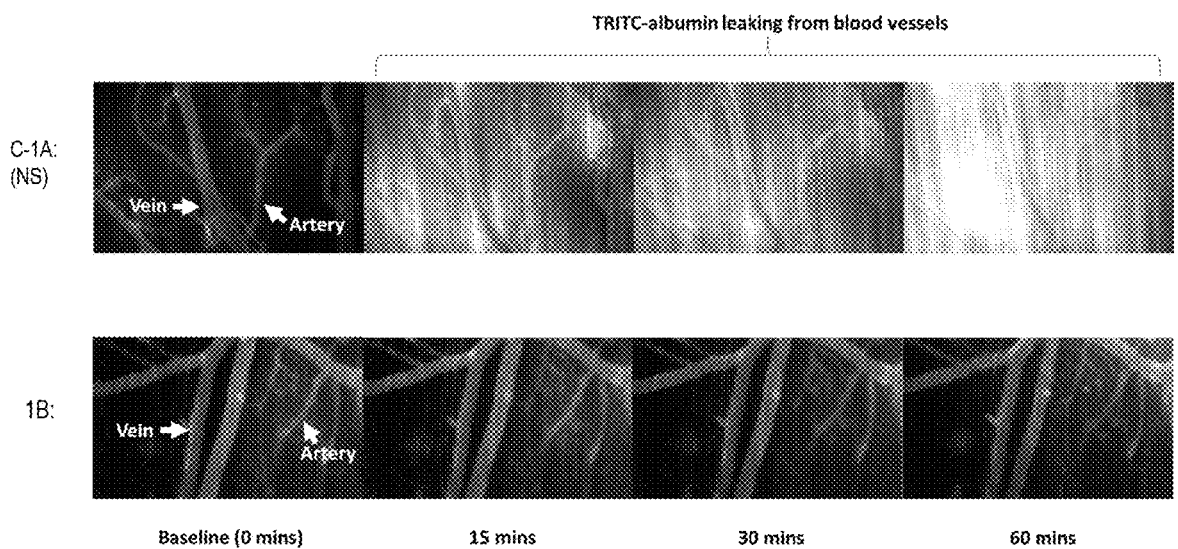
FIG. 11 shows images of extravasation of bioactive fluid compositions according to the disclosure in vivo compared to standard-of-care crystalloid fluid (NS).

Results. The data in FIG. 10 show that composition 1B maintains vascular integrity and prevents the leakage of albumin from blood vessels. There was no significant increase in fluorescent albumin in the interstitial tissues at any time point compared to baseline. In contrast, NS-treatment was associated with significant leakage that commenced within 5 minutes of infusion and persisted for the study duration ($p<0.01$). Leakage in animals treated with composition C-1A was significantly greater at all time points compared with animals that received composition 1B ($p<0.005$). The relative difference in albumin leakage is illustrated in FIG. 11, which shows extreme leakage of fluorescent albumin in rats treated with NS versus baseline fluorescence in animals treated with composition 1B. FIG. 11 confirms that composition 1B leads to significantly less extravasation compared to NS.

Additionally, the effect of compositions 1D and 1E on albumin extravasation is shown in FIG. 10. Infusion of compositions 1D and 1E was associated with transient leakage of albumin within the first 5 minutes of infusion compared to baseline. This leakage arrested within 10 minutes of infusion and no further leakage, as measured by accumulation of fluorescent tracer in the interstitial tissue, was observed for the study duration ($p<0.05$).

Combined, these data show that bioactive compositions according to the disclosure protect vascular integrity and reduce or prevent fluid leakage from blood vessels, further confirming the results of Example 6 that bioactive fluid compositions according to the disclosure provide superior protection compared to known crystalloid fluids.

Example 10. Effect on Extravasation in an LPS-Induced Model of Endotoxemia

Method. Subject animals were injected with 1U/kg of lipopolysaccharide (LPS) intraperitoneally (IP) 18 hours prior to surgery. Rats then underwent surgical exposure of the Spinus trapezius muscle, intravenous fluid infusion, and fluorescence microscopy as described in Example 6 above.

Figure 12:
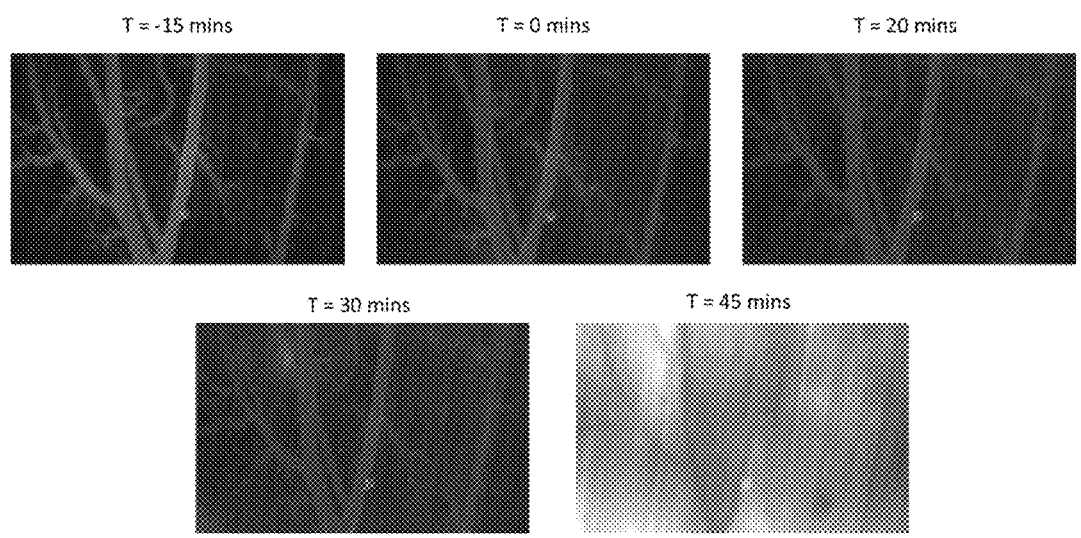
FIG. 12 shows images of leakage in vivo in a control Sprague-Dawley rat with LPS-injection plus surgery and fluorescent tracer, but no intravenous fluid infusion.

Results. The data show that in an LPS-induced sepsis model, animals treated with composition 1A show reduced leakage of fluorescent albumin into interstitial tissues compared to both NS-treated and sham animals. FIGS. 12-16 show representative images of leakage of fluorescent albumin into vascular tissue beds of the exteriorized rat spinotrapezius muscle. Sham animals (LPS-injection plus surgery and fluorescent tracer, but no intravenous fluid infusion) show moderate leakage of the fluorescent tracer and its accumulation in the vascular tissue bed commencing at T=45 mins (FIG. 12). This result provided the 45-minute limit for the study duration due to commencement of vascular leak in the LPS-endotoxemia model that is independent of intravenous fluid infusion (tissue desiccation due to exposure of the exteriorized muscle to environmental air).

Figure 13:
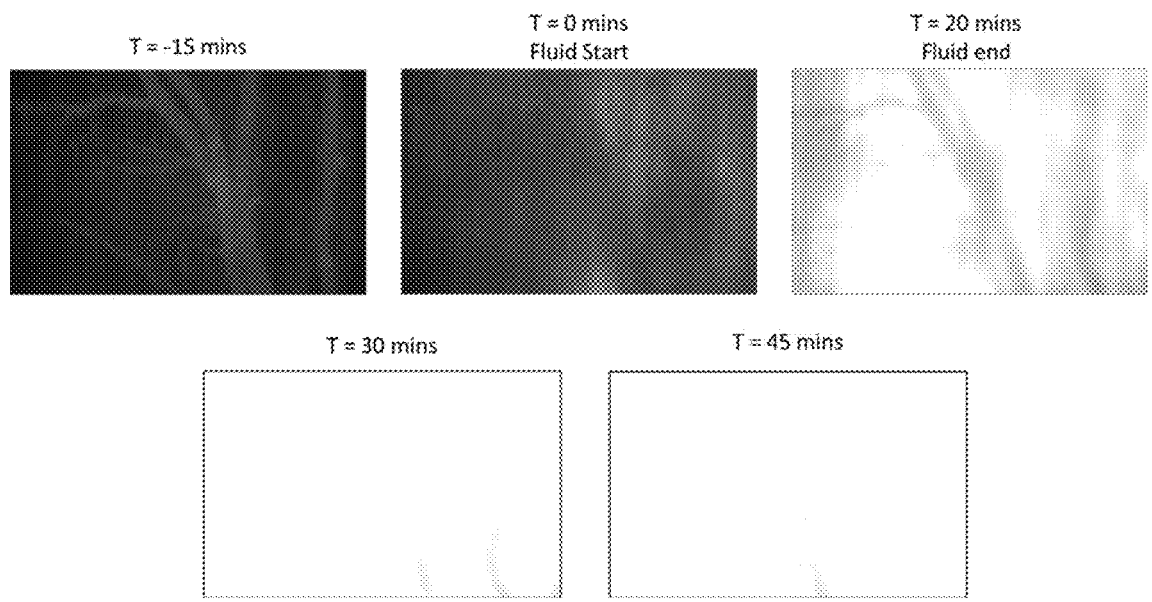
FIG. 13 shows images of leakage in vivo in a Sprague-Dawley rat with LPS-injection plus surgery, fluorescent tracer, and intravenous infusion of NS.
Figure 14:
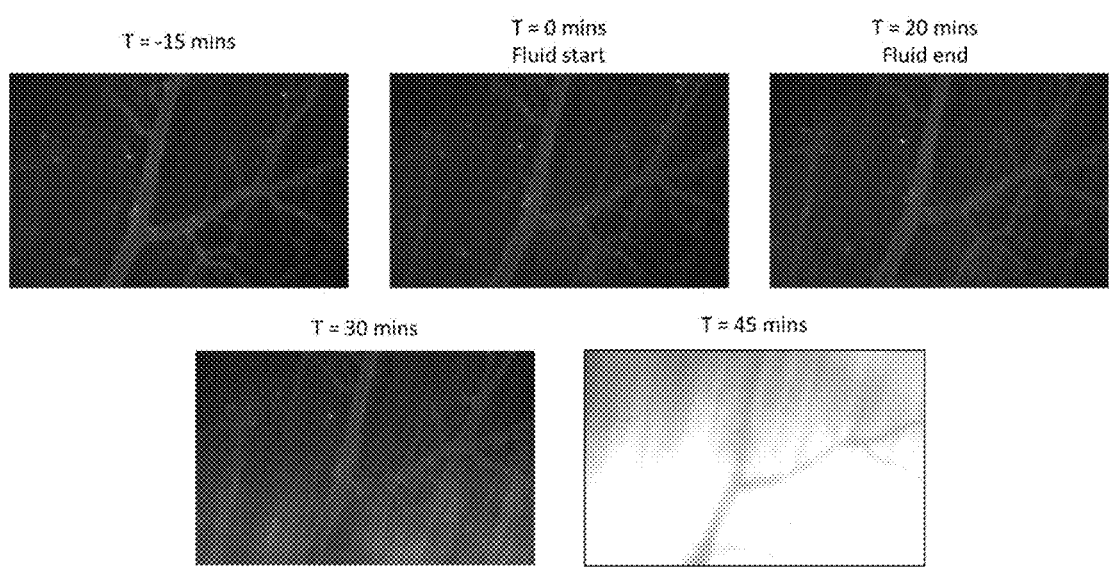
FIG. 14 shows images of leakage in vivo in a Sprague-Dawley rat with LPS-injection plus surgery, fluorescent tracer, and intravenous infusion of a bioactive fluid composition according to the disclosure.
Figure 15:
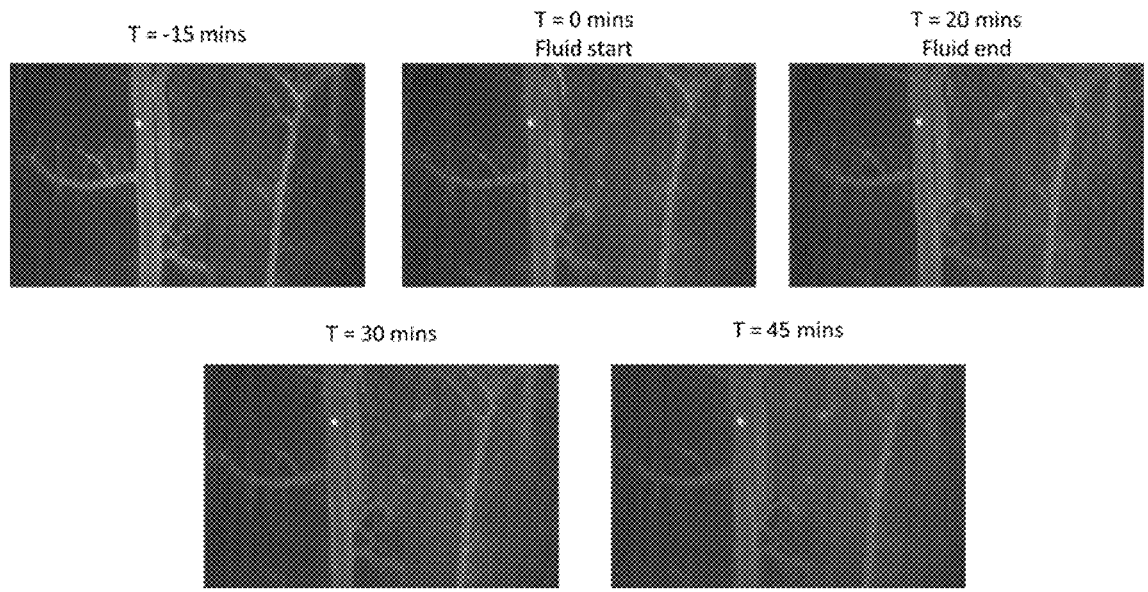
FIG. 15 shows images of leakage in vivo in a Sprague-Dawley rat with LPS-injection plus surgery, fluorescent tracer, and intravenous infusion of a bioactive fluid composition according to the disclosure.

As shown in FIG. 13, intravenous infusion of composition C-1A resulted in immediate leakage and accumulation of fluorescent albumin (T=0 mins), and extreme leakage by T=20 mins that continued until the study end (T=45 mins). In contrast, representative images from two separate studies show that intravenous infusion of composition 1A does not induce vascular leakage. FIGS. 14 and 15 illustrate background levels of fluorescent albumin following infusion of composition 1A that is similar to sham animals. FIG. 14 shows a minor accumulation of fluorescent albumin commencing at T=30 mins that is similar to sham controls. Moderate accumulation of fluorescent albumin is evident in both FIGS. 14 and 15 by T=45 mins, which is consistent with sham animals.

Figure 16:
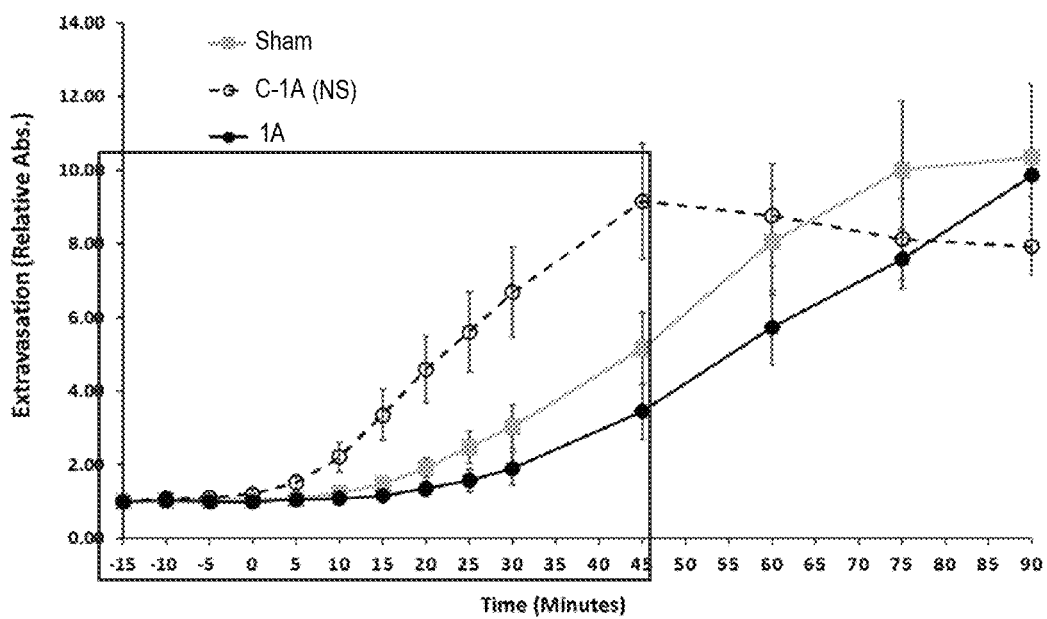
FIG. 16 shows data for interstitial accumulation of fluorescent tracer in the LPS endotoxemia model for control, NS-treated animals, and animals treated with a bioactive fluid composition according to the disclosure.

Quantitative data for interstitial accumulation of fluorescent tracer in the LPS-endotoxemia model are shown in FIG. 16. The NS-treated group show a significant increase in fluorescent albumin accumulation from T=5 mins through T=45 mins compared to baseline ($p<0.001$), and also compared to animals treated with composition 1A ($p<0.05$) and the sham control group ($p<0.05$). Additionally, animals treated with composition 1A had equivalent (or trended towards less) albumin accumulation than the sham control group which suggests that bioactive compositions according to the disclosure may have some restorative effect on vascular integrity and the prevention of fluid leakage compared to sham, as seen in FIG. 16. As described above, the data shown in FIG. 16 after 45 minutes (outside the box) is an artifact of the model and not relevant to comparison of the effect on extravasation.

Example 11. Study of Components in the Bioactive Fluid Compositions

Method. Cell culture studies using HUVECs appear to be predictive of the role of components in protecting endothelial cells and their effectiveness as bioactive components of intravenous fluids using the method of Example 1. Test groups included compositions 1A, IC, 1D, and compositions 2A-2C shown in Table 3 (mean values, ±10%).

TABLE 3

| Component | Amount (mg/L) | | |
|---|---|---|---|
|  | 2A | 2B | 2C |
| Sodium chloride | 5,804.00 | 5,804.00 | 5,804.00 |
| Copper chloride dihydrate | 1.55 | 1.55 | 1.55 |
| Zinc chloride | 3.42 | 3.42 | 3.42 |
| Magnesium chloride hexahydrate | 85.37 | 85.37 | 85.37 |
| Sodium phosphate monobasic monohydrate | 41.40 | 41.40 | 41.40 |
| Sodium phosphate dibasic | 170.30 | 170.30 | 170.30 |
| Potassium chloride | 223.00 | 223.00 | 223.00 |
| Sodium acetate | 2,500.00 | 2,500.00 | 2,500.00 |
| Sodium pyruvate | 110.00 | 110.00 | 110.00 |
| L-Malic acid | 67.10 | 67.10 | 67.10 |
| L-Histidine |  |  | 12.50 |
| L-Isoleucine | 8.00 |  |  |
| L-Leucine | 13.00 |  |  |
| L-Lysine hydrochloride |  |  | 32.50 |
| L-Methionine |  |  | 3.00 |
| L-Phenylalanine |  | 6.00 |  |
| L-Threonine |  |  | 19.00 |
| L-Tryptophan |  | 14.28 |  |
| L-Valine | 23.00 |  |  |
| D-Glucose | 2,000.00 | 2,000.00 | 2,000.00 |
| Water | QS | QS | QS |

Fresh culture medium was used as a positive control for continued cell growth, while NS was used as a negative control (100% cell death).

Figure 17:
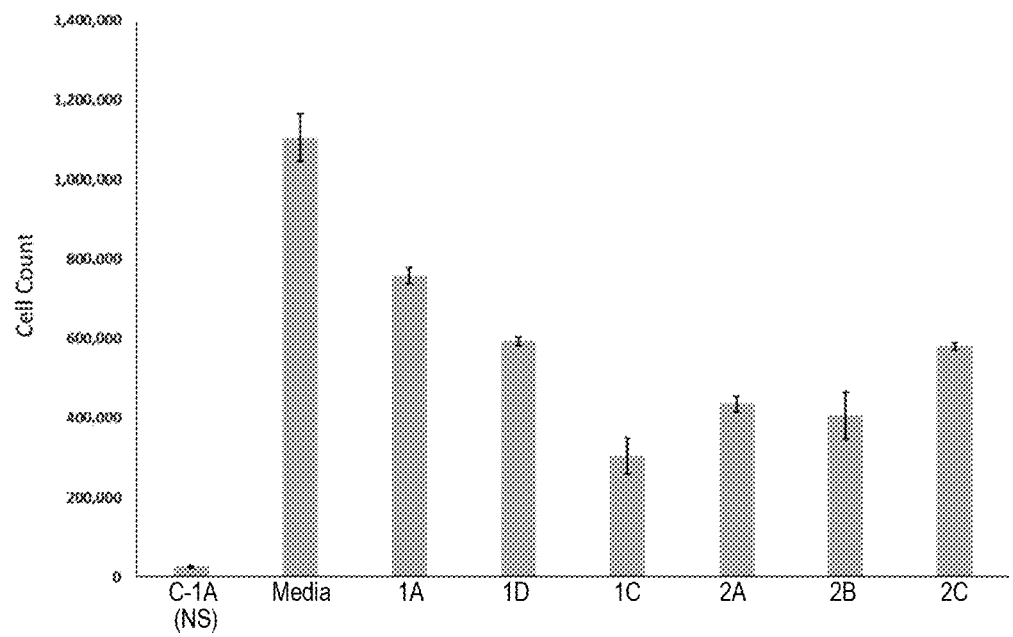
FIG. 17 depicts cell mortality in primary human vascular endothelial cell (HUVEC) cultures following exposure to standard-of-care IV fluid (NS), and bioactive fluid compositions according to the disclosure.

Results. As seen in FIG. 17, composition 1D retained 78% of the activity of composition 1A to support the viability of HUVECs. Retaining only the hydrophobic amino acids (composition 2A) reduced HUVEC viability to 57% compared to composition 1A, and the aromatic amino acids (composition 2B) were similar with 53% HUVEC compared to composition 1A. The polar amino acid mix (composition 2C) retained 70% of the activity of composition 1A and was similar to composition 1D. While all bioactive fluid compositions according to the disclosure significantly outperformed NS, these data show the relative effect of various components in supporting the survival and viability of vascular endothelial cells.

Example 12. Study of Components in the Bioactive Fluid Compositions

Method. Using the method described in Example 1, the role of serine and threonine together in supporting survival of HUVECs was evaluated with bioactive fluid compositions 1A, 1C, and 1D, as well as 3A shown in Table 4A, and compositions C-1A and C-2A, as well as C-3A and C-4A shown in Table 4B (mean values, ±10%).

TABLE 4A

| Component | Amount (mg/L) | | |
|---|---|---|---|
| | 3A | 3B | 3C |
| Sodium chloride | 5,804.00 | 5,804.00 | 5,804.00 |
| Copper chloride dihydrate | 1.55 | 1.55 | 1.55 |
| Zinc chloride | 3.42 | 3.42 | 3.42 |
| Magnesium chloride hexahydrate | 85.37 | 85.37 | 85.37 |
| Sodium phosphate monobasic monohydrate | 41.40 | 41.40 | 41.40 |
| Sodium phosphate dibasic | 170.30 | 170.30 | 170.30 |
| Potassium chloride | 223.00 | 223.00 | 223.00 |
| Sodium acetate | 2,500.00 | 2,500.00 | 2,500.00 |
| Sodium pyruvate | 110.00 | 110.00 | 110.00 |
| L-Malic acid | 67.10 | 67.10 | 67.10 |
| L-Serine | 10.00 | 10.00 | |
| L-Threonine | 19.00 | | 19.00 |
| D-Glucose | 2,000.00 | 2,000.00 | 2,000.00 |
| Water | QS | QS | QS |

TABLE 4B

NS AND LR WITH ADDITIONAL COMPONENTS

| Component | Amount (mg/L) | | | |
|---|---|---|---|---|
| | C-3A | C-4A | C-4B | C-4C |
| Sodium chloride | 9,000 | 6,000 | 6,000 | 6,000 |
| Sodium lactate | | 3,100 | 3,100 | 3,100 |
| Potassium chloride | | 300 | 300 | 300 |
| Calcium chloride | | 200 | 200 | 200 |
| L-Serine | 10.00 | 10.00 | 10.00 | |
| L-Threonine | 19.00 | 19.00 | | 19.00 |
| Water | QS | QS | QS | QS |

Composition C-3A is NS with added serine and threonine, and compositions C-4A to C-4C are LR with added serine and/or threonine.

Figure 18:
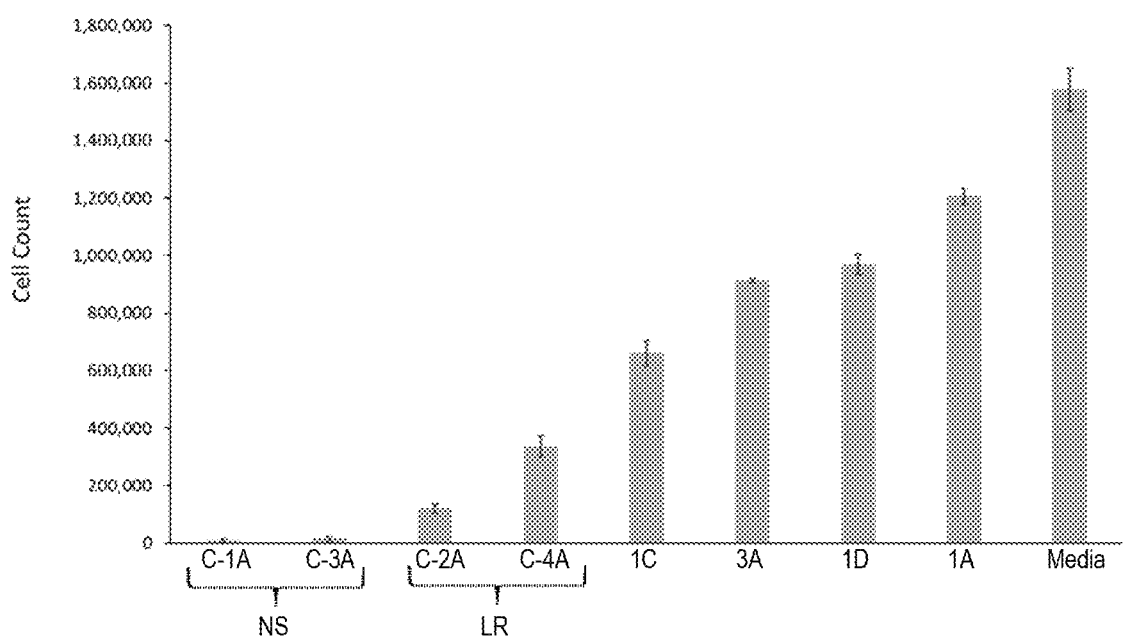
FIG. 18 depicts cell mortality in primary human vascular endothelial cell (HUVEC) cultures following exposure to standard-of-care IV fluids (NS or LR) and bioactive fluid compositions according to the disclosure, with serine and threonine.

Results. As shown in FIG. 18, composition 3A, which includes the components of composition 1C with added serine and threonine, performed better than composition 1C and retained 76% of the activity of composition 1A in supporting viability of HUVECs. Composition 3A demonstrated similar activity to that achieved with composition 1D. Addition of serine and threonine to standard-of-care intravenous fluids such as NS (composition C-3A) and LR (composition C-4A) resulted in increased viability of HUVECs compared to crystalloid fluid alone. While all bioactive fluid compositions according to the disclosure significantly outperformed NS and LR even with the addition of serine and threonine, these data demonstrate the role of the serine and threonine, both polar amino acids, in supporting the survival and viability of vascular endothelial cells.

Example 13. Study of Components in the Bioactive Fluid Compositions

Method. Using the method described in Example 1, the effect of adding serine, threonine, and serine plus threonine to LR on HUVEC survival as compared to bioactive fluid compositions according to the disclosure was evaluated. Test groups included bioactive fluid compositions 1A, 1C, and 1D, as well as 3A-3C shown in Table 4A, and compositions C-2A, as well as C-4A, C-4B, and C-4C shown in Table 4B.

Figure 19:
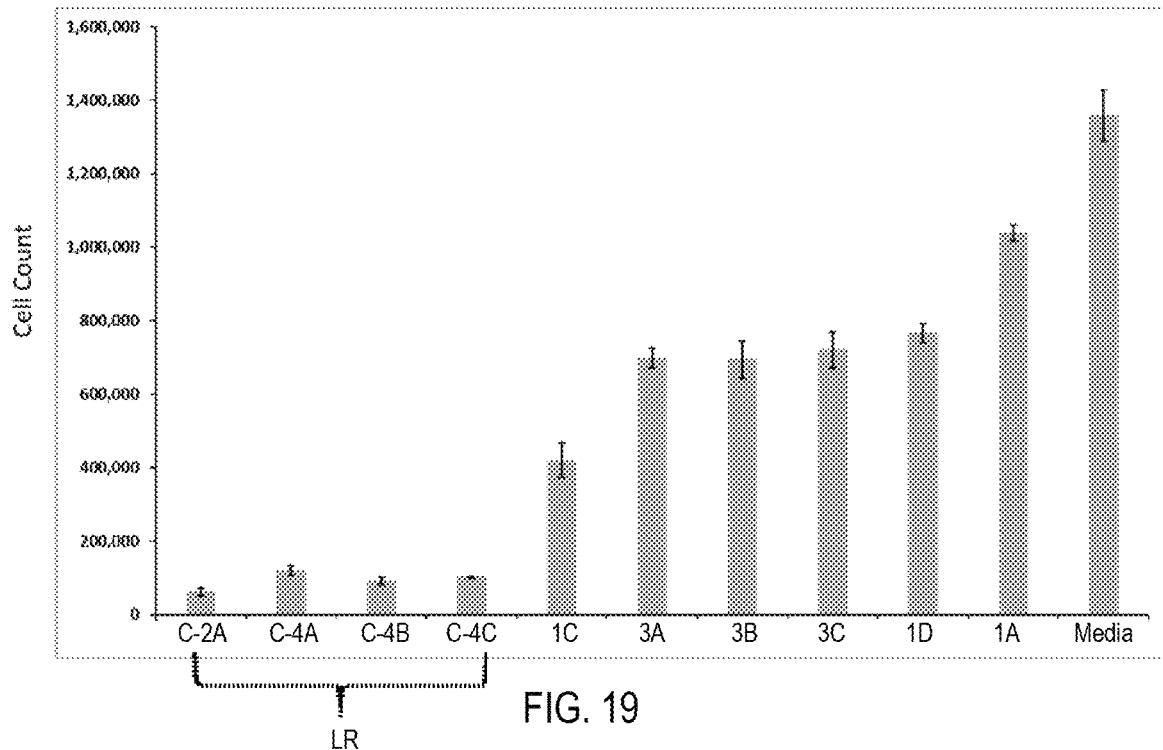
FIG. 19 depicts cell mortality in primary human vascular endothelial cell (HUVEC) cultures following exposure to standard-of-care IV fluid (LR) and bioactive fluid compositions according to the disclosure, with serine and/or threonine.

Results. As seen in FIG. 19, serine or threonine are equally effective in increasing the survival of endothelial cells. Compositions 3A-3C, which include the components of composition 1C with added serine and/or threonine, resulted in preservation of HUVEC viability that was similar to that of composition 1D, and approximately 65-70% of activity of composition 1A. Addition of serine and/or threonine to LR (compositions C-4A, C-4B, and C-4C) also increases the viability of HUVEC compared with LR alone (composition C-2A). While all bioactive fluid compositions according to the disclosure significantly outperformed LR, even with the addition of serine, threonine, or serine and threonine, these data confirm the role of serine and threonine independently in supporting the survival and viability of vascular endothelial cells.

Example 14. Study of Components in the Bioactive Fluid Compositions

Method. Using the method described in Example 1, the effect of various components to promote the survival of endothelial cells in vitro was evaluated. The effect of removing cysteine, or cysteine, pyridoxine, and folic acid on HUVEC survival was studied. The formulations tested were compositions 1A, 1D, and 1E, as well as compositions 4A-4B shown in Table 5 (mean values, ±10%).

TABLE 5

| Component | Amount (mg/L) | |
|---|---|---|
| | 4A | 4B |
| Sodium chloride | 5,804.00 | 5,804.00 |
| Copper chloride dihydrate | 1.55 | 1.55 |
| Zinc chloride | 3.42 | 3.42 |
| Magnesium chloride | 40.00 | 40.00 |
| Sodium phosphate monobasic monohydrate | 41.40 | 41.40 |
| Sodium phosphate dibasic | 170.30 | 170.30 |
| Potassium chloride | 223.00 | 223.00 |
| Sodium acetate | 2,500.00 | 2,500.00 |
| Sodium pyruvate | 110.00 | 110.00 |
| L-Malic acid | 67.10 | 67.10 |
| L-Alanyl-L-Glutamine | 109.40 | 109.40 |
| L-Arginine | 8.00 | 8.00 |
| L-Asparagine monohydrate | 14.60 | 14.60 |
| L-Aspartic acid | 0.40 | 0.40 |
| L-Citrulline | 7.00 | 7.00 |
| L-Glutamic acid | 9.00 | 9.00 |
| Glycine | 19.00 | 19.00 |
| L-Histidine | 12.50 | 12.50 |
| L-Isoleucine | 8.00 | 8.00 |
| L-Leucine | 13.00 | 13.00 |
| L-Lysine hydrochloride | 32.50 | 32.50 |
| L-Methionine | 3.00 | 3.00 |
| L-Ornithine monohydrochloride | 10.20 | 10.20 |
| L-Phenylalanine | 6.00 | 6.00 |
| L-Proline | 23.00 | 23.00 |
| L-Serine | 10.00 | 10.00 |
| Taurine | 44.00 | 44.00 |
| L-Threonine | 19.00 | 19.00 |
| L-Tyrosine | 9.00 | 9.00 |
| L-Tryptophan | 14.30 | 14.30 |
| L-Valine | 23.00 | 23.00 |
| Vitamin B6 (Pyridoxine hydrochloride) | 0.017 | |
| Folic Acid | 0.099 | |
| L-Ascorbic acid | 15.00 | 15.00 |
| D-Glucose | 2,000.00 | 2,000.00 |
| Water | QS | QS |

Figure 20:
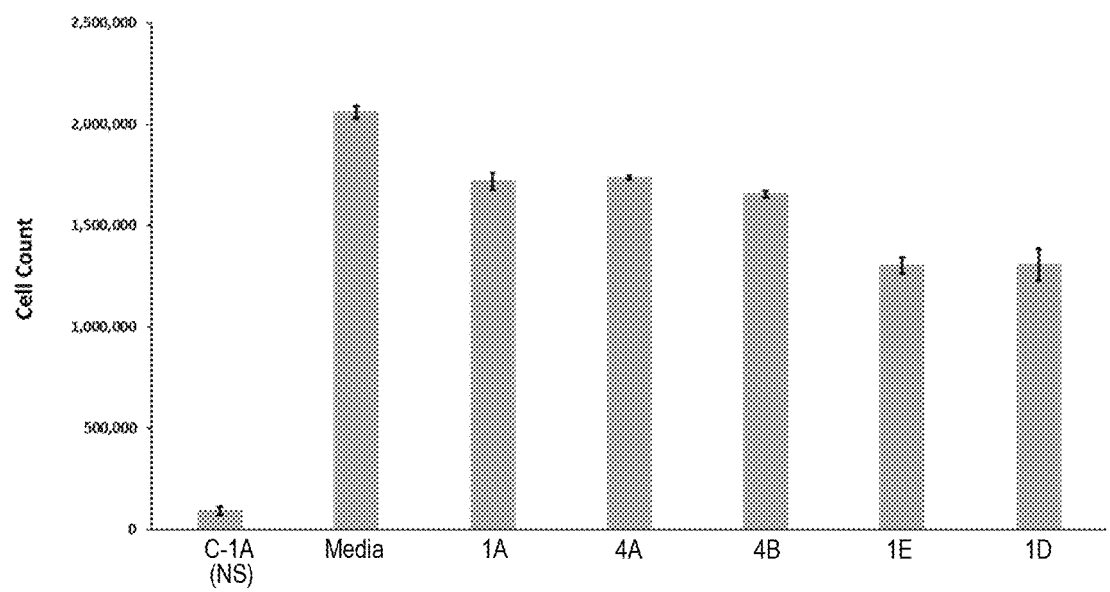
FIG. 20 depicts cell mortality in primary human vascular endothelial cell (HUVEC) cultures following exposure to standard-of-care IV fluid (NS), and bioactive fluid compositions according to the disclosure without cysteine, pyridoxine, and folic acid.

Results. As seen in FIG. 20, compositions 4A and 4B resulted in preservation of HUVEC viability that was similar to that of composition 1A.

Example 15. Study of Components in the Bioactive Fluid Compositions

Method. Using the method described in Example 6 above, the effect of the polar amino acids serine or threonine on fluid extravasation was evaluated.

Figure 21:
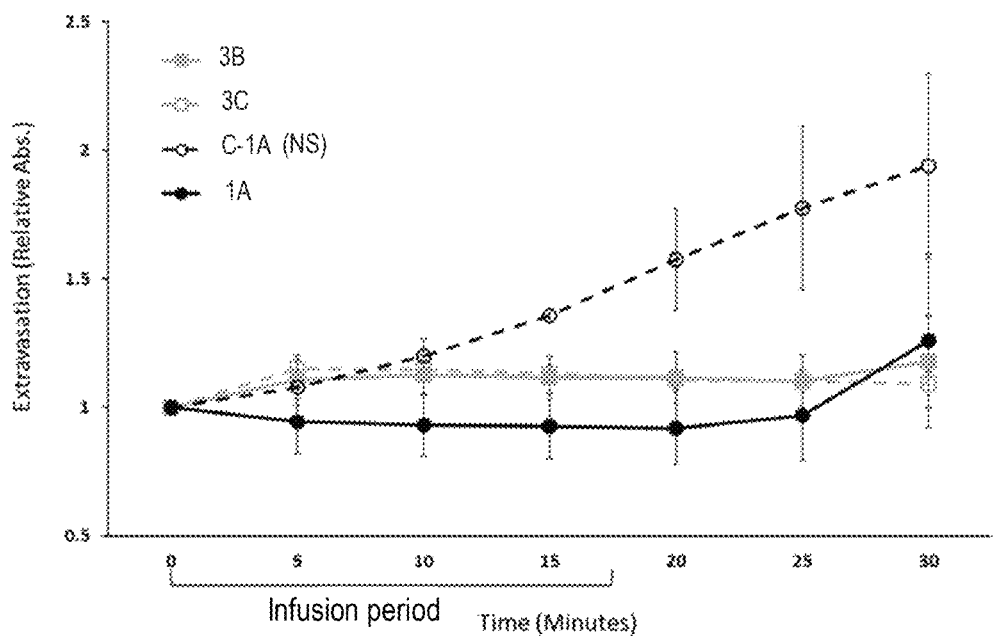
FIG. 21 depicts the effect of NS and bioactive fluid compositions according to the disclosure, with serine or threonine on extravasation in vivo.

Results. As shown in FIG. 21, compositions 3B and 3C demonstrated less fluid extravasation overall compared to composition C-1A. These results are similar to those in Example 9. These data show that infusion of compositions 3B and 3C was associated with transient leakage of albumin immediately following commencement of fluid infusion compared to baseline. This minor leakage arrests within 5 minutes and no further leakage, as measured by accumulation of fluorescent tracer in the interstitial tissue, was observed for the study duration.

Example 16. Study of Components in the Bioactive Fluid Compositions

Method. Using the method described in Example 6 above, the effect of removing the cysteine, pyridoxine, and folic acid from bioactive fluid compositions on fluid extravasation was evaluated.

Figure 22:
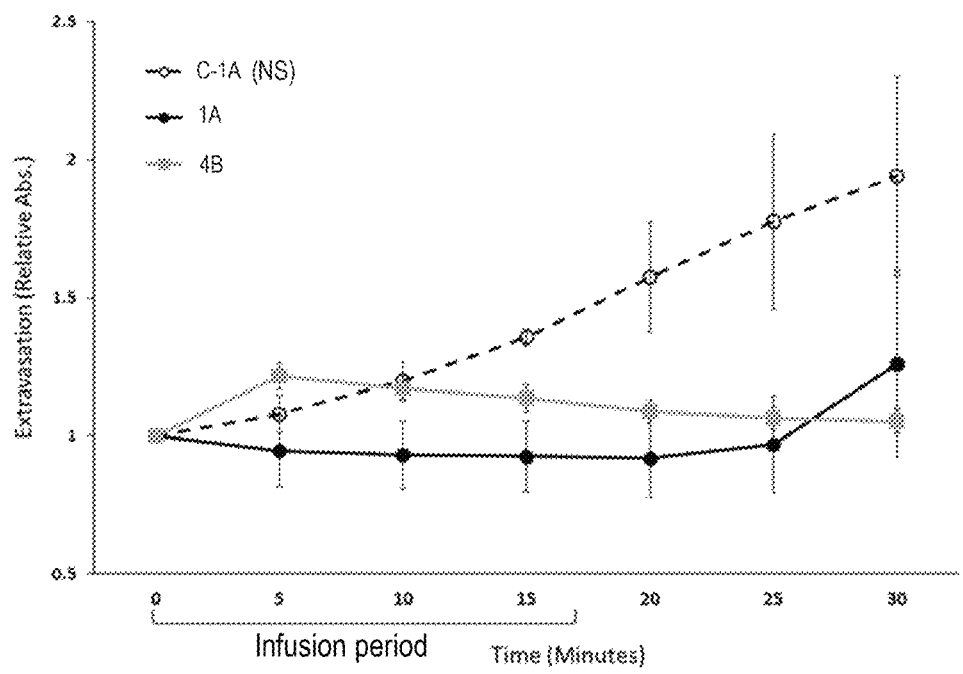
FIG. 22 depicts the effect of NS and bioactive fluid compositions according to the disclosure without cysteine, pyridoxine, and folic acid on extravasation in vivo.

Results. As shown in FIG. 22, composition 4B resulted in extravasation and accumulation of fluorescent tracer similar to that of composition 1A.

Example 17. Additional Bioactive Fluid Compositions

The additional bioactive fluid compositions shown in Table 6 (mean values, ±10%) were also prepared.

TABLE 6

| Component | Amount (mg/L) | | | |
|---|---|---|---|---|
| | 5A | 5B | 5C | 5D |
| Sodium chloride | 5,804.00 | 5,415.00 | 5,423.00 | 5.423 |
| Copper chloride dihydrate | 1.55 | 1.55 | 1.55 | 1.55 |
| Zinc acetate dihydrate | | | 14.7 | 14.7 |
| Zinc chloride | 3.42 | 9.17 | | |
| Magnesium chloride | | 40.00 | 20.00 | 20.00 |
| Magnesium chloride hexahydrate | 85.37 | | | |
| Sodium phosphate monobasic monohydrate | 41.40 | 71.00 | 71.00 | |
| Sodium phosphate dibasic | 170.30 | 71.00 | 71.00 | 142.00 |
| Sodium bicarbonate | | | 2,100.00 | 1,000.00 |
| Potassium chloride | 223.00 | 223.00 | 223.00 | 223.00 |
| Sodium acetate | 2,500.00 | 2,052.00 | 410.15 | 350.69 |
| Sodium pyruvate | 110.00 | 551.00 | 6.00 | 6.00 |
| L-Malic acid | 67.10 | | | |
| β-Alanine | | 35.00 | 35.00 | 35.00 |
| L-Alanyl-L-Glutamine | 109.40 | | | |
| L-Arginine | 8.00 | 8.00 | 8.00 | 8.00 |
| L-Asparagine | | 13.00 | 13.00 | 13.00 |
| L-Asparagine monohydrate | 14.60 | | | |
| L-Aspartic acid | 0.40 | 0.40 | 0.40 | 0.40 |
| L-Citrulline | 7.00 | 7.00 | 7.00 | 7.00 |
| L-Cysteine | | 6.00 | 6.00 | 6.00 |
| L-Glutamic acid | 9.00 | 9.00 | 9.00 | 9.00 |
| L-Glutamine | | 73.00 | 73.00 | 73.00 |
| Glycine | 19.00 | 19.00 | 19.00 | 19.00 |
| L-Histidine | 12.50 | 12.50 | 12.50 | 12.50 |
| L-Isoleucine | 8.00 | 8.00 | 8.00 | 8.00 |
| L-Leucine | 13.00 | 13.00 | 13.00 | 13.00 |
| L-Lysine | | 26.00 | 26.00 | 26.00 |
| L-Lysine hydrochloride | 32.48 | | | |
| L-Methionine | 3.00 | 3.00 | 3.00 | 3.00 |
| L-Ornithine monohydrochloride | 10.21 | 10.21 | 8.00 | 8.00 |

TABLE 6-continued

| Component | Amount (mg/L) | | | |
|---|---|---|---|---|
| | 5A | 5B | 5C | 5D |
| L-Phenylalanine | 6.00 | 6.00 | 6.00 | 6.00 |
| L-Proline | 23.00 | 23.00 | 23.00 | 23.00 |
| L-Serine | 10.00 | 10.00 | 10.00 | 10.00 |
| Taurine | 44.00 | 44.00 | 110.00 | 110.00 |
| L-Threonine | 19.00 | 19.00 | 19.00 | 19.00 |
| L-Tyrosine | 9.00 | 9.00 | 9.00 | 9.00 |
| L-Tryptophan | 14.28 | 14.28 | 14.28 | 14.28 |
| L-Valine | 23.00 | 23.00 | 23.00 | 23.00 |
| Vitamin A (retinyl acetate) | | | 0.65 | 0.65 |
| Vitamin B6 (pyridoxine hydrochloride) | | 0.017 | 0.017 | 0.017 |
| Vitamin B12 (cyanocobalamin) | | | 0.00007 | 0.00007 |
| Folic Acid | | 0.099 | 0.099 | 0.099 |
| L-Ascorbic acid | 15.00 | 15.00 | 15.00 | 15.00 |
| Vitamin D3 (cholecalciferol) | | | 0.31 | 0.31 |
| Vitamin E (DL-α-tocopherol acetate) | | | 380 | 380 |
| D-Glucose | 2,000.00 | 2,000.00 | 2,000.00 | 50,000 |
| Water | QS | QS | QS | QS |

Various evaluations and studies with compositions 5A-5D significantly outperformed standard-of-care crystalloid fluids such as NS and LR. Each of these compositions is thus likewise expected to provide improved beneficial results when used as an intravenous solution replacement.

The compositions and methods described herein may be embodied in other specific forms without departing from the spirit of the disclosure. Any equivalent embodiments are intended to be within the scope of this disclosure. Indeed, various modifications in addition to those shown and described herein will become apparent to those skilled in the art from the foregoing description. Such modifications are also intended to fall within the scope of the appended claims.

The invention claimed is:

1. A method of reducing extravasation in a subject receiving or in need of receiving intravenous fluids, the method comprising administering to the subject a sterile bioactive fluid composition comprising:
   a) about 56 to about 140 μmol/L of serine and/or salts thereof, or about 90 to about 240 μmol/L of threonine and/or salts thereof, or combinations thereof;
   b) at least one additional component chosen from chloride, sodium, copper, zinc, magnesium, phosphate, potassium, acetate, pyruvate, malic acid, and/or salts thereof; and
   c) a physiologically acceptable carrier fluid,
   wherein the sterile bioactive fluid composition is administered to the subject intravenously,
   wherein the sterile bioactive fluid composition is in crystalloid form, and
   wherein extravasation is reduced compared to intravenous administration of normal saline.

2. The method of claim 1, wherein the subject is receiving or in need of receiving intravenous fluids for resuscitative care, supportive care, treatment, and/or for delivery of therapeutics, active agents, and/or diagnostics.

3. The method of claim 1, wherein the sterile bioactive fluid composition is free of proteins.

4. The method of claim 1, wherein the physiologically acceptable carrier fluid comprises water.

5. The method of claim 1, wherein the sterile bioactive fluid composition comprises:
   a) from about 56-140 μmol/L of serine and/or from about 92-240 μmol/L of threonine;
   b) at least one additional component chosen from about 95-115 mmol/L of chloride, from about 115-150 mmol/L of sodium, from about 5-24 μmol/L of copper, from about 15-70 μmol/L of zinc, from about 0.2-1.0 mmol/L of magnesium, from about 0.8-2 mmol/L of phosphate, from about 2-5 mmol/L of potassium, from about 2-45 mmol/L of acetate, from about 0.03-2.5 mmol/L of pyruvate, from about 1-15 mmol/L of malic acid, and/or salts thereof; and
   c) water.

6. The method of claim 1, wherein the sterile bioactive fluid composition further comprises:
   a) at least one component chosen from:
      i. amino acids other than serine and threonine, and/or
      ii. salts of amino acids other than serine and threonine.

7. The method of claim 6, wherein the sterile bioactive fluid composition further comprises:
   a) at least one amino acid and/or salt thereof chosen from histidine, isoleucine, leucine, lysine, methionine, phenylalanine, tryptophan, valine, and/or salts thereof.

8. The method of claim 1, wherein the sterile bioactive fluid composition further comprises at least one additional component chosen from:
   a) β-alanine, arginine, glutamine, ornithine, taurine, and/or salts thereof; and/or
   b) Vitamin C, glucose, and/or salts thereof.

9. The method of claim 7, wherein the sterile bioactive fluid composition further comprises:
   a) one or more of the following amino acids or salts thereof: from about 26-120 μmol/L of histidine, from about 42-100 μmol/L of isoleucine, from about 66-170 μmol/L of leucine, from about 150-220 μmol/L of lysine, from about 16-30 μmol/L of methionine, from about 41-68 μmol/L of phenylalanine, from about 92-240 μmol/L of threonine, from about 25-150 μmol/L of tryptophan, and/or from about 150-310 μmol/L of valine.

10. The method of claim 8, wherein the sterile bioactive fluid composition further comprises:
    a) one or more of the following amino acids or salts thereof: from about 200-600 μmol/L of β-alanine, from about 10-70 μmol/L of arginine, from about 390-650 μmol/L of glutamine, from about 27-80 μmol/L of ornithine, and/or from about 45-440 μmol/L of taurine; and/or
    b) one or more of the following compounds or salts thereof: from about 11-120 μmol/L of Vitamin C, and/or from about 3-25 μmol/L of glucose.

* * * * *